(12) United States Patent
Hatzfeld et al.

(10) Patent No.: US 8,847,016 B2
(45) Date of Patent: Sep. 30, 2014

(54) RICE PROMOTERS

(75) Inventors: Yves Hatzfeld, Lille (FR); Willem Broekaert, Dilbeek (BE)

(73) Assignee: Crop Design N.V. (BE)

( * ) Notice: Subject to any disclaimer, the term of this patent is extended or adjusted under 35 U.S.C. 154(b) by 0 days.

(21) Appl. No.: 13/471,930

(22) Filed: May 15, 2012

(65) Prior Publication Data

US 2013/0007914 A1 Jan. 3, 2013

Related U.S. Application Data

(62) Division of application No. 12/229,130, filed on Aug. 20, 2008, which is a division of application No. 10/525,647, filed as application No. PCT/EP2004/050081 on Feb. 4, 2004, now Pat. No. 7,427,676.

(30) Foreign Application Priority Data

Feb. 4, 2003 (EP) ..................................... 03075331

(51) Int. Cl.
*C12N 15/82* (2006.01)
*C12N 15/87* (2006.01)

(52) U.S. Cl.
CPC ........ *C12N 15/8234* (2013.01); *C12N 15/8216* (2013.01); *C12N 15/8222* (2013.01)
USPC ........ 800/287; 536/24.1; 800/278; 435/320.1

(58) Field of Classification Search
USPC .......................................................... 800/287
See application file for complete search history.

(56) References Cited

U.S. PATENT DOCUMENTS

2007/0020621 A1 * 1/2007 Boukharov et al. ............... 435/6

* cited by examiner

*Primary Examiner* — Li Zheng
(74) *Attorney, Agent, or Firm* — Barbara E. Johnson, Esq.

(57) ABSTRACT

The invention provides several promoters isolated from *Oryza sativa*, which promoters are capable of driving and/or regulating the expression of an operably linked nucleic acid in a plant. The expression patterns of the promoters according to the invention have been studied in *Oryza sativa* and some of the promoters displayed specific activity in particular cells, tissues or organs of the plant, while others displayed constitutive expression throughout substantially the whole plant. Some promoters showed weak expression, while others were strongly active.

3 Claims, 11 Drawing Sheets

PRO0110 RCc3

PRO0005 putative beta-amylase

PRO0009 putative cellulose synthase

PRO058 proteinase inhibitor Rgpi9

PRO061 beta-expansion EXPB9

PRO0063 structural protein

PRO0081 putative caffeoyl CoA 3-O-methyltransferase

PRO0091 prolamin RP5

PRO0095 putative methionine aminopeptidase

PRO0111 uclacyanin 3-like protein

PRO0116 26S proteaseome regulatory particle non-ATPase subunit 11

PRO0117 putative 40S ribosomal protein

PRO0122 chlorophyll a/b binding protein precursor (Cab27)

PRO0123 putative protochlorophyllide reductase

PRO0133 chitinase Cht-3

PRO01151 WSI18

PRO0169 acquaporine

PRO0170 high mobility group protein

A B plant

B A plant

OLD    YOUNG    SEED

C Calli

PRO0171 reversibly glycosylated protein RGP1

PRO0173 cytosolic MDH

PRO0175 RAB21

PRO0177 Cdc2-1

RICE PROMOTERS

CROSS-REFERENCE TO RELATED APPLICATIONS

The present patent application claims priority and forms part of a chain of continuing applications as follows: the present application, U.S. Ser. No. 13/471,930, filed 15 May 2012, is a division U.S. Ser. No. 12/229,130 filed 20 Aug. 2008, which is a division of U.S. Ser. No. 10/525,647 filed 24 Feb. 2005, now U.S. Pat. No. 7,427,676, which is a Section 371 U.S. application based upon international application number PCT/EP04/50081 filed 4 Feb. 2004, which claims priority to EPO 03075331.3 filed 4 Feb. 2003, each of which is incorporated herein by reference.

The present invention relates to the field of plant molecular biology, more particularly to nucleic acid sequences useful for driving and/or regulating expression of an operably linked nucleic acid in plants. The isolation of these nucleic acid sequences from rice, as well as their use in driving and/or regulating expression of an operably linked nucleic acid is disclosed. The present invention therefore concerns promoters, hybrid promoters, genetic constructs, expression cassettes, transformation vectors, expression vectors, host cells and transgenic plants comprising the isolated nucleic acids according to the present invention. The present invention also concerns methods for driving and/or regulating expression of a nucleic acid and methods for the production of transgenic plants.

Gene expression is dependent on initiation of transcription, which is mediated via the transcription initiation complex. Gene expression is also dependent on regulation of transcription, which regulation determines how strong, when or where a gene is expressed. Said regulation of gene expression may be mediated via transcriptional control elements, which are generally embedded in the nucleic acid sequence 5'-flanking or upstream of the expressed gene. This upstream nucleic acid region is often referred to as a "promoter" since it promotes the binding, formation and/or activation of the transcription initiation complex and therefore is capable of driving and/or regulating expression of the 3' downstream nucleic acid sequence.

Genetic engineering of plants with the aim of obtaining a useful plant phenotype, often involves heterologous gene expression, which is generally mediated by a promoter capable of driving and/or regulating expression of an operably linked heterologous nucleic acid. The phenotype of the host plant only depends on the contribution of the heterologous nucleic acid, but also on the contribution of the specific expression pattern of the chosen promoter determining how, where and when that heterologous nucleic acid is expressed. Accordingly, the choice of promoter with a suitable expression pattern is of crucial importance for obtaining the suitable phenotype. A person skilled in the art will need to have available different promoters, to determine the optimal promoter for a particular nucleic acid. For many different host plants, this availability is rather limited and there is therefore a continuing need to provide new promoters with various expression profiles.

The nucleic acids as presented in SEQ ID NO 1 to 22 were isolated from *Oryza sativa* and have been found to be capable of driving and regulating expression of an operably linked nucleic acid; their expression patterns have also been characterized. Therefore the present invention offers a collection of hitherto unknown isolated nucleic acids, which isolated nucleic acids are useful as promoters.

Accordingly, the present invention provides an isolated promoter capable of driving and/or regulating expression, comprising:
  (a) an isolated nucleic acid as given in any one of SEQ ID NO 1 to 22 or the complement of any one of SEQ ID NO 1 to 22; or
  (b) an isolated nucleic acid having at least 90% sequence identity with any of the DNA sequences as given in any one of SEQ ID NO 1 to 22; or
  (c) an isolated nucleic acid specifically hybridizing under stringent conditions with any of the DNA sequences as given in any one of SEQ ID NO 1 to 22; or
  (d) an isolated nucleic acid as defined in any one of (a) to (c), which is interrupted by an intervening sequence; or
  (e) a fragment of any of the nucleic acids as defined in (a) to (d), which fragment is capable of driving and/or regulating expression.

The term "isolated" as used herein means being removed from its original source. Preferably, the "isolated" promoter is free of sequences (such as protein encoding sequences or other sequences at the 3' end) that naturally flank the promoter in the genomic DNA of the organism from which the promoter is derived. Further preferably, the "isolated" promoter is also free of sequences that naturally flank it at the 5' end. Further preferably, the "isolated" promoter may comprise less than about 5 kb, 4 kb, 3 kb, 2 kb, 1.5 kb, 1.2 kb, 1 kb, 0.8 kb, 0.5 kb or 0.1 kb of nucleotide sequences that naturally occur with the promoter in genomic DNA from the organism of which the promoter is derived.

The present invention is not limited to the nucleic acids as presented by SEQ ID NO 1 to 22. A person skilled in the art will recognize that variants or fragments of a nucleic acid may occur, whilst maintaining the same functionality. These variants or fragments may be man made (e.g. by genetic engineering) or may even occur in nature. Therefore the present invention extends to variant nucleic acids and fragments of any of SEQ ID NO 1 to 22, which variants or fragments are useful in the methods of the present invention. Such variants and fragments include:
  (a) an isolated nucleic acid as given in any one of SEQ ID NO 1 to 22 or the complement of any one of SEQ ID NO 1 to 22; or
  (b) an isolated nucleic acid having at least 90% sequence identity with any of the DNA sequences as given in any one of SEQ ID NO 1 to 22; or
  (c) an isolated nucleic acid specifically hybridizing under stringent conditions with any of the DNA sequences as given in any one of SEQ ID NO 1 to 22; or
  (d) an isolated nucleic acid as defined in any one of (a) to (c), which is interrupted by an intervening sequence; or
  (e) a fragment of any of the nucleic acids as defined in (a) to (d), which fragment is capable of driving and/or regulating expression.

Suitable variants of any one of SEQ ID NO 1 to 22 encompass homologues which have in increasing order of preference at least 90%, 91%, 92%, 93%, 94%, 95%, 96%, 97%, 98% or 99% sequence identity with any one of the nucleic acids as represented in SEQ ID NO 1 to 22.

The percentage of identity may be calculated using an alignment program. Preferably a pair wise global alignment program may be used, which implements the algorithm of Needleman-Wunsch (J. Mol. Biol. 48: 443-453, 1970). This algorithm maximizes the number of matches and minimizes the number of gaps. Such programs are for example GAP, Needle (EMBOSS package), stretcher (EMBOSS package) or Align X (Vector NTI suite 5.5) and may use the standard parameters (for example gap opening penalty 15 and gap extension penalty 6.66). Alternatively, a local alignment program implementing the algorithm of Smith-Waterman (Advances in Applied Mathematics 2, 482-489 (1981)) may be used. Such programs are for example Water (EMBOSS package) or matcher (EMBOSS package). "Sequence identity" as used herein is preferably calculated over the entire length of the promoters as represented by any one of SEQ ID NO 1 to 22. The length of these promoters is presented in Table 2.

Search and identification of homologous nucleic acids, would be well within the realm of a person skilled in the art. Such methods involve screening sequence databases with the sequences provided by the present invention, for example any one of SEQ ID NO 1 to 22, preferably in a computer readable form. Useful sequence databases include but are not limited to Genbank, the European Molecular Biology Laboratory Nucleic acid Database (EMBL) or versions thereof, or the MIPS database. Different search algorithms and software for the alignment and comparison of sequences are well known in the art. Such software includes, for example GAP, BESTFIT, BLAST, FASTA and TFASTA. Preferably BLAST software is used, which calculates percent sequence identity and performs a statistical analysis of the similarity between the sequences. The suite of programs referred to as BLAST programs has 5 different implementations: three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., GenomeAnalysis, 1: 543, 1997). The software for performing BLAST analysis is publicly available through the National Centre for Biotechnology Information.

The sequences of the genome of *Arabidopsis thaliana* and the genome of *Oryza sativa* are now available in public databases such as Genbank. Other genomes are currently being sequenced. Therefore, it is expected that as more sequences of the genomes of other plants become available, homologous promoters may be identifiable by sequence alignment with any one of SEQ ID NO 1 to SEQ ID NO 22. The skilled person will readily be able to find homologous promoters from other plant species, for example from other crop plants, such as maize. Homologous promoters from other crop plants are especially useful for practising the methods of the present invention in crop plants.

One example of homologues having at least 90% sequence identity with any one of SEQ ID NO to 22 are allelic variants of any one of SEQ ID NO 1 to 22. Allelic variants are variants of the same gene occurring in two different individuals of the same species and usually allelic variants differ by slight sequence changes. Allelic variants may encompass Single Nucleotide Polymorphisms (SNPs) as well as Small Insertion/Deletion Polymorphisms (INDELs). The size of INDELs is usually less than 100 bp. SNPs and INDELs form the largest set of sequence variants in naturally occurring polymorphic strains of most organisms.

Homologues suitable for use in the methods according to the invention may readily be isolated from their source organism via the technique of PCR or hybridization. Their capability of driving and/or regulating expression may readily be determined, for example, by following the methods described in the Examples section by simply substituting the sequence used in the actual Example with the homologue.

Other suitable variants of any one of SEQ ID NO 1 to 22 encompassed by the present invention are nucleic acids specifically hybridising under stringent conditions to any one of the nucleic acids of SEQ ID NO 1 to 22. The term "hybridising" means annealing to substantially homologous complementary nucleotide sequences in a hybridization process. Tools in molecular biology relying on such a hybridization process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination, Northern blotting (RNA blotting), Southern blotting (DNA blotting). The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid sequence. High stringency conditions for hybridisation include high temperature and/or low sodium/salt concentration (salts include sodium as for example in NaCl and $Na_3$-citrate) and/or the inclusion of formamide in the hybridisation buffer and/or lowering the concentration of compounds such as SDS (sodium dodecyl sulphate detergent) in the hybridisation buffer and/or exclusion of compounds such as dextran sulphate or polyethylene glycol (promoting molecular crowding) from the hybridisation buffer. Specifically hybridising under stringent conditions means that the sequences have to be very similar. Specific hybrisization under stringent conditions is preferably carried out at a temperature of 60° C. followed by washes in 0.1 to 1×SSC, 0.1×SDS, and 1×SSC, 0.1×SDS.

The invention also relates to a nucleic acid molecule of at least 15 nucleotides in length hybridizing specifically with any of the nucleic acids of the invention. The invention also relates to a nucleic acid molecule of at least 15 nucleotides in length specifically amplifying a nucleic acid of the invention by polymerase chain reaction.

Another variant of any of SEQ ID NO 1 to 22 encompassed by the present invention are nucleic acids corresponding to any one of SEQ ID NO 1 to 22 or variants thereof as described hereinabove, which are interrupted by an intervening sequence. For example, any of the nucleic acids as presented in SEQ ID NO 1 to 22 may be interrupted by an intervening sequence. With "intervening sequences" is meant any nucleic acid or nucleotide, which disrupts another sequence. Examples of intervening sequences comprise introns, nucleic acid tags, T-DNA and mobilizable nucleic acids sequences such as transposons or nucleic acids that can be mobilized via recombination. Examples of particular transposons comprise Ac (activator), Ds (Dissociation), Spm (suppressor-Mutator) or En. The introduction of introns into promoters is now widely applied. The methods according to the present invention may also be practised using a nucleic acid sequence according to any one of SEQ ID NO 1 to 22 provided with an intron. In case the intervening sequence is an intron, alternative splice variants of the nucleic acids according to the invention may arise. The term "alternative splice variant" as used herein encompasses variants of a nucleic acid sequence in which intervening introns have been excised, replaced or added. Such splice variants may be found in nature or may be manmade. Methods for making such promoters with an intron or for making the corresponding splice variants are well known in the art.

Variants interrupted by an intervening sequence, suitable for use in the methods according to the invention may readily be determined for example by following the methods described in the Examples section by simply substituting the sequence used in the actual Example with the variant.

The variant nucleic acids as described hereinabove may be found in nature (for example allelic variants or splice variants). Additionally and/or alternatively, variants of any one of SEQ ID NO 1 to 22 as described hereinabove may be manmade via techniques well known in the art involving for example mutation, substitution, insertion, deletions or derivation. The present invention also encompasses such variants, as well as their use in the methods of the present invention.

A "mutation variant" of a nucleic acid may readily be made using recombinant DNA manipulation techniques or nucleotide synthesis. Examples of such techniques include site directed mutagenesis via M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols. Alternatively, the nucleic acid of the present invention may be randomly mutated.

A "substitutional variant" refers to those variants in which at least one residue in the nucleic acid sequence has been removed and a different residue inserted in its place. Nucleic acid substitutions are typically of single residues, but may be clustered depending upon functional constraints placed upon the nucleic acid sequence; insertions usually are of the order of about 1 to about 10 nucleic acid residues, and deletions can range from about 1 to about 20 residues.

An "insertional variant" of a nucleic acid is a variant in which one or more nucleic acid residues are introduced into a predetermined site in that nucleic acid. Insertions may comprise 5'-terminal and/or 3'-terminal fusions as well as intra-sequence insertions of single or multiple nucleotides. Generally, insertions within the nucleic acid sequence will be smaller than 5'- or 3'-terminal fusions, of the order of about 1 to 10 residues. Examples of 5'- or 3'-terminal fusions include the coding sequences of binding domains or activation domains of a transcriptional activator as used in the yeast two-hybrid system or yeast one-hybrid system, or of phage coat proteins, (histidine)$_6$-tag, glutathione S-transferase-tag, protein A, maltose-binding protein, dihydrofolate reductase, Tag●100 epitope, c-myc epitope, FLAG®-epitope, lacZ, CMP (calmodulin-binding peptide), HA epitope, protein C epitope and VSV epitope.

The term "derivative" of a nucleic acid may comprise substitutions, and/or deletions and/or additions of naturally and non-naturally occurring nucleic acid residues compared to the natural nucleic acid. Derivatives may, for example, comprise methylated nucleotides, or artificial nucleotides.

Also encompassed with in the present invention are promoters, comprising a fragment of any of the nucleic acids as presented by any one of SEQ ID NO 1 to 22 or variants thereof as described hereinabove. A "fragment" as used herein means a portion of a nucleic acid sequence. Suitable fragments useful in the methods of the present invention are functional fragments, which retain at least one of the functional parts of the promoter and hence are still capable of driving and/or regulating expression. Examples of functional fragments of a promoter include the minimal promoter, the upstream regulatory elements, or any combination thereof.

Suitable fragments may range from at least about 20 base pairs or about 50, 100, 150, 200, 250, 300, 350, 400, 450, 500, 550, 600, 650, 700, 750, 800, 850, 900, 950 or 1000 base pairs, up to about the full length sequence of the invention. These base pairs are typically immediately upstream of the transcription initiation start, but alternatively may be from anywhere in the promoter sequence.

Suitable fragments useful in the methods of the present invention may be tested for their capability of driving and/or regulating expression by standard techniques well known to the skilled person, or by the following method described in the Example section.

The promoters as disclosed in any one of SEQ ID NO 1 to 22 are isolated as nucleic acids of approximately 1.2 kb from the upstream region of particular rice coding sequences (CDS). These nucleic acids may include typical elements of a promoter, which are presented in FIG. 1. Generally, a promoter may comprises from coding sequence to the upstream direction: (i) an 5'UTR of pre-messenger RNA, (ii) a minimal promoter comprising the transcription initiation element (INR) and more upstream a TATA box, and (iii) may contain regulatory elements that determine the specific expression pattern of the promoter.

The term "promoter" as used herein is taken in a broad context and refers to regulatory nucleic acid sequences capable of effecting (driving and/or regulating) expression of the sequences to which they are operably linked. A "promoter" encompasses transcriptional regulatory sequences derived from a classical genomic gene. Usually a promoter comprises a TATA box, which is capable of directing the transcription initiation complex to the appropriate transcription initiation start site. However, some promoters do not have a TATA box (TATA-less promoters), but are still fully functional for driving and/or regulating expression. A promoter may additionally comprise a CCAAT box sequence and additional regulatory elements (i.e. upstream activating sequences or cis-elements such as enhancers and silencers). A "promoter" may also include the transcriptional regulatory sequences of a classical prokaryotic gene, in which case it may include a −35 box sequence and/or a −10 box transcriptional regulatory sequences.

"Driving expression" as used herein means promoting the transcription of a nucleic acid.

"Regulating expression" as used herein means influencing the level, time or place of transcription of a nucleic acid. The promoters of the present invention may thus be used to increase, decrease or change in time and/or place transcription of a nucleic acid. For example, they may be used to limit the transcription to certain cell types, tissues or organs, or during a certain period of time, or in response to certain environmental conditions.

The promoter is preferably a plant-expressible promoter. The term "plant-expressible" means being capable of regulating expression in a plant, plant cell, plant tissue and/or plant organ. Accordingly, the invention encompasses an isolated nucleic acid as mentioned above, capable of regulating transcription of an operably linked nucleic acid in a plant or in one or more particular cells, tissues or organs of a plant.

The expression pattern of the promoters according to the present invention were studied in detail and it was found that many of them were tissue-specific. Accordingly, the present invention provides "tissue-specific" promoters. The term "tissue-specific" shall be taken to indicate that expression is predominantly in a particular tissue, tissue-type, organ or any other part of the organism, albeit not necessarily exclusively in said tissue, tissue-type, organ or other part. Accordingly, the invention encompasses an isolated nucleic acid as mentioned above, capable of driving and/or regulating expression (of an operably linked nucleic acid) in a tissue-specific manner. Expression may be driven and/or regulated in the seed, embryo, scutellum, aleurone, endosperm, leaves, flower, calli, meristem, shoot meristem, discriminating centre, shoot, shoot meristem and root. In grasses the shoot meristem is located in the so-called discrimination zone from where the shoot and the leaves originate.

A tissue-specific promoter is one example of a so-called "regulated promoter". These promoters are regulated by endogenous signals such as the presence of certain transcription factors, metabolites, plant hormones, or exogenous signals, such as ageing, stresses or nutritional status. These regulations may have an effect on one or more different levels such spatial specificity or temporal specificity. Encompassed within the present invention is a nucleic acid as described hereinabove, which is a "regulated promoter". Examples of regulated promoters are cell-specific promoters, tissue-specific promoters, organ-specific promoters, cell cycle-specific promoters, inducible promoters or young tissue-specific promoters.

Alternatively and/or additionally, some promoters of the present invention display a constitutive expression pattern. Accordingly, the present invention provides a promoter as described hereinabove, which is a constitutive promoter. The term "constitutive" means having no or very few spatial or temporal regulations. The term "constitutive expression" as used herein refers to a substantially continuously expression in substantially all tissues of the organism. The skilled craftsman will understand that a "constitutive promoter" is a promoter that is active during most, but not necessarily all, phases of growth and development of the organism and throughout most, but not necessarily all, parts of an organism.

The "expression pattern" of a promoter is not only influenced by the spatial and temporal aspects, but also by the level of expression. The level of expression is determined by the so-called "strength" of a promoter. Depending on the resulting expression level, a distinction is made herein between "weak" or "strong" promoters. Generally by "weak promoter" is meant a promoter that drives expression of an operably linked nucleic acid at levels of about $1/10000$ transcripts to about $1/100000$ transcripts to about $1/500000$ transcripts. Generally, by "strong promoter" is meant a promoter that drives expression at levels of about $1/10$ transcripts, to about $1/100$ or to about $1/1000$ transcripts.

According to a particular embodiment, the invention provides an isolated promoter as mentioned hereinabove, which is a hybrid promoter. The term "hybrid promoter" as used herein refers to a chimeric promoter made, for example, synthetically, for example by genetic engineering. Preferred hybrid promoters according to the present invention comprise a part, preferably a functional part, of one of the promoters according to the present invention and at least another part, preferably a functional part of a promoter. The latter part, may be a part of any promoter, including any one of the promoters according to the present invention and other promoters. One example of a hybrid promoter comprises regulatory element(s) of a promoter according to the present invention combined with the minimal promoter of another promoter. Another example of a hybrid promoter is a promoter comprising additional regulatory elements to further enhance its activity and/or to alter its spatial and/or temporal expression pattern.

The present invention also provides use of a functional fragment of any one of SEQ ID NO 1 to 22 or variant thereof for changing the expression pattern of a promoter. In such methods, at least part of any of the nucleic acids according to the present invention are combined with at least one fragment of another promoter.

Further, the invention provides a genetic construct comprising:
  (a) An isolated promoter as defined hereinabove
  (b) A heterologous nucleic acid sequence operably linked to isolated promoter of (a), and optionally
  (c) A 3' transcription terminator The term "genetic construct" as used herein means a nucleic acid made by genetic engineering.

The term "operably linked" to a promoter as used herein means that the transcription is driven and/or regulated by that promoter. A person skilled in the art will understand that being operably linked to a promoter preferably means that the promoter is positioned upstream (i.e. at the 5'-end) of the operably linked nucleic acid. The distance to the operably linked nucleic acid may be variable, as long as the promoter of the present invention is capable of driving and/or regulating the transcription of the operably linked nucleic acid. For example, between the promoter and the operably linked nucleic acid, there might be a cloning site, an adaptor, a transcription or translation enhancer.

The operably linked nucleic acid may be any coding or non-coding nucleic acid. The operably linked nucleic acid may be in the sense or in the anti-sense direction. Typically in the case of genetic engineering of host cells, the operably linked nucleic acid is to be introduced into the host cell and is intended to change the phenotype of the host cell. Alternatively, the operably linked nucleic acid is an endogenous nucleic acid from the host cell.

The term "heterologous" as used herein is intended to be "heterologous to the promoter of the present invention". A nucleic acid that is heterologous to the promoter of the present invention is not naturally occurring in the nucleic acid sequences flanking the promoter of the present invention when it is in its biological genomic environment. While the nucleic acid may be heterologous to the promoter of the present invention, it may be homologous or native or heterologous or foreign to the plant host cell. The heterologous operably linked nucleic acid may be any nucleic acid (for example encoding any protein), provided that it comprises or it is flanked by at least one nucleotide which is normally not flanking the promoter of the present invention.

The term "transcription terminator" as used in (c) refers to a DNA sequence at the end of a transcriptional unit which signals termination of transcription. Terminators are 3'-non-translated DNA sequences usually containing a polyadenylation signal, which facilitates the addition of polyadenylate sequences to the 3'-end of a primary transcript. Terminators active in and/or isolated from viruses, yeasts, moulds, bacteria, insects, birds, mammals and plants are known and have been described in literature. Examples of terminators suitable for use in the genetic constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

The present invention also provides an expression cassette, a transformation vector or a plant expression vector comprising a genetic construct as described above.

An "expression cassette" as meant herein refers to a minimal genetic construct necessary for expression of a nucleic acid. A typical expression cassette comprises a promoter-gene-terminator combination. An expression cassette may additionally comprise cloning sites, for example Gateway™ recombination sites or restriction enzyme recognition sites, to allow easy cloning of the operably linked nucleic acid or to allow the easy transfer of the expression cassette into a vector. An expression cassette may further comprise 5' untranslated regions, 3' untranslated regions, a selectable marker, transcription enhancers or translation enhancers.

With "transformation vector" is meant a genetic construct, which may be introduced in an organism by transformation and may be stably maintained in said organism. Some vectors may be maintained in for example *Escherichia coli*, *A. tumefaciens*, *Saccharomyces cerevisiae* or *Schizosaccharomyces pombe*, while others such as phagemids and cosmid vectors, may be maintained in bacteria and/or viruses. Transformation vectors may be multiplied in their host cell and may be isolated again therefrom to be transformed into another host cell. Vector sequences generally comprise a set of unique sites recognized by restriction enzymes, the multiple cloning site (MCS), wherein one or more non-vector sequence(s) can be inserted. Vector sequences may further comprise an origin of replication which is required for maintenance and/or replication in a specific host cell. Examples of origins of replication include, but are not limited to, the f1-ori and colE1.

"Expression vectors" form a subset of transformation vectors, which, by virtue of comprising the appropriate regulatory sequences, enable expression of the inserted non-vector sequence(s). Expression vectors have been described which are suitable for expression in bacteria (e.g. *E. coli*), fungi (e.g. *S. cerevisiae*, *S. pombe*, *Pichia pastoris*), insect cells (e.g. baculoviral expression vectors), animal cells (e.g. COS or CHO cells) and plant cells. One suitable expression vector according to the present invention is a plant expression vector, useful for the transformation of plant cells, the stable integration in the plant genome, the maintenance in the plant cell and the expression of the non-vector sequences in the plant cell.

Typically, a plant expression vector according to the present invention comprises a nucleic acid of any one of SEQ ID NO 1 to 22 or a variant thereof as described hereinabove, optionally operably linked to a second nucleic acid. Typically, a plant expressible vector according to the present invention, further comprises T-DNA regions for stable integration into the plant genome (for example the left border and the right border regions of the Ti plasmid).

The genetic constructs of the invention may further comprise a "selectable marker". As used herein, the term "selectable marker" includes any gene, which confers a phenotype to a cell in which it is expressed, to facilitate the identification and/or selection of cells that are transfected or transformed. Suitable markers may be selected from markers that confer antibiotic or herbicide resistance. Cells containing the genetic construct will thus survive antibiotics or herbicide concentrations that kill untransformed cells. Examples of selectable marker genes include genes conferring resistance to antibiotics (such as nptII encoding neomycin phosphotransferase capable of phosphorylating neomycin and kanamycin, or hpt encoding hygromycin phosphotransferase capable of phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example beta-glucuronidase, GUS), luminescence (such as luciferase) or fluorescence (Green Fluorescent Protein, GFP, and derivatives thereof). Further examples of suitable selectable marker genes include the ampicillin resistance (Ampr), tetracycline resistance gene (Tcr), bacterial kanamycin resistance gene (Kanr), phosphinothricin resistance gene, and the chloramphenicol acetyltransferase (CAT) gene, amongst others.

Furthermore, the present invention encompasses a host cell comprising an isolated promoter, or a genetic construct, or an expression cassette, or a transformation vector or an expression vector according to the invention as described hereinabove. In particular embodiments of the invention, the host cell is selected from bacteria, algae, fungi, yeast, plants, insect or animal host cells.

In one particular embodiment, the invention provides a transgenic plant cell comprising an isolated promoter according to the invention, or an isolated nucleic acid, or a genetic construct, or an expression cassette, or a transformation vector or an expression vector according to the invention as described hereinabove. Preferably said plant cell is a dicot plant cell or a monocot plant cell, more preferably a cell of any of the plants as mentioned herein. Preferably, in the transgenic plant cell according to the invention, the promoter or the genetic construct of the invention is stably integrated into the genome of the plant cell.

The invention also provides a method for the production of a transgenic plant, comprising:
  (a) Introducing into a plant cell an isolated promoter, for example any one of SEQ ID NO 1 to SEQ ID NO 22, or a variant or fragment thereof, or a genetic construct, or an expression cassette, or a transformation vector or an expression vector according to the present invention and as described hereinabove, and
  (b) Cultivating said plant cell under conditions promoting plant growth.

"Introducing" the above mentioned isolated promoter, or genetic construct, or expression cassette, or transformation vector or expression vector, into a host cell (e.g. plant cell) is preferably achieved by transformation. The term "transformation" as used herein encompasses the transfer of an exogenous polynucleotide into a host cell, irrespective of the method used for transfer. In particular for plants, tissues capable of clonal propagation, whether by organogenesis or embryogenesis, are suitable to be transformed with a genetic construct of the present invention and a whole plant may be regenerated therefrom. The particular tissue chosen will vary depending on the clonal propagation systems available for, and best suited to, the particular plant species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a plant cell and may be maintained non-integrated, for example, as a plasmid. Alternatively, it may be integrated into the plant genome.

Transformation of a plant species is now a fairly routine technique. Advantageously, any of several transformation methods may be used to introduce the nucleic acids of the invention into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen. Genet. 202, 179-185); DNA or RNA-coated particle bombardment (Klein T. M. et al., 1987, Nature 327, 70) infection with (non-integrative) viruses and the like. A preferred transformation method for the production of transgenic plant cells according to the present invention, is an *Agrobacterium* mediated transformation method.

Transgenic rice plants comprising any one of the promoters of the present invention are preferably produced via *Agrobacterium*-mediated transformation using any of the well-known methods for rice transformation, such as the ones described in any of the following: published European patent application EP 1198985 A1, Aldemita and Hodges (Planta, 199, 612-617, 1996); Chan et al. (Plant Mol. Biol. 22 (3) 491-506, 1993); Hiei et al. (Plant J. 6 (2) 271-282, 1994); which disclosures are incorporated by reference herein as if fully set forth. In the case of corn transformation, the preferred method is as described in either Ishida et al. (Nat. Biotechnol. 1996 June; 14(6): 745-50) or Frame et al. (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest (which could be under the control of any of the promoters of the present invention), following which the transformed material may be cultivated under conditions promoting plant growth.

The resulting transformed plant cell may then be used to regenerate a transformed plant in a manner known to persons skilled in the art. Accordingly, the method for the production of a transgenic plant as described hereinabove, may further comprise regenerating a plant from said plant cell of (a).

The present invention further provides a plant comprising a plant cell as described hereinabove. The plants may also be able to grow, or even reach maturity including for example fruit production, seed formation, seed ripening and seed setting.

Furthermore, progeny may be produced from these seeds, which progeny may be fertile. Alternatively or additionally, the transformed and regenerated plants may also produce progeny by non-sexual propagation such as cloning, grafting. The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Following DNA transfer and growth of the transformed cells, putatively transformed plant cells or plants may be evaluated, for instance using Southern analysis, for the presence of the gene of interest, copy number and/or genomic organization. Alternatively or additionally, expression levels or expression patterns of the newly introduced DNA may be undertaken using northern and/or Western analysis, both techniques being well known to persons having ordinary skill in the art.

The present invention clearly extends to plants obtainable by any of the methods according to the present invention, which plants comprise any of the isolated promoters or the constructs of the present invention. The present invention clearly extends to any plant parts and propagules of such plant. The present invention extends further to encompass the progeny of a primary transformed cell, tissue, organ or whole plant that has been produced by any of the aforementioned methods, the only requirement being that progeny exhibit the same genotypic and/or phenotypic characteristic(s) as those produced in the parent by the methods according to the invention. The invention also extends to harvestable parts of a plant, such as but not limited to seeds, leaves, fruits, flowers, stem cultures, stem, rhizomes, roots, tubers, bulbs and cotton fibers.

The term "plant" or "plants" as used herein encompasses whole plants, ancestors and progeny of plants and plant parts, including seeds, shoots, stems, roots (including tubers), and plant cells, tissues and organs. The term "plant" therefore also encompasses suspension cultures, embryos, meristematic regions, callus tissue, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coroniffia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incarnata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoa*- cacia, *Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp. *Vitis vinifera, Watsonia pyramidata, Zantedeschia aethiopica, Zea mays,* amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, trees and algae amongst others. According to a preferred feature of the present invention, the plant is a crop plant such as soybean, sunflower, canola, alfalfa, rapeseed, cotton, tomato, potato, tobacco, squash, papaya, poplar, leguminosa, flax, lupinus or sorghum. According to another preferred embodiment of the present invention the plant is a monocotyledonous plant, such as sugarcane, further preferable a cereal such as rice, maize, wheat, barley, millet, rye or oats.

The invention further provides a method for driving and/or regulating expression of a nucleic acid in a plant or plant cell, comprising:
a) Operably linking a nucleic acid to an isolated nucleic acid according to the invention as described hereinabove, such as to any one of SEQ ID NO 1 to 22 or a variant or fragment thereof, and
b) Introducing the resultant genetic construct into a plant or plant cell.

Preferably the operably linked nucleic acid of (a) is heterologous to the nucleic acids according to the present invention.

This method may further comprise cultivating the transformed plant or plant cell under conditions promoting growth, promoting regeneration and/or promoting maturation.

Furthermore, the expression of the operably linked nucleic acid may be driven and/or regulated in particular cells, tissues or organs of a plant. Accordingly, the invention provides a method as described above, wherein the expression is constitutive expression or tissue-specific expression. For these embodiments, reference is made to the example section where the specific expression patterns of the promoters according to the invention are described and where different types of tissue-specific expression are detailed.

The present invention further encompasses the use of an isolated nucleic acid as defined hereinabove to drive and/or regulate expression of an operably linked nucleic acid.

(i) The person skilled in the art will recognize that provision of sequences SEQ ID NO 1 to 22, readily makes available the tools to isolate related promoters, which may have substantial sequence identity to any of SEQ ID NO 1 to 22. Additionally, provision of sequences SEQ ID NO 23 to 44 (CDS corresponding to the promoters of the present invention, see Table 1), readily makes available the tools to isolate related promoters, of which the related CDSs may have substantial sequence identity to any of SEQ ID NO 23 to 44. Therefore the present invention also encompasses a method for isolating nucleic acids, capable of driving and/or regulating expression of an operably linked nucleic acid, comprising screening a nucleic acid sequence database to find homologues of any of the sequences represented by SEQ ID NO 1 to 22 or SEQ ID NO 23 to 44. Subsequently these homologues are used to screen a library with genomic DNA, which library is for example prepared from the organism of origin of the above mentioned homologue. The screening procedure may for example involve hybridization. Subsequently, the genomic DNA that matches the homologue, is analysed to identify the transcription initiation site and the translation initiation site of the gene corresponding to the homologue. Finally, specific primers are designed for amplification of a nucleic acid located in the region upstream (at the 5' end) of said translation initiation site.

The present invention extends to the identification of regulatory proteins that are involved in the regulation of the activity of the promoters according to the present invention. Such identification may be achieved using a yeast one-hybrid system. In such a yeast one-hybrid system the sequences according to any one of SEQ ID NO 1 to 22 are operably linked to the GAL transcription activator and transformed to a yeast cell culture. That yeast cell culture is again transformed with a library of constructs encoding candidate regulatory factors.

The present invention will now be described with reference to the following figures in which:

FIG. 1 shows a general schematic representation of a promoter. Regulatory elements are sequences that may for example be responsible for special and/or temporal regulation of the promoter activity. The minimal promoter is the minimal sequence necessary and sufficient to drive expression. It includes a TATA box, which is necessary to correctly direct the RNA polymerase II to the transcription initiation site. The transcription initiation element (INR) includes the transcription initiation start site. The 5' untranslated region (5'UTR) is the region that is transcribed into pre-messenger RNA and eventually into mRNA, but is not translated into protein. The translation initiation codon is represented by the startcodon ATG.

FIG. 2 is a map of the vector p4581 useful for expression in plants of a β-glucuronidase (GUS) gene under control of any one of the promoters according to the invention. This binary vector comprises a Gateway recombination cassette, suitable for the recombination cloning of any of the promoters of the present invention in front of the *Escherichia coli* β-glucuronidase (GUS) gene. This cassette contains a chloramphenicol resistance gene (CamR) and the ccdB suicide gene for counter selection of non-recombined plasmids, This GUS expression cassette further comprises the double terminator sequence T-zein and T-rbcS-deltaGA. This expression cassette is located within the left border (LB repeat, LB Ti C58) and the right border (RB repeat, RB Ti C58) of the nopaline Ti plasmid. Cloned within these borders are also selectable marker and a screenable marker genes each under control of a constitutive promoter and a terminator sequence. This vector also contains an origin of replication (pBR322) for bacterial replication and a bacterial selectable marker (Spe/SmeR) for bacterial selection.

The following figures show the results of the GUS staining of plants or plant parts transformed with the reporter vector p4581 carrying a promoter according to the present invention operably linked to the reporter gene GUS. Plants denoted "C plants" are transgenic plants grown to about 5 cm; Plants denoted "B plants" are grown to about 10 cm; and plants denoted "A plants" are grown to maturity. These A plants were used to collect different tissue samples from old leaves, young leaves and seeds.

EXAMPLES

Figure 1:
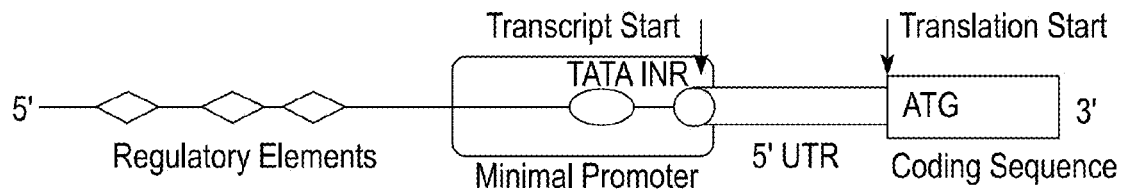

The promoters according to the present invention were isolated as DNA regions spanning about 1.2 kb of the sequence upstream of the translation initiation codon (i.e. first ATG, which codon was excluded) from various rice genes. For determination of their nucleic acid sequence and their expression pattern, the following procedure was followed: First in silico studies on genomic rice sequences were performed. However, procedures based on automated prediction programs to locate promoter-like nucleic acid sequence are highly error prone, even for the localization the best-characterized promoter control elements such as the TATA box and the transcription initiation element (INR). Also, in silico determination of expression pattern is extremely speculative. Therefore, to obtain unambiguous data about the nucleic acid sequence and the expression pattern of the promoters, in vivo studies were performed encompassing (i) isolation of the promoter nucleic acid sequence; (ii) operably linking a reporter gene to the promoter and introducing the resulting genetic construct into a host organisms; (iii) growing the transformed host cell under conditions allowing expression of the reporter gene, and (iv) determination of the reporter gene activity in the different tissues of the host organism. These methods are now described in more detail.

Example 1

Identification and Isolation of the Promoters

Identification of Rice ESTs, the Corresponding Genes and their Location in the Rice Genome Sequence databases, comprising rice sequences, were searched for rice expressed sequence tags (ESTs). Subsequently an "in silico" Northern-blot was performed to allow identification of EST families that are strongly expressed or that are specific for a particular organ. This analysis included normalization of the numbers of ESTs isolated from different plant organs. The ESTs families with an interesting distribution among source cDNA libraries were selected for further analysis and sequence homology searches. After sequence homology searches in combination with scanning scientific data, the genes that correspond to those families of ESTs were identified from sequence databases and a (putative) function and corresponding gene name was given (see Table 1). Subsequently, the corresponding promoter region was isolated by the following procedure. In a first step the TIGR database was searched to find a tentative contig corresponding to an EST family. Sequence homology was found using standard computer programs, such as Blast N using standard parameters (typically G Cost to open a gap=5, E Cost to extend a gap=2, q Penalty for a mismatch in the blast portion of run=−3, r Reward for a match in the blast portion of run=1, e Expectation value=10.0, W Word size=11, v Number of one-line descriptions=100, b Number of alignments to show=100, Matrix=BLOSUM62). The TIGR database (The Institute for Genomic Research), provides Tentative Contigs (TC) which are sequence predictions based on contig building from all known EST, from all known cDNA and from reconstructed mRNA. The TCs used for identification of the promoters of the present invention are represented in Table 1. In a second step these TCs were used to locate the corresponding gene on a genomic sequence, which gene comprises the coding region as well as the promoter region. Generally, these genomic sequences were BAC clones, which are represented herein by their Genbank accession number (see Table 1). From these BAC clones the sequence identity of the promoter region could be determined.

TABLE 1 list of rice promoters of the present invention. The promoter sequences are represented herein by their SEQ ID NO and promoter number (PRO). The coding sequences (CDS) naturally driven by a promoter of the present invention are represented by their name, by SEQ ID NO and by Tentative contig (TC) accession number of the TIGR database. The Genomic sequences (BAC clones or genes) comprising a promoter region of the present invention are represented by their Genbank accession number.

| Prom SEQ ID NO | Prom number | CDS name | CDS SEQ ID NO | CDS TC | BAC clone (*or gene) |
|---|---|---|---|---|---|
| 1 | PRO0110 | RCc3 | 23 | TC89946 | AC037426 |
| 2 | PRO0005 | putative beta-amylase | 24 | TC90358 | AC022457 |
| 3 | PRO0009 | putative cellulose synthase | 25 | TC83635 | AC022457 |
| 4 | PRO0058 | proteinase inhibitor Rgpi9 | 26 | TC83117 | AF044059 |
| 5 | PRO0061 | beta expansine EXPB9 | 27 | TC89913 | AC020666 |
| 6 | PRO0063 | structural protein | 28 | TC89985 | AP001278 |
| 7 | PRO0081 | putative caffeoyl-CoA 3-O-methyltransferase | 29 | TC89891 | AP000364 |
| 8 | PRO0091 | prolamine RP5 | 30 | TC89670 | AF156714* |
| 9 | PRO0095 | putative methionine aminopeptidase | 31 | TC89883 | AC027133 |
| 10 | PRO0111 | uclacyanin 3-like protein | 32 | TC90434 | AJ307662 |
| 11 | PRO0116 | 26S proteasome regulatory particle non-ATPase subunit 11 | 33 | TC83072 | AP000969 |
| 12 | PRO0117 | putative 40S ribosomal protein | 34 | TC90038 | AC090871 |
| 13 | PRO0122 | chlorophyll a/b-binding protein presursor (Cab27) | 35 | TC82936 | AP004700 |
| 14 | PRO0123 | putative protochlorophyllide reductase | 36 | TC89839 | AL606456 |
| 15 | PRO0133 | chitinase Cht-3 | 37 | TC85888 | D16223* |
| 16 | PRO0151 | WSI18 | 38 | TC84300 | AP003023 |
| 17 | PRO0169 | aquaporine | 39 | TC89687 | AP005108 |
| 18 | PRO0170 | High mobility group protein | 40 | TC89846 | AP004004 |
| 19 | PRO0171 | reversibly glycosylated protein RGP1 | 41 | TC82935 | AC090874 |
| 20 | PRO0173 | cytosolic MDH | 42 | TC82977 | AC037425 |
| 21 | PRO0175 | RAB21 | 43 | TC83646 | Y00842* |
| 22 | PRO0177 | Cdc2-1 | 44 | TC90619 | AP004765 |

Identification and Isolation of the Promoter Regions of Rice Genes

Starting from the sequence information of the genes and their location in the rice genome, the promoter regions of these genes were isolated as the DNA region spanning about 1.2 kb upstream of the translation initiation codon (i.e. first ATG), which codon was excluded. When an intervening sequence such as an intron, was present in the 5' untranslated region of the gene, the isolated DNA region was taken as the region spanning about 1.2 kb plus the length of that intervening sequence. The promoter regions were isolated from genomic DNA of *Oryza sativa Japonica* or exceptionally from *Oryza sativa Indica* via PCR using specific primers. These specific primers comprise AttB recombination sites, suitable for recombination cloning of the isolated promoter region These specific primers are herein represented as SEQ ID NO 45 to 88 and are listed in Table 2. Conditions for PCR were as follows: 1 cycle of 2 min at 94° C., 35 cycles of 1 min at 94° C., 1 min at 58° C. and 2 min at 68° C., and 1 cycle of 5 min at 68° C. The length of the expected PCR fragment is also indicated in Table 2. The corresponding PCR fragment was purified from the PCR reaction mix via gele electrophoresis and subsequent purification using Zymoclean Gel DNA Recovery Kit (Zymo Research, Orange, Calif.).

TABLE 2

Overview of the primers used to isolate the rice promoters of the present invention and the length of the rice promoter regions.

| Promoter SEQ ID NO | Promoter number | Prom length | Primer forward SEQ ID NO | Primer forward | Primer reverse SEQ ID NO | Primer reverse |
|---|---|---|---|---|---|---|
| 1 | PRO0110 | 1264 | 45 | prm3780 | 67 | prm3781 |
| 2 | PRO0005 | 1215 | 46 | prm2768 | 68 | prm2769 |
| 3 | PRO0009 | 1038 | 47 | prm2420 | 69 | prm2421 |
| 4 | PRO0058 | 1301 | 48 | prm2853 | 70 | prm2854 |
| 5 | PRO0061 | 1243 | 49 | prm2426 | 71 | prm2427 |
| 6 | PRO0063 | 1019 | 50 | prm2855 | 72 | prm2856 |
| 7 | PRO0081 | 1212 | 51 | prm3025 | 73 | prm3026 |
| 8 | PRO0091 | 1052 | 52 | prm3029 | 74 | prm3030 |
| 9 | PRO0095 | 1216 | 53 | prm3061 | 75 | prm3062 |
| 10 | PRO0111 | 1237 | 54 | prm3031 | 76 | prm3032 |
| 11 | PRO0116 | 1100 | 55 | prm3051 | 77 | prm3052 |
| 12 | PRO0117 | 1216 | 56 | prm3592 | 78 | prm3049 |
| 13 | PRO0122 | 1210 | 57 | prm5131 | 79 | prm2195 |
| 14 | PRO0123 | 123 | 58 | prm3782 | 80 | prm2197 |
| 15 | PRO0133 | 1808 | 59 | prm2844 | 81 | prm2845 |
| 16 | PRO0151 | 1828 | 60 | prm2973 | 82 | prm2974 |
| 17 | PRO0169 | 1267 | 61 | prm3770 | 83 | prm3771 |
| 18 | PRO0170 | 1130 | 62 | prm3772 | 84 | prm3773 |
| 19 | PRO0171 | 1230 | 63 | prm3774 | 85 | prm3775 |
| 20 | PRO0173 | 1234 | 64 | prm3776 | 86 | prm3777 |
| 21 | PRO0175 | 1553 | 65 | prm3800 | 87 | prm3801 |
| 22 | PRO0177 | 1087 | 66 | prm5135 | 88 | prm5136 |

Example 2

Cloning of Promoter-GUS Reporter Vectors for Plant Transformation

The purified PCR fragments of Example 1, corresponding to the promoter regions of the present invention, were cloned into the pDONR201 entry plasmid of the Gateway™ system (Life Technologies) using the "BP recombination reaction".

The identity and base pair composition of the cloned insert was confirmed by sequencing and additionally, the resulting plasmid was tested via restriction digests.

Figure 2:
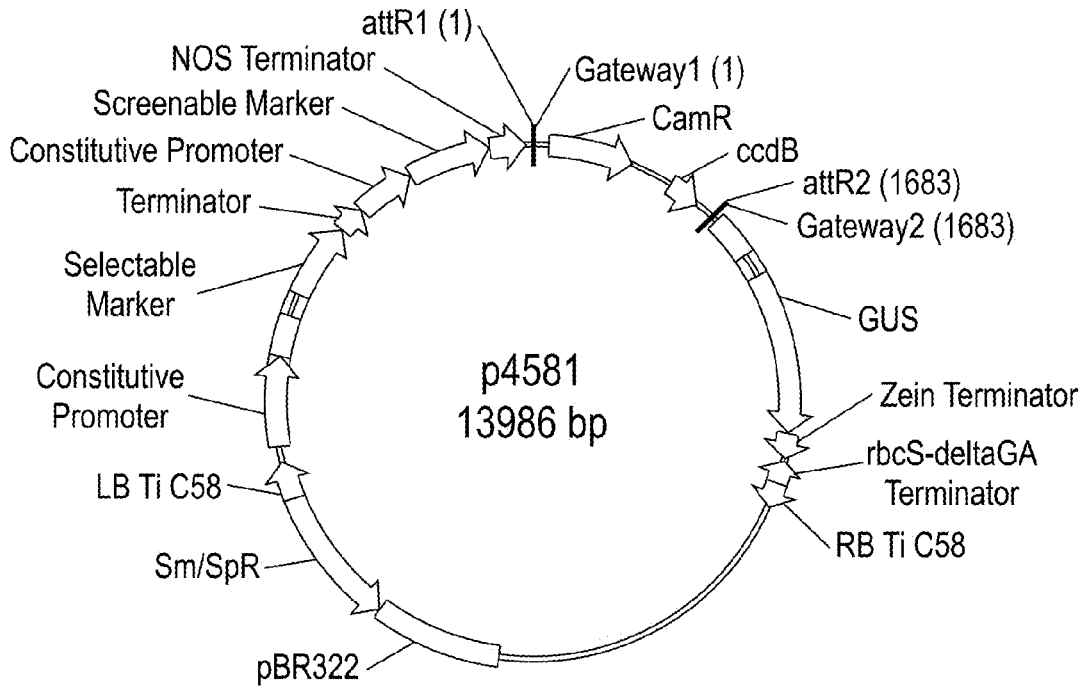
Figure 3:
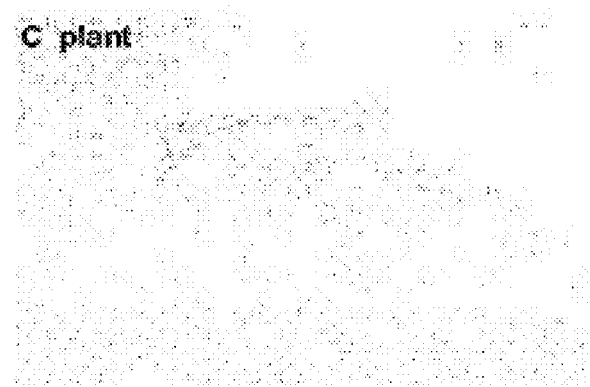
FIG. 3 shows the expression pattern of PRO0110 (RCc3, SEQ ID NO 1). GUS staining is visible in roots.
Figure 4:
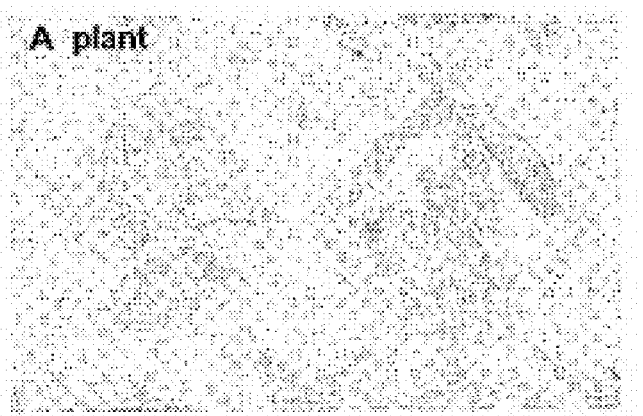
FIG. 4 shows the expression pattern of PRO0005 (putative beta-amylase, SEQ ID NO 2). GUS staining is visible in seeds, more specifically in the embryo or in the scutellum of the embryo.
Figure 5:
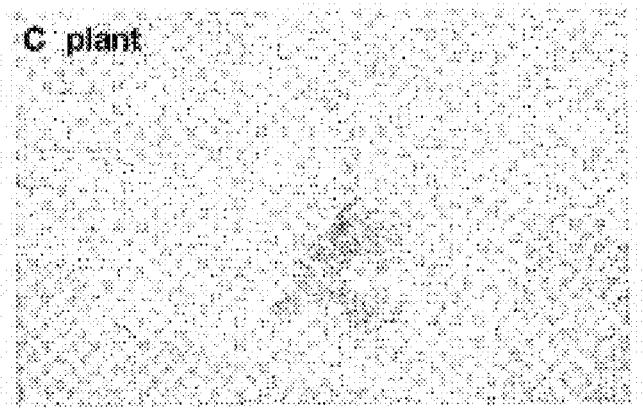
FIG. 5 shows the expression pattern of PRO0009 (putative cellulose synthetase, SEQ ID NO 3). GUS staining is visible in roots.
Figure 6:
FIG. 6 shows the expression pattern of PRO0058 (proteinase inhibitor Rgpi9, SEQ ID NO 4). GUS staining is visible in the seeds.
Figure 7:
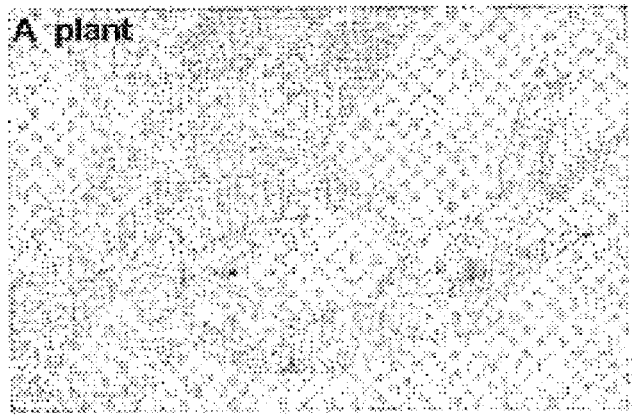
FIG. 7 shows the expression pattern of PRO0061 (beta expansine EXPB9, SEQ ID NO 5). GUS staining is visible in young flowers of A plants (A) and in other young expanding tissues of B plants (B) and C plants (C).
Figure 7:
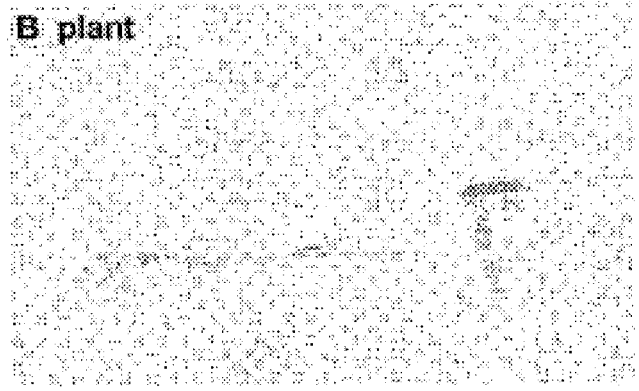
Figure 7:
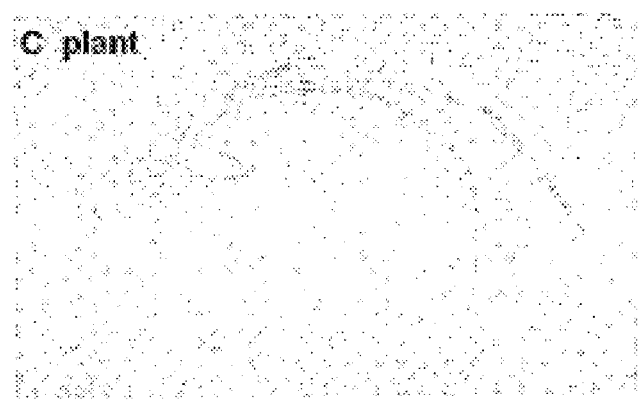
Figure 8:
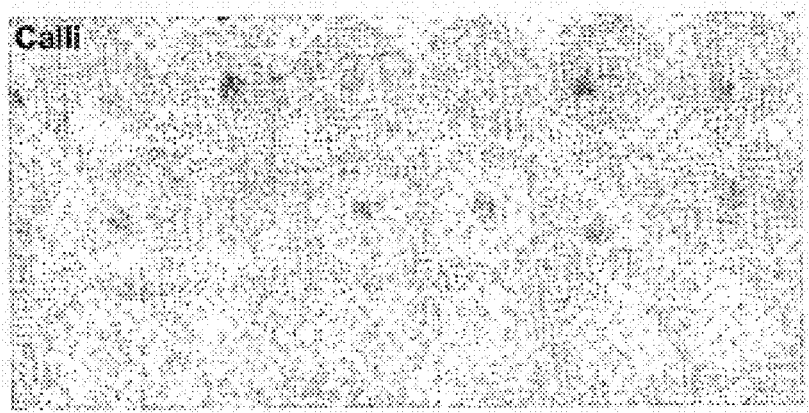
FIG. 8 shows the expression pattern of PRO0063 (putative structural protein, SEQ ID NO 6). GUS staining is visible in young tissues, for example in the calli (A) or old leaves, young leaves and seeds of "A plants" (B).
Figure 9:
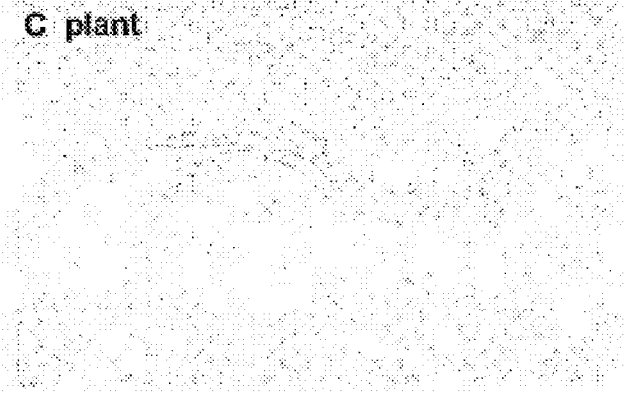
FIG. 9 shows the expression pattern of PRO0081 (putative caffeoyl-CoA 3-O-methyltransferase, SEQ ID NO 7). GUS staining is visible in young tissues, particularly of the shoot.
Figure 10:
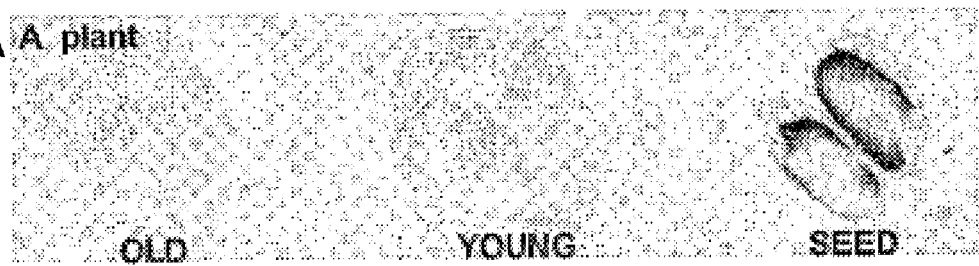
FIG. 10 shows the expression pattern of PRO0091 (prolamine RP5, SEQ ID NO 8). GUS staining is visible in seeds (A), particularly in the endosperm, and in meristem (B).
Figure 11:
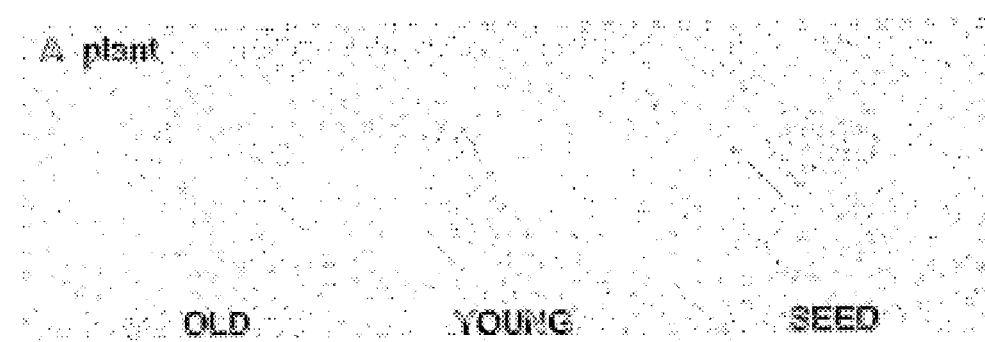
FIG. 11 shows the expression pattern of PRO0095 (putative amino peptidase, SEQ ID NO 9). GUS staining is visible in seeds, more particularly in the embryo.
Figure 12:
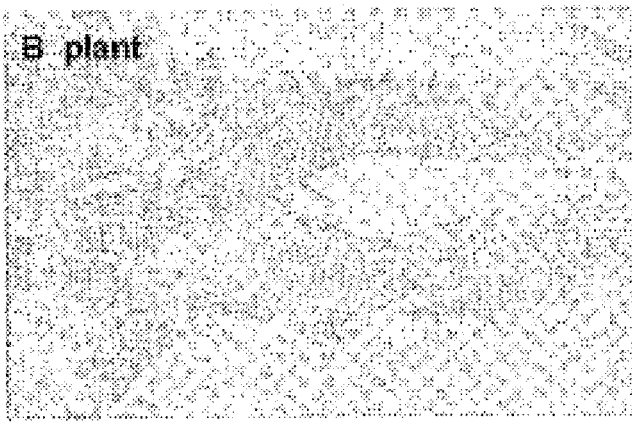
FIG. 12 shows the expression pattern of PRO0111 (uclacyanin 3-like protein, SEQ ID NO 10). GUS staining is visible in roots and in meristem.
Figure 13:
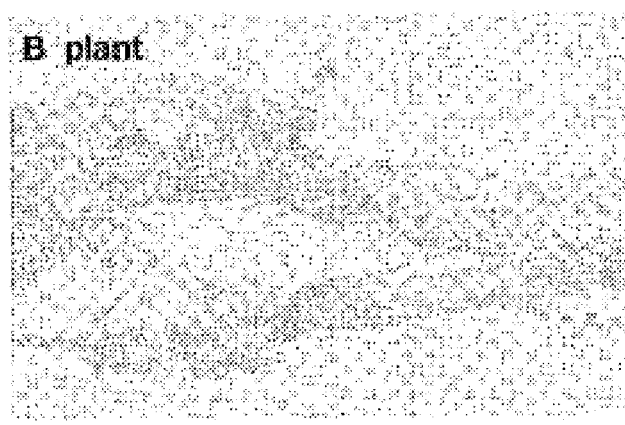
FIG. 13 shows the expression pattern of PRO0116 (26S proteasome regulatory particle non-ATPase subunit 11, SEQ ID NO 11). GUS staining is weakly visible in the whole plant (weak constitutive) and is particularly visible in meristem.
Figure 14:
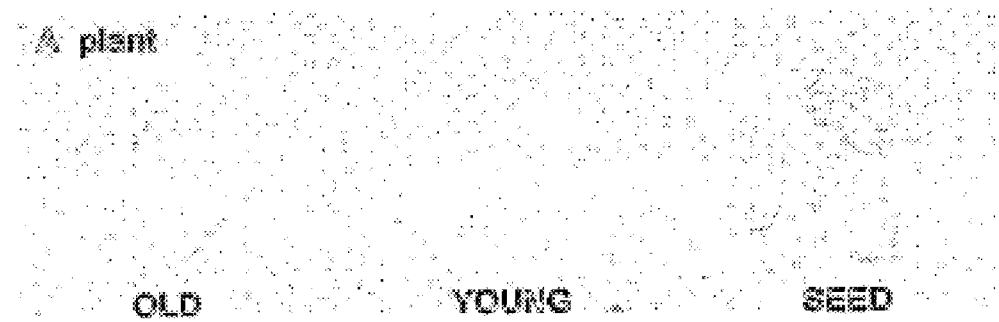
FIG. 14 shows the expression pattern of PRO0117 (putative 40S ribosomal protein, SEQ ID NO 12). GUS staining is visible in the seeds, more particularly in the endosperm.
Figure 15:
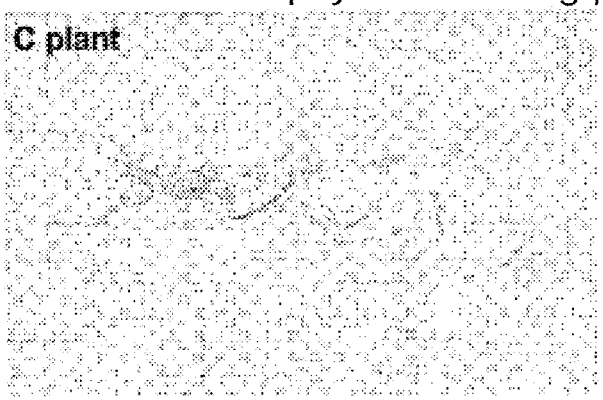
FIG. 15 shows the expression pattern of PRO0122 (chlorophyll a/b-binding protein presursor (Cab27), SEQ ID NO 13). GUS staining is visible in the shoot.
Figure 16:
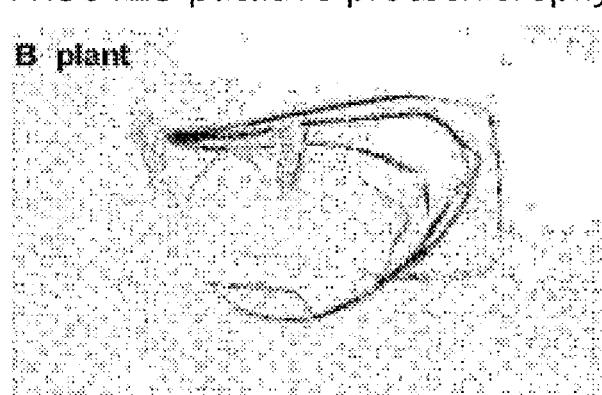
FIG. 16 shows the expression pattern of PRO0123 (putative protochlorophyllide reductase, SEQ ID NO 14). GUS staining is visible in the shoot (above-ground tissues).
Figure 17:
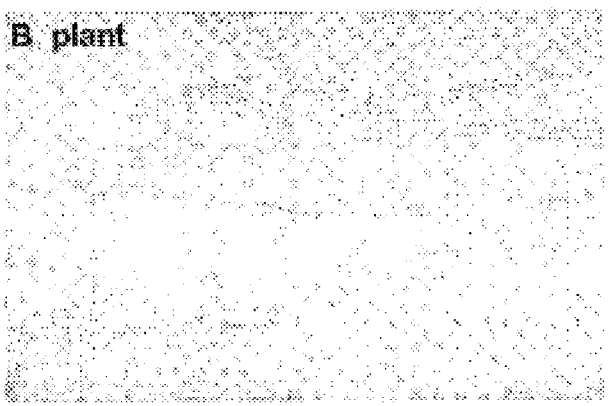
FIG. 17 shows the expression pattern of PRO0133 (chitinase Cht-3, SEQ ID NO 15). GUS staining is visible in the roots and meristem.
Figure 18:
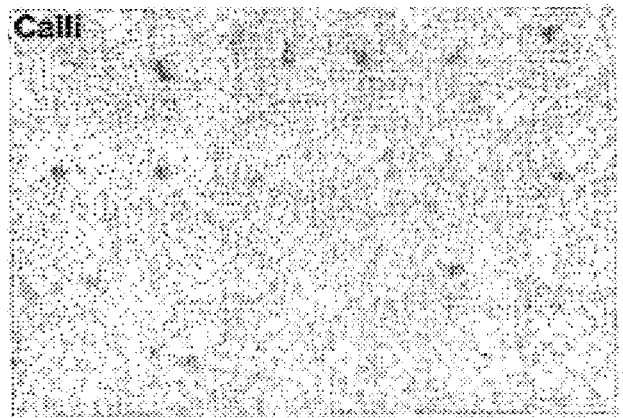
FIG. 18 shows the expression pattern of PRO0151 (WSI18, SEQ ID NO 16). GUS staining is visible in the calli and upper plant parts (A) as well as in the aleurone layer and embryo (B).
Figure 18:
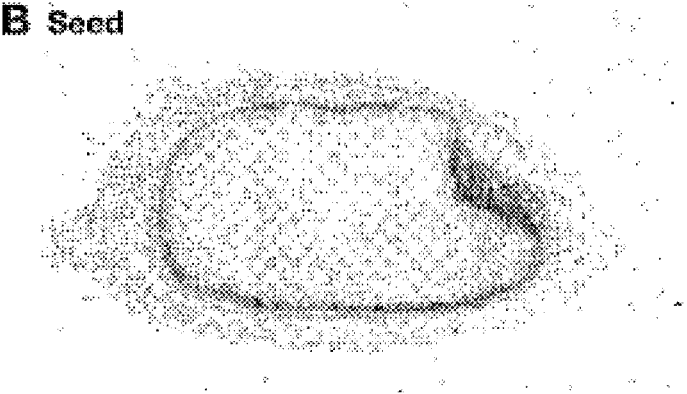
Figure 19:
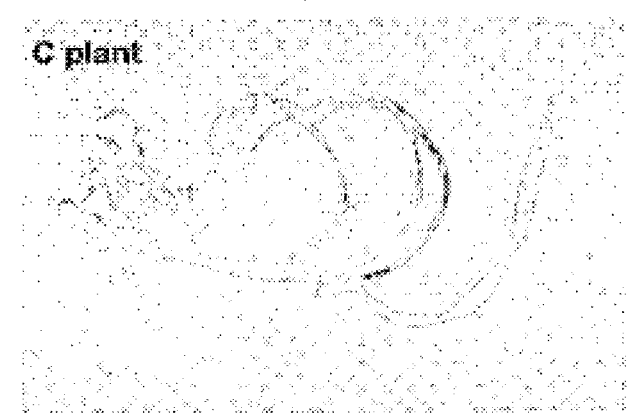
FIG. 19 shows the expression pattern of PRO0169 (aquaporine, SEQ ID NO 17). GUS staining is visible in the whole plant (constitutive expression).
Figure 20:
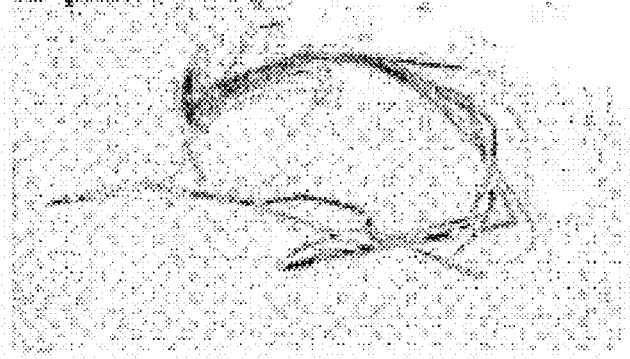
FIG. 20 shows the expression pattern of PRO0170 (High mobility group protein, SEQ ID NO 18). GUS staining is strongly visible in the whole plant as is illustrated by the "B plants" (A), and various tissues such as old leaves, young leaves and seeds (B) and calli (C) (constitutive expression).
Figure 20:
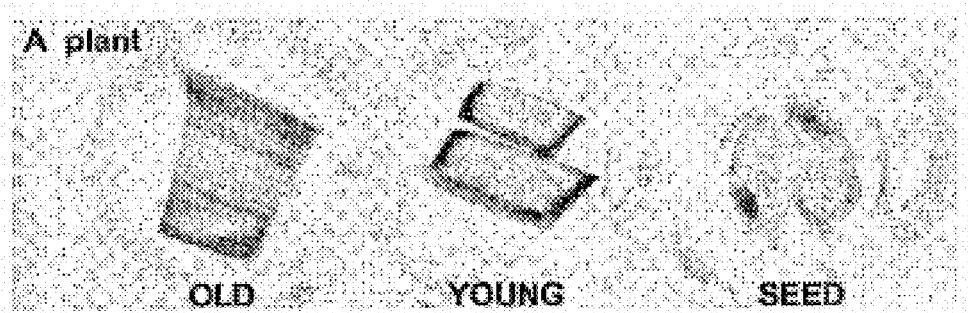
Figure 20:
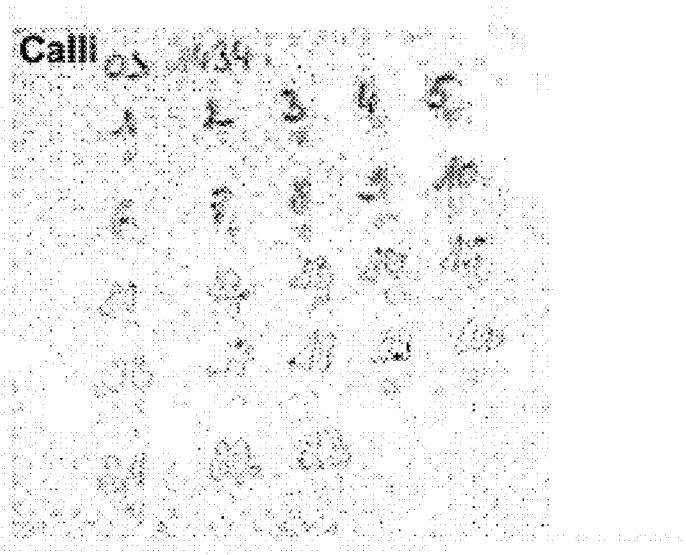
Figure 21:
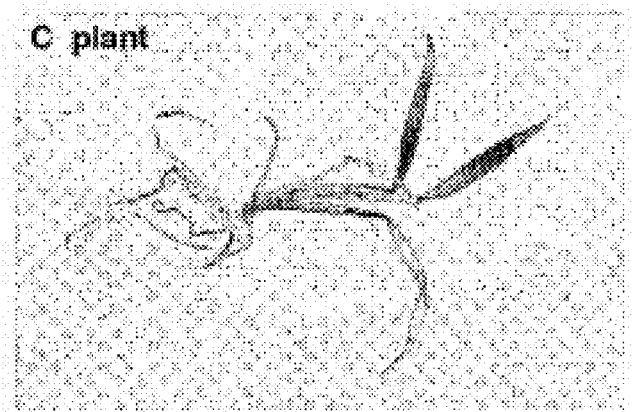
FIG. 21 shows the expression pattern of PRO0171 (reversibly glycosylated protein RGP1, SEQ ID NO 19). GUS staining is visible in all plant parts (constitutive expression).
Figure 22:
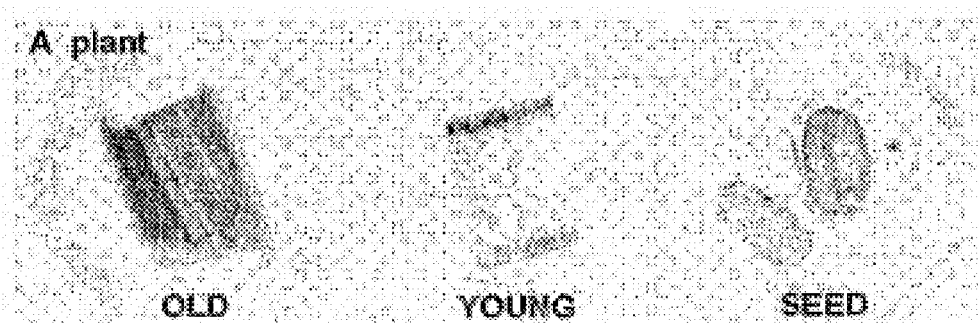
FIG. 22 shows the expression pattern of PRO0173 (cytosolic MDH, SEQ ID NO 20). GUS staining is visible in all plant parts and particularly in the shoot (above-ground tissues) and seeds.
Figure 23:
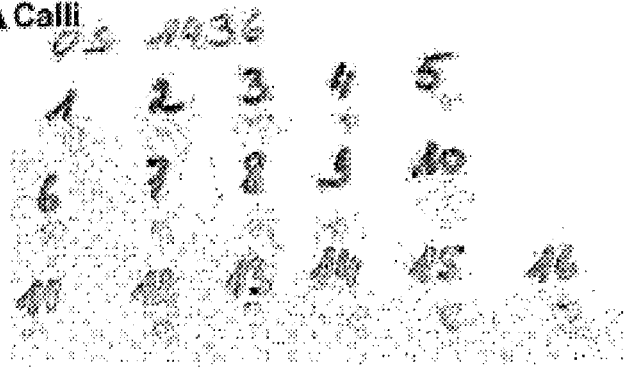
FIG. 23 shows the expression pattern of PRO0175 (RAB21, SEQ ID NO 21). GUS staining is weakly visible in calli (A), meristems and young leaves, and is strongly visible in developing and maturing seeds (B) more particularly in the embryo.
Figure 23:
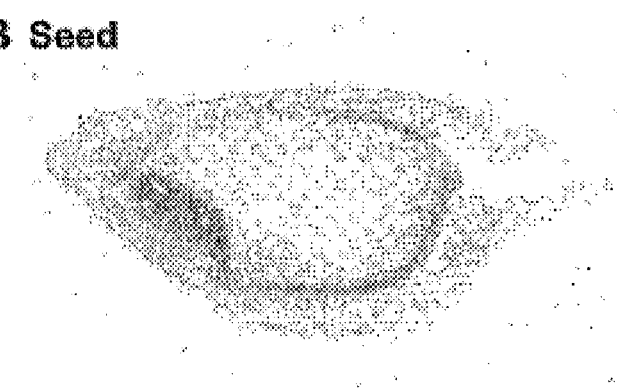
Figure 24:
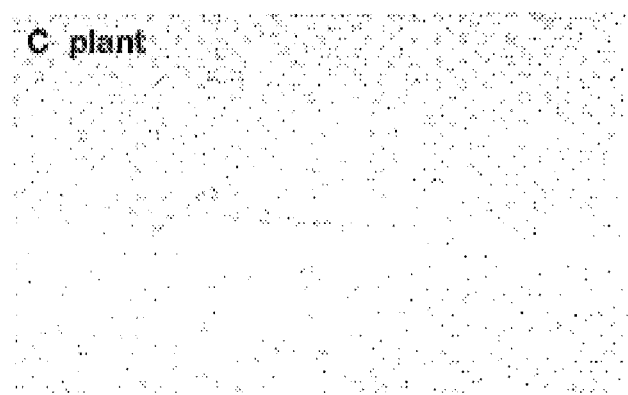
FIG. 24 shows the expression pattern of PRO0177 (Cdc2-1, SEQ ID NO 22). GUS staining is weakly visible in meristem and in leaf sheets.

In order to clone each of the promoters of the present invention in front of a reporter gene, each entry clone of Example 1 was subsequently used in an "LR recombination reaction" (Gateway TM) with the destination vector p4581. This destination vector was designed to operably link each promoter of the present invention to the *Escherichia coli* beta-glucuronidase (GUS) gene via the substitution of the Gateway recombination cassette in front of the GUS gene. Furthermore this destination vector is suitable for transformation of plants and comprises within the T-DNA left and right borders the resulting promoter-GUS cassette and selectable marker and screenable marker cassettes (see FIG. 2). The resulting reporter vectors, comprising a promoter of the present invention operably linked to GUS, are subsequently transformed into *Agrobacterium* strain LBA4044 and subsequently into rice plants using standard transformation techniques.

Example 3

Expression Patterns of the Promoter-GUS Reporter Cassette in Plants

Growth and Harvest of Transgenic Plants or Plant Parts at Various Stages (C Plants, B Plants and A Plants)

For each promoter-GUS reporter construct, 3 T0 transgenic rice plants were generated from transformed cells. Plant growth was performed under normal conditions. The first transgenic plant was sacrificed for GUS staining when it had reached a size of about 5 cm, which plant is named herein "C plant". The second transgenic plant was sacrificed for GUS staining when it had reached a size of about 10 cm, which plant is named herein "B plant". The third transgenic plant was kept for seed production and is named herein "A plant". GUS staining was performed on complete C and B plants. On A plants, GUS staining was performed on leaf pieces, flowers and section of seeds at various developmental stages. A plants were allowed to set seed, which seeds were used after harvest for confirmation of the expression pattern in T1 plants.

GUS Staining

The sacrificed plants or plant parts were covered with 90% ice-cold acetone and incubated for 30 min at 4° C. After 3 washes of 5 min with Tris buffer [15.76 g Trizma HCl (Sigma T3253)+2,922 g NaCl in 1 l bidi, adjusted to pH 7.0 with NaOH], the material was covered by a Tris/ferricyanate/X-Gluc solution [9.8 ml Tris buffer+0.2 ml ferricyanate stock (0.33 g Potassium ferricyanate (Sigma P3667) in 10 ml Tris buffer)+0.2 ml X-Gluc stock (26.1 mg X-Gluc (Europa Bioproducts ML 113A) in 500 µl DMSO)]. Vacuum infiltration was applied for 15 to 30 minutes. The plants or plant parts were incubated for up to 16 hours at 37° C. until development of blue colour was visible. The samples were washed 3 times for 5 minutes with Tris buffer. Chlorophyll was extracted in ethanol series of 50%, 70% and 90% (each for 30 minutes).

Expression Patterns of the Promoters of the Present Invention

The expression patterns of the rice promoters of the present invention are summarized in Table 3.

TABLE 3 expression patterns of the rice promoters of the present invention

| PRO SEQ ID NO | Promoter number | Promoter name | Expression pattern |
|---|---|---|---|
| 1 | PRO0110 | RCc3 | strong root |
| 2 | PRO0005 | putative beta-amylase | Embryo (scutellum) |
| 3 | PRO0009 | putative cellulose synthase | weak in roots |
| 4 | PRO0058 | proteinase inhibitor Rgpi9 | seed |
| 5 | PRO0061 | beta expansine EXPB9 | weak in young tissues |
| 6 | PRO0063 | structural protein | young tissues + calli + embryo |
| 7 | PRO0081 | putative caffeoyl-CoA 3-O-methyltransferase | shoot |
| 8 | PRO0091 | prolamine RP5 | meristem + strong in endosperm |
| 9 | PRO0095 | putative methionine aminopeptidase | embryo |
| 10 | PRO0111 | uclacyanin 3-like protein | weak meristem |
| 11 | PRO0116 | 26S proteasome reg. particle non-ATPase s.u. 11 | weak meristem |
| 12 | PRO0117 | putative 40S ribosomal protein | weak in endosperm |
| 13 | PRO0122 | chlorophyll a/b-binding protein presursor (Cab27) | weak in shoot |
| 14 | PRO0123 | putative protochlorophyllide reductase | strong shoot specific |
| 15 | PRO0133 | chitinase Cht-3 | weak meristem specific |
| 16 | PRO0151 | WSI18 | Calli + shoot + strong embryo |
| 17 | PRO0169 | aquaporine | medium constitutive |
| 18 | PRO0170 | High mobility group protein | strong constitutive |
| 19 | PRO0171 | reversibly glycosylated protein RGP1 | weak constitutive |
| 20 | PRO0173 | cytosolic MDH | Shoot and seed |
| 21 | PRO0175 | RAB21 | embryo |
| 22 | PRO0177 | Cdc2-1 | weak in meristem + strong seed |

The following paragraphs describe the observed expression patterns of the promoters of the present invention in more detail. The observations are based on the visual inspection of the GUS stained tissues as described above. It is to be understood that for some promoters expression may be weak and that expression in certain tissues may only be visible with very sensitive detection methods.

PRO0110—SEQ ID NO 1-RCc3

1 construct (OS1432), which is a reporter vector as described in Example 2 comprising PRO0110 was investigated. 25 calli, 14 C, 21 B plants and 21 A plants were analysed. There was no expression visible in calli, but strong expression in roots of C plants (93%) and of B plants (81%) was observed. No expression in the shoots of A plants was observed. Therefore the RCc3 promoter PRO0110 is suitable for strong expression in roots.

PRO0005—SEQ ID NO 2—Putative Beta-Amylase 1 construct (OS1365) was investigated. 28 calli, 24 B plants and 22 A plants were analysed. Occasional expression in calli (7%) was observed as well as occasional weak expression in roots (4%) and shoots (12%) of B plants, expression in the scutellum of embryos of A plants (43%) and occasional expression in leaves (5%) of A plants. This promoter is therefore suitable for expression in embryo, more preferably in the scutellum of the embryo. This region of the embryo is also referred to as the transfer layer of the embryo. This promoter may have some leakiness in other tissues.

PRO0009—SEQ ID NO 3—Putative Cellulose Synthase 1 construct (OS1461) was investigated. 20 calli, 20 C, 20 B plants and 20 A plants were analysed. Occasional expression in calli (20%) was observed as well as weak expression in roots (55%) of C plants, occasional expression in young leaves (10%) of C plants and weak expression in the roots (25%) of B plants. No expression in leaves of A or B plants was observed. Therefore this promoter is suitable for expression in roots. This promoter may show some leakiness in the leaves.

PRO0058—SEQ ID NO 4—Proteinase Inhibitor Rgpi9

1 construct (OS1370) was investigated. 13 B plants and 12 A plants were analysed. No expression was observed in B plants. In A plants, no expression was observed in the leaves, but there was strong expression in endosperm and embryo (58-42%). Therefore, this promoter PRO0058 is suitable for expression in seeds.

PRO0061—SEQ ID NO 5—Beta Expansine EXPB9

2 constructs (OS1441 and OS1460) were investigated. 20 calli, 32 C, 32 B plants and 32 A plants were analysed. Weak expression was observed in the leaves of C and B plants. In A plants expression in the flowers was observed (44%), more particularly in lemma of young spikelets. It was concluded that the promoter PRO0061 is suitable for expression in young tissue, more preferably in young, developing or expanding tissue, more preferably in green tissue.

PRO0063—SEQ ID NO 6—Putative Structural Protein 1 construct (OS1446) was investigated. 13 calli, 13 C, 13 B plants and 12 A plants were analysed. In calli, weak expression was detected (92%). In C plants, there was no expression in roots and there was weak expression in some leaves (46%). In B plants, there was no expression in roots and weak expression in young tillers (78%) or young leaves (54%), but no expression in old leaves. In A plants, there was occasional expression in young leaves (17%) and expression in embryo and scutellum (42%). Therefore it was concluded that this promoter is active in the above-ground tissues, such as leaf, stem and seed. These data demonstrate that the promoter is suitable for expression in calli and in the shoot, and for expression in young tissues and seeds.

PRO0081—SEQ ID NO 7—Putative Caffeoyl-CoA 3-O-methyltransferase 1 construct (OS1419) was investigated. 20 calli, 20 C, 20 B plants and 20 A plants were analysed. No expression was observed in Calli. Expression was observed in C plants, more particularly weak expression in root cylinder (40%) and weak expression in young leaves (80%) and in old leaves. Expression was also observed in B plants, more particularly weak expression in roots (25%) and weak expression in young leaves (80%). Expression was also observed in young leaves (50%) of A plants. It was concluded that promoter PRO0081 is suitable for expression in above-ground tissues, preferably in the shoot. This promoter may have some leakage of expression in roots.

PRO0091—SEQ ID NO 8—Prolamine RP5

1 construct (OS1558) was investigated. 12 C, 12 B plants and 12 A plants were analysed. Weak expression was observed in the discrimination centre (50%) of C plants and in the discrimination centre (58%) of B plants. Strong expression was observed in endosperm (55%) of A plants. This promoter was found to be useful for strong expression in the endosperm, with leakiness in meristem, preferably the shoot meristem or discrimination centre.

PRO0095—SEQ ID NO 9—Putative Methionine Aminopeptidase 1 construct (OS1423) was investigated. 16 calli, 14 C, 14 B plants and 16 A plants were analysed. Some expression was observed in root-tips (36%) of C plants and in the embryo (38%) of A plants, but not in endosperm of A plants. It was concluded that PRO0095 is suitable for expression in embryo.

PRO0111—SEQ ID NO 10—Uclacyanin 3-Like Protein 1 construct (OS1421) was investigated. 22 calli, 21 C, 22 B plants and 21 A plants were analysed. Weak expression was observed in the discrimination centre and meristems (77%) of B plants. It was concluded that promoter PRO0111 is suitable for weak expression in the meristem, preferably in shoot meristem or discrimination centre.

PRO0116—SEQ ID NO 11-26S Proteasome Regulatory Particle Non-A TPase Subunit 11

1 construct (OS1679) was investigated. 13 C, 14 B plants and A plants were analysed. Weak expression was observed in meristem/discrimination centre of C plants (38%) and of B plants (71%) and in young leaf sheaths of C plants (77%) and of B plants (21%). It was concluded that promoter PRO0116 is suitable for expression in meristem, preferably in shoot meristem or discrimination centre.

PRO0117—SEQ ID NO 12—Putative 40S Ribosomal Protein 1 construct (OS1425) was investigated. 9 calli, 9 C, 9 B plants and 9 A plants were analysed. Occasional weak expression was observed in roots (22%) and in young leaf blades (44%) of C plants. Expression was mainly observed in endosperm (37%) of A plants. Therefore, promoter PRO117 was found to be suitable for expression in endosperm and may have some leakiness in young leaves.

PRO0122—SEQ ID NO 13—Chlorophyll a/b-Binding Protein Presursor (Cab27)

1 construct (OS1675) was investigated. 38 calli, 38 C, 38 B plants and 15 A plants were analysed. Very weak expression was observed in the discrimination centre and young leaf sheaths of C plants. It was concluded that this promoter PRO0122 is suitable for weak expression in shoots.

PRO0123—SEQ ID NO 14—Putative Protochlorophyllide Reductase 1 construct (OS1433) was investigated. 21 calli, 18 C, 19 B plants and 18 A plants were analysed. Strong expression was observed in shoots (33-68%) of C plants and B plants (63-

79%). In B plants there was also occasional expression in roots. In A plants, again strong expression in young leaves (73%) was observed, as well as occasional expression in old leaves (39%). It was concluded that this promoter is suitable for strong expression in shoots, preferably in leaves.

PRO0133—SEQ ID NO 15—chitinase Cht-3

1 construct (OS1687) was investigated. 15 calli, 12 C, 16 B plants and 12 A plants were analysed. Weak expression was observed in calli (66%) and in the discrimination centre/meristem (50%) of B plants. It was concluded that promoter PRO0133 is suitable for weak expression in meristem, preferably in shoot meristem or discrimination centre.

PRO0151—SEQ ID NO 16—WSI18

1 construct (OS1458) was investigated. 22 calli, 16 C, 16 B plants and 13 A plants were analysed. Strong expression was observed in calli (91%) and weak expression in shoots of C plants (62%). In A plants there was very strong expression in the aleurone layer and in the embryo (46%). It was concluded that promoter PRO0151 is suitable for strong expression in calli and in seeds, more particularly in the aleurone layer and in the embryo of the seeds.

PRO0169—SEQ ID NO 17—Aquaporine 1 construct (OS1911) was investigated. 11 calli, 10 C plants, B plants and A plants were analysed. Some expression (55%) was observed in calli and in roots (30%) of C plants. Furthermore, good expression was observed in shoot tissues (80%) of C plants and in young leaves of B plants. It was concluded that this promoter is suitable for constitutive expression, preferably constitutive in young plants.

PRO170—SEQ ID NO 18—HIGH MOBILITY GROUP PROTEIN 1 construct (OS1434) was investigated. 23 calli, 21 C, 21 B plants and 14 A plants were analysed. Expression was observed in calli (52%) and in roots (51%) of C plants. Moreover, strong expression was observed in young leaves (81%) of C plants, in roots (86%) of B plants and in young leaves (86%) of B plants. In A plants there was strong expression in young leaves (75%), old leaves (43%), embryo and aleurone but a weaker expression in endosperm (82%). It was concluded that promoter PRO170 is suitable for strong constitutive expression.

PRO0171—SEQ ID NO 19—Reversibly Glycosylated Protein RGP1

1 construct (OS1762) was investigated. 18 calli, 11 C and 13 B plants were analysed. Strong expression was observed in calli (44%) and in all tissues (27%) of C plants. In all tissues of B plants (16%), expression was somewhat weaker but most pronounced the in discrimination centres (46%). It was concluded that promoter PRO0171 is suitable for constitutive expression.

PRO0173—SEQ ID NO 20—Cytosolic MDH 1 construct (OS1435) was investigated. 17 calli, 17 C, 17 B plants and 15 A plants were analysed. Occasional expression (12%) was observed in calli and weak expression was observed in upper parts (24-69%) of C plants as well as in young leaves (41%) of B plants. In A plants, expression in leaves (33%) was observed and strong expression in seeds (38%), but not in the root. It was concluded that the promoter PRO0173 is suitable for expression in above-ground tissues especially for constitutive expression in the shoot and especially in the seeds.

PRO0175—SEQ ID NO 21—RAB21

1 construct (OS1436) was investigated. 16 calli, 12 C, 15 B plants and 15 A plants were analysed. Expression was observed in some calli (31%), in the discrimination centres (42%) of C plants and in young leaves (25-58%) of C plants and A plants (15%). Furthermore, very strong expression was observed in aleurone and embryo (60%) of a plant. It was concluded that promoter PRO0175 is suitable for strong expression in calli and in seeds, more particularly in developing/maturing seeds, more particularly in the aleurone layer and in the embryo of the seeds.

PRO0177—SEQ ID NO 22-Cdc2-1

1 construct (OS1436) was investigated. 16 calli, 12 C, 15 B plants and 15 A plants were analysed. Expression was observed in some of the calli (31%), in the discrimination centre (42%) of C plants, in young leaves (25-58%) of C plants and occasionally in young leaves (15%) of A plants. Moreover, very strong expression was observed in aleurone and embryo (60%) of seeds from A plants. It was concluded that this promoter is suitable for specific expression in seeds, more particularly in developing/maturing seeds.

Example 4

Stability of the Expression Patterns of the Promoters of the Present Invention in Further Generations The above-mentioned analyses were performed on T0 plants originating from the transformed tissues. The stability of promoter activity in the next generations or progeny plants of the original T0 plant, the so-called T1 and T2 plants, was evaluated as follows. The T0 plant transformed with the reporter constructs as mentioned in the above paragraphs of Example 2, were grown until maturity (A plants), of which the seeds (T1 seeds) were harvested and sown to generate progeny T1 plants. These plants were analysed as described above in Example 3 and the A T1 plants were allowed to reach maturity and to set T2 seeds.

The expression pattern of the promoters of the present invention was studied in T0 plants, T1 seeds, T1 plants and T2 seeds and in all the tissues (including seeds and seed tissues) as described in Example 3. The specific expression patterns as reported from the T0 and T1 seeds and described in Example 3 were confirmed in the following T1 generation and T2 seeds. It is concluded that the expression pattern of the promoters of the present are stably inherited in plants of subsequent generations.

Example 5

Stability of Expression Patterns of the Promoters of the Present Invention in Other Plants The above-mentioned plant analyses were performed on rice plants. This choice was based on the practical consideration that plant genetic engineering is most profitable for crop plants. Also in other crop plants, such as for example *Zea Mays*, the reporter constructs comprising the promoters according to the present invention are introduced and transformed plant are evaluated as described hereinabove. The expression patterns of the promoters according to the present invention are conserved among plants. Therefore, the promoters according to the present invention are also suitable for driving and/or regulating expression of an operably linked nucleic acid in monocots, such as corn.

For many other purposes such as research and horticulture, (small) herbs are being genetically modified, which involves the use of promoters. Therefore the reporter constructs comprising the promoters according to the present invention are introduced into other plants species such as for example *Arabidopsis thaliana* and transformed plants are evaluated as described hereinabove. The expression patterns of the promoters according to the present invention are conserved among plants. Therefore, the promoters according to the present invention are also suitable for driving and/or regulating expression of an operably linked nucleic acid in other plant species such as for example dicots, such as *Arabidopsis*.

We claim:

1. A method for driving leaf-preferable expression of a nucleic acid in a plant comprising introducing into a cell of a monocot or dicot plant a genetic construct comprising (a) an isolated promoter comprising an isolated nucleic acid comprising the sequence of SEQ ID NO: 14; and (b) a heterologous nucleic acid sequence operably linked to said isolated promoter; and optionally (c) a 3' transcription terminator, and testing and selecting a transgenic plant with leaf-preferable expression of said heterologous nucleic acid sequence.

2. The method according to claim 1, wherein after said introducing step and prior to said testing and selecting step, said cell of a monocot or dicot plant is cultivated under conditions promoting plant growth.

3. The method according to claim 2, wherein said cell of a monocot or dicot plant is selected from the group consisting of rice, maize, wheat, barley, millet, oats, rye, sorghum, soybean, sunflower, canola, sugarcane, alfalfa, bean, pea, flax, lupinus, rapeseed, tobacco, tomato, potato, squash, papaya, poplar and cotton.

* * * * *

SEQUENCE LISTING

<160> NUMBER OF SEQ ID NOS: 88

<210> SEQ ID NO 1
<211> LENGTH: 1264
<212> TYPE: DNA
<213> ORGANISM: Oryza sativa
<220> FEATURE:
<221> NAME/KEY: misc_feature
<223> OTHER INFORMATION: PRO0110 - RCc3

<400> SEQUENCE: 1

```
tcgacgctac tcaagtggtg ggaggccacc gcatgttcca acgaagcgcc aaagaaagcc        60
ttgcagactc taatgctatt agtcgcctag gatatttgga atgaaaggaa ccgcagagtt       120
tttcagcacc aagagcttcc ggtggctagt ctgatagcca aaattaagga ggatgccaaa       180
acatgggtct tggcgggcgc gaaacacctt gataggtggc ttacctttta acatgttcgg       240
gccaaaggcc ttgagacggt aaagttttct atttgcgctt gcgcatgtac aattttattc       300
ctctattcaa tgaaattggt ggctcactgg ttcattaaaa aaaaagaat ctagcctgtt        360
cgggaagaag aggattttgt tcgtgagaga gagagagaga gagagagaga gagagagaga       420
gaaggaggag gaggattttc aggcttcgca ttgcccaacc tctgcttctg ttggcccaag       480
aagaatccca ggcgcccatg ggctggcagt ttaccacgga cctacctagc ctaccttagc       540
tatctaagcg ggccgaccta gtagccacgt gcctagtgta gattaaagtt gccgggccag       600
caggaagcca cgctgcaatg gcatcttccc ctgtccttcg cgtacgtgaa aacaaaccca       660
ggtaagctta gaatcttctt gcccgttgga ctgggacacc caccaatccc accatgcccc       720
gatattcctc cggtctcggt tcatgtgatg tcctctcttg tgtgatcacg gagcaagcat       780
tcttaaacgg caaaagaaaa tcaccaactt gctcacgcag tcacgctgca ccgcgcgaag       840
cgacgcccga taggccaaga tcgcgagata aaataacaac caatgatcat aaggaaacaa       900
gcccgcgatg tgtcgtgtgc agcaatcttg gtcatttgcg ggatcgagtg cttcacagct       960
aaccaaatat tcggccgatg atttaacaca ttatcagcgt agatgtacgt acgatttgtt      1020
aattaatcta cgagccttgc tagggcaggt gttctgccag ccaatccaga tcgccctcgt      1080
atgcacgctc acatgatggc agggcagggt tcacatgagc tctaacggtc gattaattaa      1140
tccccggggct cgactataaa tacctcccta atcccatgat caaaaccatc tcaagcagcc      1200
taatcatctc cagctgatca agagctctta attagctagc tagtgattag ctgcgcttgt      1260
gatc                                                                  1264
```

<210> SEQ ID NO 2
<211> LENGTH: 1215
<212> TYPE: DNA
<213> ORGANISM: Oryza sativa
<220> FEATURE:
<221> NAME/KEY: misc_feature
<223> OTHER INFORMATION: PRO0005 - putative beta-amylase

<400> SEQUENCE: 2

```
cccgatttag tagaccacat tttggcatca aaccaaaata gaccctctcc cagaatttgt        60
aaatggcttt gtggttcgtg atatcactga acctgctggg tgaataaagt aaaaaaaaaa       120
acccataaat tggccttctg caagatctcg tcgtcttgcc caaactatag ccttcgatct       180
ttccatcagg accgcatggg gggagagcag gggcaagtat gaaatggagt tcagattcag       240
attctagaac agtctgaaca tgcgacgacg acgatggcga tgtatctgaa caatctggtc       300
ctctcccctct cctcccgggc gggcttccac gcggctgagt ttcaggctcc caatctgcag       360
```

```
ctcctcccag aaccttactc tgattgattg gttcatcgtt tccatggctc caatgaatgc    420
aacgtgttgt tcagattttc tgaatcttgt tctcaatccg gagtacgtgc tgtagcagca    480
gcaatctgtc cctgatctga aattttaga cactcgtaga ttcgctgatc aatcattccg    540
tcccttcgag tggtctagat tgagcttaat catcctgcta ctcgaatcaa atcttcagca    600
agtgagagct agataattca gaagaaatca acatattctt cgcgaaaaaa agaaataacc    660
gatgaaacca cggtaattag gttcttcgaa tcaccgggag agtaggaaaa aacgagctaa    720
aatcccacat aggaggaaac ggttaaaaac ggccactccg cgtctccgcc gcgagactag    780
ctctcgccca tccacgtagc ccaatccaca accgccacgt gctccgacaa tcccgcccgt    840
ccatcgccgc ggccccggcc tcatctcgac cactcgtttc ctcccttcac accagccacg    900
tggcactctc tcgagagctc ccgcccgcct atataaactt gttcgcgctc ggctcctcct    960
cctcatcgac ctccaccoca cattgaataa ttatttttaa taattttagt ttttttttg    1020 gctttagata tattcccaat ccccaacctc ccaataatcc gatctctccc agttctgttc   1080
ggatcaaggc tgtgtcgatc gcaaaaaaga aaaaaaaaac aatttccttt tggggtggtt   1140
catctgttga tcacttcttt gtttcccgcg ttttgttggg gattcgattt tcgggttaag   1200
attttctaca cgacc                                                    1215

<210> SEQ ID NO 3
<211> LENGTH: 1038
<212> TYPE: DNA
<213> ORGANISM: Oryza sativa
<220> FEATURE:
<221> NAME/KEY: misc_feature
<223> OTHER INFORMATION: PRO0009 - putative cellulose synthase

<400> SEQUENCE: 3
gccatcgagt ggtgtgccga taccggcgcc tgttctttac agcctcagct agtgttgttg     60
tccgaggcaa ttttccgac ctattgtgtt gctttcctct ctgatagctt atggtaaaag    120
atacaaagat gttgaggagt ttgtacgcca cttaattttg ctcgtaacat acattgacaa    180
tcaagaggag ccatggcatt gcgatctgct tacacggcat attcttactg gatggtgtac    240
actacttacc ctttttaatg caagcatcaa tccattgctt ttctcactgc acacctgatt    300
cgtactgaaa acgtgaaaca taaaaaaaaa acaaaaatct agctgatgtt ggctctcggg    360
gcctcgagtc tagtttgtcc tagatggcta acctgatatg tgttggtcac gctcacgttt    420
gaaccgagaa agagtgtgtg tgtgtgtgtg tcggcgtgct gctacaccag agcctccctg    480
aatcgcaatg cgtgttaacg ccagcatcgc aggatttcat ctcacttgac aggttcagat    540
ggccttcctc ctaccgtctg ccatttatac acgcagtgac ttaacgctta cacgagccgg    600
atggcccgga tctcccccct gcaccatctc accagaaaaa cggtgaggcg tcaccgcaac    660
ccacccacca aacacatcca cgtcccttca ccgttggcct tcgattttgc ttcagctgca    720
ctacgacccc tccaacacat ttccctcgcg tctcgttgcg atctcacctt acgacgatct    780
cgttccagca gcagcagcat cggcagcggc ggcttgcttc cgaagcgagc aatgcatggc    840
gcgcgcggcc gcgtgcgtgc gtgccttggc ttgcgctcta atcaaaccgg gacgcccaa    900 ctcacggttg gtgcgggacg ccaccccgcc accttaccgc cccgcctcc ctgcatctga    960 tcatcaacca gctgctatat cacctagcta gccgccgcct cctcctcgcc caccaacgtc   1020
gcttccccgg cacctcac                                                 1038
```

```
<210> SEQ ID NO 4
<211> LENGTH: 1301
<212> TYPE: DNA
<213> ORGANISM: Oryza sativa
<220> FEATURE:
<221> NAME/KEY: misc_feature
<223> OTHER INFORMATION: PRO0058 - proteinase inhibitor Rgpi9

<400> SEQUENCE: 4
tctcttctga agctgaagcc ctgcgaaata ggcctttaaa cgctttaagg ttactggatg      60
atcatatcgg cgtaagaccg gtttaaacat ggtttcgctt tgtgaatcca atgtgagtca     120
cgacgtgaca catggcacgt ccttggagct ttagacatat cgaatctgag cactggagtg     180
gccgagtggg tgagcggcca atccgtttt agacagatcg cactgacacg atgttgatca     240
ttgatactaa taccatttta tcaagcagta gtgttgaaaa aaaaacttat gttctcttca     300
actgtgagat ttcatcccgt ttcaagatga acaagccatg catgtgagat gtgaacagaa     360
ggcagaagac agtggaaaga caggacaaat aagtgaagag ggatcaaatc aatgggcctg     420
acggtttctg aaagttgaca tggaaatcgc cggtgatcac cggtttatac gttatttaaa     480
tctgcgattt ccactttcgt ttgctttcgg ggttccaatt tgagtcacgc acatattctt     540
catcgtgctt tggatctcag caccgtagta acttttggac aaattgcatt cgccgacact     600
aataacatgt tcttttatg ctgctttaca tatactgctt atccacaccc aatcccatgt     660
tcatatatta tgagatggag ggagtaaact ttgttaacag caacatttt tatattaaag     720 catcaactaa ttaaagcaca agatacgcat gttatctcaa taaatcttcc agtgcatgta     780
taaagaagat gtcgccgcta acttagataa ttttttgtgac ttttatcctg ccggcataa     840 ttaattcttc cggaaattaa agctagtttt ttccatattc atcagtacag acaagacagc     900
atagtaagcg aagcatacct gacgtgttag ctcattgtaa ctcgatctgg aacactcgat     960
gctagataca gacagacact cctcgtgatg aacgttagca tttagcaaca tacggtgata    1020
aagcagctgg ggatcgatcc atccatccat cgtctttaca cgtacttacc ttgctaaccg    1080
cactgtcgac tcttgcatgt ttgcatgtaa tccaaatgga ccccacgtgg aacatgctca    1140
cagtgctttg cagctgcttt ccaaaatgct ttctttcact tcttccattc ctctgtccac    1200
aaaaaaagta gtgtgttctt gagcctatat aagagagggt cacacgctcc agtcgactca    1260
ccatcgatcc atctgacggt tagttccaag ggaaagaaga a                        1301

<210> SEQ ID NO 5
<211> LENGTH: 1243
<212> TYPE: DNA
<213> ORGANISM: Oryza sativa
<220> FEATURE:
<221> NAME/KEY: misc_feature
<223> OTHER INFORMATION: PRO0061 - beta-expansin EXPB9

<400> SEQUENCE: 5
aaaaccaccg agggacctga tctgcaccgg ttttgatagt tgagggaccc gttgtgtctg      60
gttttccgat cgagggacga aaatcggatt cggtgtaaag ttaagggacc tcagatgaac     120
ttattccgga gcatgattgg gaagggagga cataaggccc atgtcgcatg tgtttggacg     180
gtccagatct ccagatcact cagcaggatc ggccgcgttc gcgtagcacc cgcggtttga     240
ttcggcttcc cgcaaggcgg cggccggtgg ccgtgccgcc gtagcttccg ccggaagcga     300
gcacgccgcc gccgccgacc cggctctgcg tttgcaccgc cttgcacgcg atacatcggg     360
atagatagct actactctct ccgtttcaca atgtaaatca ttctactatt ttccacattc     420
```

```
atattgatgt taatgaatat agacatatat atctatttag attcattaac atcaatatga      480
atgtaggaaa tgctagaatg acttacattg tgaattgtga aatggacgaa gtacctacga      540
tggatggatg caggatcatg aaagaattaa tgcaagatcg tatctgccgc atgcaaaatc      600
ttactaattg cgctgcatat atgcatgaca gcctgcatgc gggcgtgtaa gcgtgttcat      660
ccattaggaa gtaaccttgt cattacttat accagtacta catactatat agtattgatt      720
tcatgagcaa atctacaaaa ctggaaagca ataaggaata cgggactgga aaagactcaa      780
cattaatcac caaatatttc gccttctcca gcagaatata tatctctcca tcttgatcac      840
tgtacacact gacagtgtac gcataaacgc agcagccagc ttaactgtcg tctcaccgtc      900
gcacactggc cttccatctc aggctagctt tctcagccac ccatcgtaca tgtcaactcg      960
gcgcgcgcac aggcacaaat tacgtacaaa acgcatgacc aaatcaaaac caccggagaa     1020
gaatcgctcc cgcgcgcggc ggcggcgcgc acgtacgaat gcacgcacgc acgcccaacc     1080
ccacgacacg atcgcgcgcg acgccggcga caccggccat ccaccgcgc  cctcacctcg     1140 ccgactataa atacgtaggc atctgcttga tcttgtcatc catctcacca ccaaaaaaaa     1200
aggaaaaaaa aacaaaacac accaagccaa ataaaagcga caa                       1243

<210> SEQ ID NO 6
<211> LENGTH: 1019
<212> TYPE: DNA
<213> ORGANISM: Oryza sativa
<220> FEATURE:
<221> NAME/KEY: misc_feature
<223> OTHER INFORMATION: PRO0063 - structural protein

<400> SEQUENCE: 6
cctagctata tgcagaggtt gacaggttgt ctcttagatc gattaataat atcacattga       60
tgcaattaat tatctgagat caataaagtt tttctttatg ttaaattaat atcagtaata      120
gatgctaagt ccttcattag tagtatccca catttaatca cagttggaca cacaaaaaaa      180
aaggcaatgc cattaatatg ccatctctct tgttttccat tgcctaccaa gtgccatatg      240
atatcatcat caggcacacc aatccataac tagttcatta gagcaagttt aataatagag      300
ctaactataa gcttataatt tatattggag taaacatgta tagtaaatga gctataaggt      360
tatttctttt tttctcctcc tctctctatc tcttacctat atatttaatg tatttgtctt      420
gaagtatgtg aatagctagc tcttgtatga gagccaatcc tctgcatttt ttaaattctc      480
tttcctccac ataagcatat agttggctta tagcctgcta ttatacttgg tcttagtaca      540 ctaaccccc  ttacatgcaa tgcaagctgt ctaattaaaa gggtttcaca acattttgaa      600
tgccactact agctcccaac cacaaccaca gatctagcta gggtttgttc atttctctcc      660
tctctcctcc tcctccttc  cgttgtgcca attcatccaa agtcattgag agccatacta      720
ctccatatca tattactcct acatgtgtac tacatttata ttgatgatct gtaagagcaa      780
aagtattaat ggggatcaca ggattgcagt aacagcagca ggtaccccct cctttaacat      840
ccgcagttac gcctcccacc taccgtcttc tctgccgatc gatgacgatg agcttctcct      900
ccgctataaa tcctctcccc tcctctctcc ctcctcctcc aactccacat cgatcagcag      960
cagcagcagc ttgcacactc gagcttagct tagcttttgc aagagagatc gagctagag      1019

<210> SEQ ID NO 7
<211> LENGTH: 1212
<212> TYPE: DNA
<213> ORGANISM: Oryza sativa
<220> FEATURE:
```

<221> NAME/KEY: misc_feature
<223> OTHER INFORMATION: PRO0081 - putative caffeoyl-CoA
      3-O-methyltransferase

<400> SEQUENCE: 7

| | | | | | |
|---|---|---|---|---|---|
| atggtgccat | gtcaataaga | catcataata | gaaactacac | tccacaaccc | atagtttctt | 60 |
| aaagtgggtc | attaataaat | acatcatcta | tcttttctat | caatcatatt | tattctttat | 120 |
| ctattatgac | ggcactattt | tctcccaatg | taaaacttga | taatgtctag | tgcataggtt | 180 |
| ctcgtgttga | agctgtttct | tacatgagac | ccagtttctt | cttctctcca | ctctctctta | 240 |
| attaatataa | tgtcacataa | gttaaaagtt | ctagtaaata | ataatatagt | taatgacata | 300 |
| gacaacatcc | tagatgtagg | gttaggagtc | ttcggacagt | agcaaccctg | ttttgactcc | 360 |
| ttttttggct | gcccatccac | agtcgccacc | agaaaattca | ctgtgcccaa | atcaatggaa | 420 |
| gcgcctacta | gatccatcca | tcttcgtgac | agctccgagc | tttctcctgg | ttattttct | 480 |
| cccaaaaata | cattcagaac | acgatctcaa | atttaaacta | atggagtgct | actgcatttc | 540 |
| ttaattataa | gtcgcagcac | cactcattaa | tcatttccat | cacaggtaaa | tcgtggtgag | 600 |
| ctggtggttg | ctactgtact | actagtacta | cctgtcgcag | ctttgtagaa | gccgttttcg | 660 |
| ctgaagcttc | ttcttcttcc | ctgggcaaaa | taattttaag | caggcggaat | aatattggga | 720 |
| taaacagggt | ggacaaaagc | gtgcgatccc | tttctttaac | caaaccacga | cgaaagcagg | 780 |
| ttaggtcgcg | gcaggtggtg | gtggtaggaa | gaagaagaaa | gagaggggaa | aaaaaacaaa | 840 |
| aatttcacat | gcatcatgca | tgaagtagta | catgtagtac | tgagtactgt | aataatgttc | 900 |
| agtttactgg | accgtctcaa | cgggaagacc | aaattaacgc | ttataaaata | cccttttttt | 960 |
| gggcactgat | catggccact | acgtttggtg | gctcaacaac | caggtcaccg | tgcgatcgat | 1020 |
| cgattgctaa | tttattttt | gaaaggaag | ggaggaaaaa | agaccgggtg | tttggtggcg | 1080 |
| ccaccaaccc | tgctctcgtg | agccgataaa | tattgctcgc | cggagctctc | ggttgacgac | 1140 |
| ccaaccaatc | gactcgcacc | accaccagca | gctcaagcag | caacagctca | aacggaggaa | 1200 |
| gatctcatcg | cc | | | | | 1212 |

<210> SEQ ID NO 8
<211> LENGTH: 1052
<212> TYPE: DNA
<213> ORGANISM: Oryza sativa
<220> FEATURE:
<221> NAME/KEY: misc_feature
<223> OTHER INFORMATION: PRO0091 - prolamine RP5

<400> SEQUENCE: 8

| | | | | | |
|---|---|---|---|---|---|
| gtttttctat | gaaccggtca | ttaaaccgtc | cccggttaga | ccgaacaagc | cacaataatc | 60 |
| ttgaaatggg | ccttgatgtg | gcccaattgg | tctgcctaga | gcgttttggt | tggcaaaaat | 120 |
| caatctccta | ttctcggcac | gtgtgatata | caatggtaag | tgagatatac | aattctcggc | 180 |
| acggctacat | tacaaggtgt | cgcattgtgt | caatgtttgg | ttaatttgct | agattcacat | 240 |
| aatacatgcc | aggaagttca | gaacaatgtg | ttgcctttca | ccggaaaact | tgttggagc | 300 |
| aaatgccttc | ttcttttttg | cttctgcttc | ttgagtccat | gtggaggaag | cagtagatag | 360 |
| ctgatgatat | caggattcct | tctgtgtctg | tgtaggtgta | gcaacaccac | tataattttt | 420 |
| atttagcaac | acaatatcaa | tttggtctat | aaaagtatga | attaaatcaa | tccccaacca | 480 |
| caattagagt | aagttggtga | gttattgtaa | agctctgcaa | agttaattta | aaagttattg | 540 |
| cattaactta | tttcgtatca | caaacaagtt | ttcacaagag | tattaatgga | acaatgaaaa | 600 |

-continued

```
ccattgaaca tactataatt ttttttctta ctgaaattat ataattcaaa gagcataaac      660
ccacacagtc gtaaagttcc acgtgtagtg cattatcaaa ataatagctt acaaaacata      720
acaaacttag tttcaaaagt tgcaatcctt atcacattga cacataaagt gagcgatgag      780
tcatgtcatt attttttgc tcaccatcat gtatatgatg tgggcataaa agttactttg       840
atgatgatat caaagaacat ttttaggtgc acctaacaga atatccaaat aatatgactc      900
acttagatcc taatatagca tcaagcaaaa ctaacactct aaagcaaccg atagggaaac      960
atctataaat agacaagcat aatgaaaacc ctcctcatcc ttcacacaat tcaaacatta     1020
tagttgaagc atagtagtag aatcctacaa aa                                    1052
```

<210> SEQ ID NO 9
<211> LENGTH: 1216
<212> TYPE: DNA
<213> ORGANISM: Oryza sativa
<220> FEATURE:
<221> NAME/KEY: misc_feature
<223> OTHER INFORMATION: PRO0095 - putative methionine aminopeptidase

<400> SEQUENCE: 9

```
cctgatggat gatgaatcac tgatcgattt ctagttctta ttctctgaag atgaaccgaa       60
gatccaagat tggtccatga aattatcctt tcttgatttg gccctccgag aatagattcc      120
tgtgcaatct agtcagtagt tgttcaggtc atgtaaacgt acggtaagaa atttatgtgc      180
agagggtttt ccagtttatc ctatgcattt gacctctggt catgtattga ttctgagaca      240
aagtgtagtg atcgcttgat gatactagta cacattgctg ccttcttttt tgtcctgtaa      300
aagatttatt attggcagca atggatggta gagagggcaa tctgcttctt agttttgagt      360
ataaagtttt aagttttgag cagagtttcg aaaatttgca gtagaaagtt tgaaatttca      420
aattggaagt acagtttttc aaatttccag tataaatttt taaacccact gagaaaccaa      480
gagcatatgg gcgatcaaaa atttcttttc taaaggaaaa atatttttta aaaaacactt      540
agtagtatat caaaattctg aggtaagctc attaggccca ttcactgtac ggcccatgaa      600
gcccagtctg gtgagatggg cctacccgtg caggcagaga tggatgggcc tttaattgta      660
ggcccatgtt ggaaagccca ccaaagccca ataatatatc ctcctcacct tcaaccctaa      720
tcctcctctt cttctagaag actgaaaatt cctctccttt cttctctcgc cctcaccgct      780
cgccgaggtt gccgtctcct tgtctcctcc gctccttgcg ccgccgccgc gacgagtcgc      840
ggggaggggc ggcgatctcc atctccatct gaggcgagga gagcagggga ggtgagggga      900
tcctggtgag gtgagcatcc acgtcctctt tcttttttc tgattcatct ctctctctct      960
cgcacatcgg gactggaatt tgcttgcgtt cgttcgttaa gttaacccta gcttctcttc     1020
tagatctgga agaaactctt cttctttaa tttcagagcc ttaaccttaa tagtacaagt     1080
aacagtttgt tgttccccg aaaagtttgg atgccttcca aatagagaca catgttattt      1140
attttggaat gtaatttgtc cctggattta ttcattcagg tttgtgatta ctggacaata     1200
gaaatattta cacaat                                                     1216
```

<210> SEQ ID NO 10
<211> LENGTH: 1237
<212> TYPE: DNA
<213> ORGANISM: Oryza sativa
<220> FEATURE:
<221> NAME/KEY: misc_feature
<223> OTHER INFORMATION: PRO0111 - uclacyanin 3-like protein

<400> SEQUENCE: 10

```
tcgttaagtt tgatgatttc tgatgaccca tggtcaccta gcggctagca gtaccatgca    60
tgatcaccct ccacaaagaa atggtacagt acatctccgt cccaaaataa gtgcagccat   120
gtatatccat gcctaacgtt tgaccgtccg tcttatttaa aaaaattatg aaaaatttaa   180
aaatatttag tcacacataa agtattattc atgttttatc atctaatagc aacaaaaaat   240
actaatcata aaattttttt taataagata aacggttaaa cgttgaacgt gaatagtgca   300
aaacttattt tagaacggag ggagtacgaa gtaactccgg aactacatat agggcaatta   360
ttgccctatg tatgcatata gtcaatcaat taactgctga caatggaaaa gctaatcaat   420
caatcaatgg tttgattaat caaattaagc caggtcagtc cgtcagtgta cattcactaa   480
ttaaattaac aggtttgttc aacggttcaa ccaacatctg ccatcaacat cttttcgttg   540
cacctttctt gactctttat gctatttttgc taaaaaaaaa cttctcttta catcacttat   600
aacaatatat atttctgctt taatttgtaa tcttttttt ctgcgttgca acggaaatca   660
cgagcgatat atggtgaaga ctgatgataa tcgtatttct gatgacccat gattccgcgg   720
tgtaccatct gttctgtcaa ctaaaaagtg gagtagttcc ttgacggaag aagggagcaa   780
aatagaagat attctcagtt gatctgcagt tgttgttagg tcactatatt cagaaatcgc   840
agttgctgtt gtttaaattg tgtgtgacag cagacagcta attatcagta cacgtatatg   900
agcaatacta gtgaatctgt actaatttaa cgagagtatt ttctatatac aaatacaaca   960
gcaaaactgt gccactggcg ccgaatacgt acggacagag ctcaggcaat caggggagca  1020
gcaaaagagg agagagttgg tgccaagcac aactaaaccc aactgcaccc aaaaactaat  1080
cagcatttca gttcgcttta gttagtacta ccacctgcat ctctttacca acactatata  1140
acccgcagtg gacctgcagt catctcacta attcagtgaa gccaccagta ctagtacggc  1200
tctaatcagt tcgcgtttgc taattaactc tgccatc                          1237
```

<210> SEQ ID NO 11
<211> LENGTH: 1100
<212> TYPE: DNA
<213> ORGANISM: Oryza sativa
<220> FEATURE:
<221> NAME/KEY: misc_feature
<223> OTHER INFORMATION: PRO0116 - 26S proteasome regulatory particle non-ATPase subunit 11

<400> SEQUENCE: 11

```
ctaagggcag cagccattgg gctctatagg tgtggttgca agtgcactta caagcgagca    60
acctggtaga atatccccga gatcagtagt taccgtgatt ggttcagact tgagaggcta   120
attttttcgt acctgtagct ttattacatc gcatttcctc ttattgaagt ttagccgagg   180
tggtgcggat ggatattcag tctaacagac tcaatgaacg ctttgttgta tgacttgtac   240
agtactggct gctcgaacag gatggttcag cttccagaaa tttggcaacg ctccatttca   300
aagaaaatca ttcagtattt gccttcttgt tgttacattg atctcatata aagtcacttt   360
gatcgttgac atcttgtttt ttggttcgtt tgccatggta gtttcccttg ctgctgggag   420
gattgccgcc tgaactttt cttttttgcg aggatgttat ttttgccaga caagaacggg   480
aataagcaaa ttgtttggtg gaactaaagt aaactcgatc tctttccgag aagtgtatta   540
ttttcacgtg taccatcaat ttttttgaaa gtaaatattt ttcccctta actaatgttc   600 actttggacc ggtaatcttt acctttattt aactttgggc tatctaactc tcttctaaag   660
catataaacg atcttgagta catcgattcc tacttatcat ttaactctcg tagcttaatg   720
```

```
taagattatt tctttgaaat atgataaatt ggatgcatat gaatgaaaga gtcaaggatt    780
aagtgattcc tcaaaaaaaa aaaagagtga aatttattta ttttttcccct ttcgacacga    840 agaagggctt ggttggagga aaatggccca gattcagatg accgaggccg agtaccatgg    900
ggcccacaag aataataagc cccgagccca aacgctaagg cccacgagaa gccgtgcgct    960
ggaagaaaga agaaaccgc ggccgtcttc acaccgaagc ggcggacgag acgactcgca   1020
gtcgcagcct ctttcctcct ccgtctctct ctccctctt cctctcctcc gcgcggcgaa    1080
cgaagcgagc gagcggcggc                                              1100
```

<210> SEQ ID NO 12
<211> LENGTH: 1216
<212> TYPE: DNA
<213> ORGANISM: Oryza sativa
<220> FEATURE:
<221> NAME/KEY: misc_feature
<223> OTHER INFORMATION: PRO0117 - putative 40S ribosomal protein

<400> SEQUENCE: 12

```
cgtgttcatg ttcgcattta ggattggact ttttaggat ggagaggata tgtcctaacg     60
gaaatgtcat gtctatgctc cgatcttata aatttgttca atagcgttgc aaacgcgatc    120
attaaaaagg cggtaagaga actaccacat tttcgaaagc ccattctctt cgtgagttac    180
tggaattatt tggcatagca catgcataaa gatgctttag taatgagctc aataaaacac    240
gacagctttg catgtagcca caatgctata gtaaatgagt tgtacttctt ttgcattgca    300
aagtggtact gaccttgttt aggcagctag cttcattcat tttttgaatt ctatagttat    360
agttataaag attatcataa tttagataag aatccggtat gtttgagaag ctggagtttc    420
tagagaagct ataacaactc gaagctccct aaacagagcc attgaacatt gagctgtcca    480
gtatatcatg acaaatgat acattttgca tgggcatatg tgtctaagaa acaaacatc     540 acaattcaat gagtcactct aaaaaaaaag gcaaaacact caacaaaacc ataccgtgaa    600
agtgaaccta aatgaaatg aaattttgat aagcatgctt acccaggtgg aaatttcaat    660
ctaagaacaa tttccaaaac caccgtccat agaaatatgt ggaattcatt cagaattttc    720
ataccacacg ataaaattta tagggaattt aacttttgcc attttttaccg aacaccacct    780 tttcatttgc tcctataatg ttatcgaaaa gagagtgttt gttaattatt tgtcactttt    840
atcacgacat gtagccgtga caacgtggcg ttcctcgtgg agcccacccg tcagccgccg    900
tacgcaccac catcaaagaa ttcaagacgg agagcgtcgt cgccgtcggc aaggcggcgt    960
gttttgttca ctgtacgttg cttcggcgtg ggcccaatct tgttcgggcc taactagttc   1020
ttcccagccc aggcccatta agcctaccaa cccggacggc ccggaggag ctagggtttc    1080 acccttcact atataaacct ctctctcctc tccggccgc cgcctccgaa gccctagctc    1140
ctcccgccgc cgccgccgcc gccgccgccg cctctccact cgagagaccc agccgccgcc   1200
gccgccgccg ccgcca                                                  1216
```

<210> SEQ ID NO 13
<211> LENGTH: 1210
<212> TYPE: DNA
<213> ORGANISM: Oryza sativa
<220> FEATURE:
<221> NAME/KEY: misc_feature
<223> OTHER INFORMATION: PRO0122 - chlorophyll a/b-binding protein
    presursor (Cab27)

<400> SEQUENCE: 13

```
cagatgccac agtatggtgt accaccagct gctccacacc atgctccacc ggctggccaa      60
ccaatgtatt tcccgaaata atctatcttt atccgatgta caagcaatta gagcaattgc     120
aaatgttgcc tgcaatactc gggtctgggt atcttctctt caaattttgg gttgtaactc     180
gtctatgcag ctattcatat tgtaactcag tgagctccct gtcgcaaatg tgcctctgcg     240
tcagtcgctg tctgtaaact gtccggcaat tagaaattcc catccttagc atgcctggta     300
ttgttcagct cgaaactgaa attttcttc gtgccctata ttttttcggt gtagataagt      360
gttccgctgg aattttatgc aggtgctgta ccctatgtgc tgcttttttt ttgtgtgggg     420 cgccccccg ggggggggg ggggtttcct ggcatgattg caaataagaa ccccggggca      480
aatctgctgg ttggttgcaa ataataaccc ctccaaatct gcgcagatga acccccattc     540
aggacatgaa ttacgattgt tcatgagcta tttggatcat ggaaagattg gaaacaaaca     600
cttacgtcaa ggtttctact aattacgtga ttccgatttc agagtcagcc atggctatac     660
tgcctttgct ccagtaaaca tcgctgctct agtaacaaac attgcagtaa acatcacaac     720
tatccaattc ccttgttgct gctctagtaa aaaacattgc aattatccaa ttcccagata     780
ttttctttca ctactccaaa acctaaagta catatacgtg agttgagtga tccagcaaca     840
taaaaatccg aggctccgag cgatctgcac caaccatctc acccgtccga cgtggcagca     900
gcaaccagcc acagctgaga cctccatcca atagaaaccc tccctttgat tccccgtat      960 cccggcatcc ggataacgct ggataagagg cgacgcctcc cattggccac acccacccaa    1020
caacgcatcc tggccgtccg atccaccccc accgccgatc tccgccgtcc gtcgccgccc    1080
tcgccaccgt ggccacctgg cagcgccggc cactcccgga cagtttaata caagccacgc    1140
ctttgctccg tgccggccaa aacgtaccct tgtgactaca cccgcttcgc ttcctcccct    1200
ctctaagccg                                                          1210

<210> SEQ ID NO 14
<211> LENGTH: 1179
<212> TYPE: DNA
<213> ORGANISM: Oryza sativa
<220> FEATURE:
<221> NAME/KEY: misc_feature
<223> OTHER INFORMATION: PRO0123 - putative protochlorophyllide
      reductase

<400> SEQUENCE: 14
ttgcagttgt gaccaagtaa gctgagcatg cccttaactt cacctagaaa aaagtatact      60
tggcttaact gctagtaaga catttcagaa ctgagactgg tgtacgcatt tcatgcaagc     120
cattaccact ttacctgaca ttttggacag agattagaaa tagtttcgta ctacctgcaa     180
gttgcaactt gaaaagtgaa atttgttcct tgctaatata ttggcgtgta attcttttat     240
gcgttagcgt aaaaagttga aatttgggtc aagttactgg tcagattaac cagtaactgg     300
ttaaagttga agatggtct tttagtaatg gagggagtac tacactatcc tcagctgatt      360
taaatcttat tccgtcggtg gtgatttcgt caatctccca acttagtttt tcaatatatt     420
cataggatag agtgtgcata tgtgtgttta tagggatgag tctacgcgcc ttatgaacac     480 ctactttgt actgtatttg tcaatgaaaa gaaaatctta ccaatgctgc gatgctgaca      540
ccaagaagag gcgatgaaaa gtgcaacgga tatcgtgcca cgtcggttgc caagtcagca     600
cagacccaat gggcctttcc tacgtgtctc ggccacagcc agtcgtttac cgcacgttca     660
catgggcacg aactcgcgtc atcttcccac gcaaaacgac agatctgccc tatctggtcc     720
cacccatcag tggcccacac ctcccatgct gcattatttg cgactcccat cccgtcctcc     780
```

| | | |
|---|---|---|
| acgcccaaac | accgcacacg ggtcgcgata gccacgaccc aatcacacaa cgccacgtca | 840 |
| ccatatgtta | cgggcagcca tgcgcagaag atcccgcgac gtcgctgtcc cccgtgtcgg | 900 |
| ttacgaaaaa | atatcccacc acgtgtcgct tcacaggac aatatctcga aggaaaaaaa | 960 |
| tcgtagcgga | aaatccgagg cacgagctgc gattggctgg gaggcgtcca gcgtggtggg | 1020 |
| gggcccaccc | ccttatcctt agcccgtggc gctcctcgct cctcgggtcc gtgtataaat | 1080 |
| accctccgga | actcactctt gctggtcacc aacacgaagc aaaaggacac cagaaacata | 1140 |
| gtacacttga | gctcactcca aactcaaaca ctcacacca | 1179 |

<210> SEQ ID NO 15
<211> LENGTH: 1808
<212> TYPE: DNA
<213> ORGANISM: Oryza sativa
<220> FEATURE:
<221> NAME/KEY: misc_feature
<223> OTHER INFORMATION: PRO0133 - chitinase Cht-3

<400> SEQUENCE: 15

| | | |
|---|---|---|
| tttggcgcgg | ggcagaagag tggactttaa cttctttttt aataaaatct ccaattaata | 60 |
| tgtaattata | atatactttt aatcaaaaca tgcaaagcta gcagtattta catcactaga | 120 |
| agtaaatctt | tcttgctcat gatgcttcag ccggacggaa ccctaaaata tagatggggc | 180 |
| ggatacactc | gattaaaaca gctaattgca acacatatca tataaggttt tggaattcat | 240 |
| accaaatgct | ccgaaattcg tctatttcga tgaggcccaa gacatgacct cctgtttcgc | 300 |
| ccatagttta | tggtgtttgg taaaatttgg ttaaaatctg tctatttag taggtcccga | 360 |
| aattcttatg | caattgaatc ctagaaccct atcatattta tattgcaatt gcacaaaaat | 420 |
| aatgtgcaat | caatatattc caattgcaat acatatcaag catgaggtgt aatacatatc | 480 |
| cagccgctag | cactgggtct gttgaggtgc ttcttgcagc aacagctgca atctgtttgg | 540 |
| ctaggctgtt | ggcgccaggc actgctgtcg tgctgcaaca atggcacatt cgtcgagcac | 600 |
| acaaccgcgc | ctatgcacag cgcaagctcg ctgccttgga ccgtggttcc agtgttgcat | 660 |
| caaggcttag | tggattgagc gagaagacga actgacaatg ccaaagatgc gatgctgcga | 720 |
| gtgtggactg | cggaagatga atcgagatca atcaattcgt tatgcttgaa aggctggaat | 780 |
| aactgatcag | ttggctggat cgatggtatg tactagataa tatgcggtct aggcctagac | 840 |
| caagaagcag | aagaggagtc gggtcgggag tgtggggcga cgtaggctgt agctgggccg | 900 |
| gccgccccag | gccgcctaat gagtgtgtcc gcccctggcc tgacacgatg ggtaattaaa | 960 |
| tagttatgca | tgtccctctt tgtctaaaca atatgtataa aattgacgat atcttgggca | 1020 |
| aaatcactgg | gcatggcaca caggagagct actttagcga catgaatcta ggcgaaaatc | 1080 |
| tattgaacca | aaaatcgact gtaatctcat gaaaattttc gtcataatta tagcaaaatc | 1140 |
| gttgttggat | tgattgcacg agaaaacaga agaagggagc taggtgatat tatattgttt | 1200 |
| tgttgcctac | ataaatctta aagcaatcga atggtctaaa atttacaaga tttttaaaga | 1260 |
| ggttttcgta | ccgtatagac cccggccggg tcaaacttat ttggtcgtcg ctggttgttt | 1320 |
| gtagcacgcc | agctccatat atgtggattg cagctggtct atgataagtt cggtcgatct | 1380 |
| gagatcaatc | tatcaatcgt caacccttg cctttgttag cgagctagcg tgtacacatt | 1440 |
| tcaattatat | atggtgcatg catggcatcc acgcctccac ggtcaacgtg gaaatatctc | 1500 |
| tggaaactta | ctttttctaa ataactgaac ggattggagg caggagacaa atttgaccaa | 1560 |
| cacaatatat | ccacgacggc tagacaatac tagtagatgc atgcatggaa ggatatagta | 1620 |

```
gtacttgtta atcgtggaaa ctttggtaat gcgaatgcat ttcaattcgt tgctgaagat   1680
cgatgcacca tgcatatcca tctctatata aagccatgcg atcccaccga ttcttgcaca   1740
cacactagct acttctactt ctatcatacc aaacaaacta gcttaatttg cattgcatca   1800
cattgccg                                                            1808
```

<210> SEQ ID NO 16
<211> LENGTH: 1828
<212> TYPE: DNA
<213> ORGANISM: Oryza sativa
<220> FEATURE:
<221> NAME/KEY: misc_feature
<223> OTHER INFORMATION: PRO0151 WSI18

<400> SEQUENCE: 16

```
gcttgagtca tagggagaaa acaaatcgat catatttgac tcttttccct ccatctctct     60
taccggcaaa aaaagtagta ctggtttata tgtaaagtaa gattcttaa ttatgtgaga    120 tccggcttaa tgcttttctt ttgtcacata tactgcattg caacaattgc catatattca    180
cttctgccat cccattatat agcaactcaa gaatggattg atatatcccc tattactaat    240
ctagacatgt taaggctgag ttgggcagtc catcttccca acccaccacc ttcgtttttc    300
gcgcacatac ttttcaaact actaaatggt gtgtttttta aaatattttt caatacaaaa    360
gttgctttaa aaattatat tgatccattt ttttaaaaaa aatagctaat acttaattaa     420
tcacgtgtta aaagaccgct ccgttttgcg tgcaggaggg ataggttcac atcctgcatt    480
accgaacaca gcctaaatct tgttgtctag attcgtagta ctggatatat taaatcatgt    540
tctaagttac tatatactga tgaataga  ataagtaaaa ttagacccac cttaagtctt    600
gatgaagtta ctactagctg cgtttgggag gacttcccaa aaaaaaaagt attagccatt    660
agcacgtgat taattaagta ctagtttaaa aaacttaaaa aataaattaa tatgattctc    720
ttaagtaact ctcctataga aaacttttac aaaattacac cgtttaatag tttgaaaaat    780
atgtcagtaa aaaataagag agtagaagtt atgaaagtta gaaaaagaat tgttttagta    840
gtatacagtt ataaactatt ccctctgttc taaaacataa gggattatgg atggattcga    900
catgtaccag taccatgaat cgaatccaga caagtttttt atgcatattt attctactat    960
aatatatcac atctgctcta aatatcttat atttcgaggt ggagactgtc gctatgtttt   1020
tctgcccgtt gctaagcaca cgccaccccc gatgcgggga cgcctctggc cttcttgcca   1080
cgataattga atggaacttc acattcaga  ttcgataggt gaccgtcgac tccaagtgct   1140
ttgcacaaaa caactccggc ctcccggcca ccagtcacac gactcacggc actaccaccc   1200
ctgactccct gaggcggacc tgccactgtt ctgcatgcga agctatctaa aattctgaag   1260
caaagaaagc acagcacatg ctccgggaca cgcgccaccc ggcggaaaag ggctcggtgt   1320
ggcgatctca cagccgcata tcgcatttca caagccgccc atctccaccg gcttcacgag   1380
gctcatcgcg gcacgaccgc gcacggaacg cacgcggccg accgcgcgcg ctcgatgcgc   1440
gagcccatcc gccgcgtcct ccctttgcct ttgccgctat cctctcggtc gtatcccgtt   1500
tctctgtctt ttgctcccg  gcgcgcgcca gttcggagta ccagcgaaac ccggacacct   1560
ggtacacctc cgccggccac aacgcgtgtc cccctacgt  ggccgcgcag cacatgccca   1620
tgcgcgacac gtgcacctcc tcatccaaac tctcaagtct caacggtcct ataaatgcac   1680
ggatagcctc aagctgctcg tcacaaggca agaggcaaga ggcaagagca tccgtattaa   1740
ccagcctttt gagacttgag agtgtgtgtg actcgatcca gcgtagtttc agttcgtgtg   1800
```

```
ttggtgagtg attccagcca agtttgcg                                      1828

<210> SEQ ID NO 17
<211> LENGTH: 1267
<212> TYPE: DNA
<213> ORGANISM: Oryza sativa
<220> FEATURE:
<221> NAME/KEY: misc_feature
<223> OTHER INFORMATION: PRO0169 - aquaporine

<400> SEQUENCE: 17
cgtcctcctt ttgtaacggc tcgcaaatac aatgggttgt ttagattcat gtcattttaa     60
atcatattat tttttataaa gttatcaaaa tgtacatata tttatttatt tttaccaaac    120
tttactaaat gagataatcc aacaaatggc atttaaagcg ttcaaatcca agaaatgcca    180
tcgccgttat gcttccgtcc gtttcacgcc gttaaaatac aatgttcatc ctataacact    240
taatggtgtg gaatggacgg aaccctaacg gcgatggcat ttttgggata aagtcgtttg    300
tacgatggca tttcttagaa ctcatatttg tcgatggcat tttttgaatt tggatgattg    360
tcaatggtat tttttggatt atctcttagt aaatacataa ggaatcatgc caaaacttga    420
caatattgtc aacttatcaa aatttaattg ggattatttt ggcgataata tgaacagccc    480
ttacatttct gaagaattat agctcaaata tggctatggc cctgtttgga ttcggagggc    540
tatttaatag ccctccggaa tcttgctatt taagagtatt aaacgtagat tactgataaa    600
actcattcca taaccccctac gctattctac gagacgaatc taacgaggta tattaatcca    660
tgatttgcta cagtaatcag ccgctaatcg tggattaata tacatcatta gattcgtctc    720
gtaaaatagg ctagggatta tggaatcggt tttatcggta atctatgttt aatacttcta    780
aatagcaaga ttccgaaggg ctatttaata gctcggagca tccaaacaag gcctatgttt    840
agatccaaac ttccaacttt ttctatcaca ttaaactgtc atacatacat aacttttcag    900
tcacatcgta ccaatttcaa cccaaacttt caactttgga agaactaaac acagcatatg    960
acagtgcagt tcagctcaat tttgttcgga gcctaaaaaa aagaaaagaa aaaaagctca   1020
atttggataa ggctatgaat aaactcaaaa aagcatccaa cctaaccacc acactggccc   1080
accagggccc acgctccact cccgtgatca tcacctcctt ccctttccag aaccaccttc   1140
tccttccttc ctcctcttct tcttcagtgt actctgcctt tataacaccc tactcctctc   1200
tctcacctcc accatctagc tcactcacac agtctccact cacacgcatt gcagaggaga   1260
ggcgaca                                                             1267

<210> SEQ ID NO 18
<211> LENGTH: 1130
<212> TYPE: DNA
<213> ORGANISM: Oryza sativa
<220> FEATURE:
<221> NAME/KEY: misc_feature
<223> OTHER INFORMATION: PRO0170 - High mobility group protein

<400> SEQUENCE: 18
catgcggcta atgtagatgc tcactgcgct agtagtaagg tactccagta cattatggaa     60
tatacaaagc tgtaatactc gtatcagcaa gagagaggca cacaagttgt agcagtagca    120
caggattaga aaaacgggac gacaaatagt aatggaaaaa caaaaaaaaa caaggaaaca    180
catggcaata taaatggaga atcacaagag ggaacagaat ccgggcaata cgctgcgaaa    240
gtactcgtac gtaaaaaaaa gaggcgcatt catgtgtgga cagcgtgcag cagaagcagg    300
```

```
gatttgaaac cactcaaatc caccactgca aaccttcaaa cgaggccatg gtttgaagca    360
tagaaagcac aggtaagaag cacaacgccc tcgctctcca ccctcccacc caatcgcgac    420
gcacctcgcg gatcggtgac gtggcctcgc ccccaaaaa tatcccgcgg cgtgaagctg     480
acaccccggg cccacccacc tgtcacgttg gcacatgttg gttatggttc ccggccgcac    540
caaaatatca acgcggcgcg gcccaaaatt tccaaaatcc cgcccaagcc cctggcgcgt    600
gccgctcttc cacccaggtc cctctcgtaa tccataatgg cgtgtgtacc ctcggctggt    660
tgtacgtggg cgggttaccc tgggggtgtg ggtggatgac gggtgggccc ggaggaggtc    720
cggccccgcg cgtcatcgcg gggcggggtg tagcgggtgc gaaaaggagg cgatcggtac    780
gaaaattcaa attaggaggt gggggggcggg gcccttggag aataagcgga atcgcagata    840
tgcccctgac ttggcttggc tcctcttctt cttatccctt gtcctcgcaa ccccgcttcc    900
ttctctcctc tcctcttctc ttctcttctc tggtggtgtg ggtgtgtccc tgtctcccct    960
ctccttcctc ctctccttc ccctcctctc ttcccccctc tcacaagaga gagagcgcca    1020
gactctcccc aggtgaggtg agaccagtct ttttgctcga ttcgacgcgc cttcacgcc    1080 gcctcgcgcg gatctgaccg cttccctcgc ccttctcgca ggattcagcc              1130
```

<210> SEQ ID NO 19
<211> LENGTH: 1230
<212> TYPE: DNA
<213> ORGANISM: Oryza sativa
<220> FEATURE:
<221> NAME/KEY: misc_feature
<223> OTHER INFORMATION: PRO0171 - reversibly glycosylated protein RGP1

<400> SEQUENCE: 19

```
tagtaccatt cttccctcgt gagcataaat gtattcatac aaaatagtaa aatgtatcct    60
cacaaagatt gtaagtatat ctcgcaacta taaatatgtt gtcattttag taacaattgt    120
tcataaaata gtaatcatgt tctccataac agtaaatgac gaggcgttaa tagtggttta    180
ggttctcatg attgtaaatg ttgagtcgct tgtagcggct taagatatag tagagagtat    240
atctagtttt atcaagacaa acattgcgta atgcctcgga cctaatataa agtaggaat    300 tttaaccttt gagaaactgt aaccaattga aactgcaagc tttaaaaaaa catctattgg    360
aagtgatatt atatagacaa ataagttttc ttactcttac tctctcagtt tcaagttata    420
aaatgttttg gctttggtca aaatcaaact tcttcaagtt taatcaagtt tatagaaaaa    480
atagtaatat ccaagataaa tttattataa aaatatattt aattattatt ttaataaaac    540
taatttggta atgtaaatat tactatattt gtctataaac ttagtcaaat ttaaaacagt    600
ttaactttga ccaaagtcaa aacatcttat aacctgaaat ggatggagta tttgtttgtt    660
tctattttag gaaacggccg tttctttcca ttgattttga gataagcaga gctttaaacc    720
actgccacta ttgtgcattt catttgattt aacactttta ccccttatct ccaataaaaa    780
cgatattaag atacccctat cttttatcca ccgcttggaa caaaccaaaa aaaataaaaa    840
ttcaaacctt ctacactggt acacacgttc tctctttcca tgcaccgaca ggtctctccc    900
agatccaacc caaataaat ttggacgcat cccaaaattc ggcaaacata tgacgcaaac    960
caaaacaaaa taggcacaaa ataatataat actcctatct aattaattat acacaatttt   1020
ttttaaaaaa aaagcaaggc aagcgaagca aagcaaagaa ggaaacgaat aacaaagtcg   1080
tcgtcctccc ggagctcccg ctctataaat cgctcctcct ccccacccac ccaaacccac   1140
acacacctca cacctcacca ccatcacctc ctcctcctcc tcctcttcct ccgcgcgcgc   1200
```

```
gagatccagg gagagggaga gggagagatc                                    1230
```

<210> SEQ ID NO 20
<211> LENGTH: 1234
<212> TYPE: DNA
<213> ORGANISM: Oryza sativa
<220> FEATURE:
<221> NAME/KEY: misc_feature
<223> OTHER INFORMATION: PRO0173 - cytosolic MDH

<400> SEQUENCE: 20

```
gtttggttgg tgaccgcaat ttgctatacc aaaatcttag acacagttga attaagctac     60
actttattag cacattggcc cgtgcgttat attgtcattt tctagccaaa gtttgccata    120
attgtggcta acaaattgtt ggccacattt tggctacgtt cgataggaca tgttcccaac    180
ttctccttct cgttttttcgc gcgtacgctt tttcaaactg ttaaacggtg tgttttttgc   240
aaaatatttt tttacgaaag ttgcttaaaa aattatatta atctattttt tttaaaaaaa   300
gtagctaaaa cttaattaat ctcacgctag acgctgcttc gttttacgtg tcgggtaccc   360
aaccctcact cccgaacaca gcctttgtgt ggtttactac agttatagta aagctagtct   420
ccatccaaac aatcctttag tccatataac ttcgtatact ccaaaattcc actcgttcta   480
cggacatcac taatacgaag atcaagtgga agatagatat ttttaatgac atgttatttt   540
cagtgaacac ttgaggtcct cacgatccac aaacacacat tttcgtagat aagttctgaa   600
atactcccata cggcggttgt cacgatgtca tgatcgtcgt tacccaagga agaagaaaag   660
agtggcatct tctccacgcc agtgttccca acggagcatc ttttcttccc ccacacggca   720
tcgacgtcac actttctggt gcaaacttta ataattagtc caaaacaaa aaagaattt    780
cggccacatc ttctcccgaa acgccaggtg ggccccacct gcatcactga cagcctgtcc   840
ccacaacgcg cagtcgtgtc cccacctgtc aggatgttag cgtctccgtt gcaggtttcc   900
cagatcccat cgccgatctg tgggccagcc ccacggtgt cacgcccgcg cacacctggc    960
tccaacccac ccacccccacg cgctccgtgg ccgacagcgt ggaccacct aggtggggcc   1020
caccgtcagt gggagatggg taggggagcc ccacgtggg agcaacgggg gttctccggg   1080
ctccccgtcg ccgcgaggtt aaataacggc caccgttc cccctctctc gcaaaactca    1140
cccaaaagag cagcgtcgcc tctcctcctc cccctaacc cctacgcttc cagaaccttc   1200
tcgaagctcc cgctccccc ccccttccgc tcca                               1234
```

<210> SEQ ID NO 21
<211> LENGTH: 1553
<212> TYPE: DNA
<213> ORGANISM: Oryza sativa
<220> FEATURE:
<221> NAME/KEY: misc_feature
<223> OTHER INFORMATION: PRO0175 RAB21

<400> SEQUENCE: 21

```
gtcaccaccg tcatgtacga ggctgcttca ccactgcctc actgccacca gcgtctcccg     60
ccgcgtgcaa tacaagaaga acatcgaac ggtcatataa ggtaagaccc actaccgatt    120
taacctatca ttcccacaat ctaatccact tatttctctt cccatgatct tatcctctca   180
tttctcctca ctacttttgc atttgtagga aacacaatga caccgtcgaa gaaagctggt   240
ggagcaccgt agccagcaat caccaaaaca cagaggggag gaggtcggca gcggccatgc   300
ggacggcgat gagacaacgc gacgcaaaga gggaggagga cgttggcgat catgctggtg   360
ttggcggagg aggtcactgg ccatgcgaat gacagcgggg cagcgcaaca caaaaagggg   420
```

```
ggaggatgcc ggcgaccacg ctagtaccat gaagcaagat gatgtgaaag ggaggaccgg      480
acgagggttg gacctctgcc gccgacgtga agagcgtgat gtgtagaagg agatgttaga      540
ccagatgccg acgcaactta gccctgcaag tcacccgact gcatatcgct gcttgccctc      600
gtcctcatgt acacaatcag cttgcttatc tctccatact tgtcgtttgt ttcccgtggc      660
cgaaatagaa aagacagag gtgggttttg ttggagagtt ttagtggtat tgtaggccta       720
tttgtaattt tgttgtactt tattgtatta atcaataaag gtgtttcatt ctattttgac      780
tcaatgttga atccattgat ctcttggtgt tgcactcagt atgttagaat attcattccg      840
ttgaaacaat cttggttaag ggttggaaca tttttatctg ttcggtgaaa catccgtaat      900
attttcgttg aaacaatttt tatccgacag caccgtccaa caatttacac caatttggac      960
gtgtgataca tagcagtccc caagtgaaac tgaccaccag ttgaaaggta tacaaagtga     1020
acttattcat ctaaaagacc gcagagatgg gccgtggccg tggctgcgaa cgacagcgt      1080 tcaggcccat gagccattta tttttaaaa aatatttca acaaaaaga gaacggataa        1140 aatccatcga aaaaaaaaa cttttcctacg catcctctcc tatctccatc cacggcgagc    1200
actcatccaa accgtccatc cacgcgcaca gtacacacac atagttatcg tctctccccc     1260
cgatgagtca ccaccgtgt cttcgagaaa cgcctcgccc gacaccgtac gtgcgccacc     1320
gccgcgcctg ccgcctggac acgtccggct cctctcccgc cgcgctggcc accgtccacc     1380
ggctcccgca cacgtctccc tgtctccctc cacccatgcc gtggcaatcg agctcatctc     1440
ctcgcctcct ccggcttata aatggcggcc accaccttca cctgcttgca caccacagca    1500
agagctaagt gagctagcca ctgatcagaa gaacacctcg atctctgaga gtg            1553

<210> SEQ ID NO 22
<211> LENGTH: 1087
<212> TYPE: DNA
<213> ORGANISM: Oryza sativa
<220> FEATURE:
<221> NAME/KEY: misc_feature
<223> OTHER INFORMATION: PRO0177 - Cdc2-1

<400> SEQUENCE: 22
cagacaccta gaatatagac attcccaaaa aataatcact atgcatcagc atcactatac       60
atgacttggg tctagtgatg gaagtggata gttccactac ctacataaaa acccactact      120
agtttattac ttttcacatg atagcataaa atttaaagaa aaaataaaca gaagtggaat      180
aagcgaaaaa ccccgcttac ccgccccatt tacatcccta cttggatcct gcatgtcagt      240
aagatatcag aattatatgt tttagaatta tatgtttttt tggaaggtgg aaatcggatt      300
attagacgca acataccaag tggcgtatac ttggcttcac tctttccatc agagcaagcg      360 taaagatca cgtattcacg tcacatggag taactgagcg aattttttttc attttttaaat     420 ttttgttttt taatatttac ataaatatta taccggcgaa atatttaca aaagtagacc       480 ctgctgccct tctccttctc gagaagagcg gcagggtgat gtcagggaca gaaataaact      540
ccaaaaatgc atttttggct gggcgaaaat tgcacttacc cccttgctgc cctctacaaa      600
ggttgcaagg gacctcagtg caaaatacgc acaccttgcc gtcctccact tggacggcat      660
gggctatttc tgtaaatatt ttggatggta taatatttct gtaaatatta aaaataaaa       720 atttaaaaat gaaaaattc tatctgggct cccttctctc atctcacacg gcccaccaca      780
caatcccggc ccacatattt cctgggccca tttccgtgtg aatggagacg gcccattggc    840
gcgcacatgc ggaaaagcgt acacacgatt cgaaatttga aatctcaaaa agcgcccgtt    900
```

-continued

```
agagcgcgtc ccctccaacg gctatcccca atacaaaaga tcactcgaat ccccccccaaa      960 tcgaccaaac cctaaatcca cgcgcattcc acaccaccca accagcgaga gagagatggc     1020
ggcgctccac caccaggcgg cggcggcgcc ggtgacgacg acgacggacg ggggcgagct     1080
gcgggcg                                                               1087
```

<210> SEQ ID NO 23
<211> LENGTH: 1272
<212> TYPE: DNA
<213> ORGANISM: Oryza sativa
<220> FEATURE:
<221> NAME/KEY: misc_feature
<223> OTHER INFORMATION: TC89946 (PRO0110)
<220> FEATURE:
<221> NAME/KEY: misc_feature
<222> LOCATION: (17)..(17)
<223> OTHER INFORMATION: n = any nucleotide
<220> FEATURE:
<221> NAME/KEY: misc_feature
<222> LOCATION: (50)..(50)
<223> OTHER INFORMATION: n = any nucleotide

<400> SEQUENCE: 23

```
tttgacgact gaatcgnggc tcgcctctgc ggcggccgct ctagattagn gtttcccctg       60
tctgttgtaa ttcggcacga gggctgatca agagctctta attagctagc tagtgattag      120
ctgcgcttgt gatcgatcga tctcgggtac gtagcaatgg cgtccaaggc gttcgctctg      180
ttcctggccg tgaacctcgt cgtgctcggg gtggcaagcg cctgcggcgg cagcccgtcg      240
tgcccgacgc cgacgccgtc gaccccgaca ccgtcaacgc cgacgccgac gccgtcggcg      300
ttcgggaggt gccccgcga cgcgctgaag ctgggcgtgt gcgccaacgt gctgggcctg       360
atcaaggcca aggtgggcgt gcctccggcg gagccgtgct gcccgctgct ggaggggctc      420
gtcgacctcg aggcggcggt gtgcctctgc acggccatca ggggcaacat cctcggaatc      480
aacctcaacc tccccatcga cctcagcctc atcctcaact actgcggcaa gaccgtcccc      540
accggcttca agtgctaagc agcgtgcata tgcaatgcct gcatggggttg atcctacgta     600 cggtgattag ttggcctttga cgactcttga tttgatttgc ttgctgctct gttatttgc      660 tactacgtta cgtacgtact ttgcatgcaa cgcaacgcat gatcgatcgt gcatgctggc      720
tgtttgtacg tatcacggta ccagtttgga ttctctctgt actctctcct ttgtcttctt      780
tgtagtactc ttattcccgc tatccgtacg tgcgcatttg ttgtaagggc cggtgctagc      840
ttgtgtgccg gtaccaactt ctaataaagc tatgggtgga acttcaaaaa aaataaaaaa      900
aaaactggag ggggggcccg ggtccaattt agactataat gagtttaaca ccccgctcat      960
cggccgaaga taacaacacc gggcttggaa aacctagact gcccaactaa tggacggaag     1020
acagactctt ggactgaaac tgaacgaaac aagaccaccc accccatcta accacagcca     1080
cctaccgcca aagattccaa taatgtgaat cagtcggtaa tagaacactc ctcttgtacg     1140
attttactgc ccgcgccacc cctcggtacg cacttatata tatcgggccg tagtaatttc     1200
ctggttccgt cacttccctc atcgcacctg ctagtcgtgg cttacatacg tgcgtcctct    1260
tattatcgag cg                                                       1272
```

<210> SEQ ID NO 24
<211> LENGTH: 2425
<212> TYPE: DNA
<213> ORGANISM: Oryza sativa
<220> FEATURE:
<221> NAME/KEY: misc_feature
<223> OTHER INFORMATION: TC90358 (PRO0005)
<220> FEATURE:
<221> NAME/KEY: misc_feature
<222> LOCATION: (1558)..(1558)
<223> OTHER INFORMATION: n = any nucleotide

<400> SEQUENCE: 24

| | | | | | |
|---|---|---|---|---|---|
| cccacattga | ataattattt | taaataattt | aagtttttt | tttttggctt | tagatatatt | 60 |
| cccaatcccc | aacctcccaa | taatccgatc | tctcccagtt | ctgttcggat | caaggctgtg | 120 |
| tcgatcgcaa | aaagaaaaa | aaaaacaatt | tccttttggg | gtggttcatc | tgttgatcac | 180 |
| ttctttgttt | cccgcgtttt | gttgggatt | cgattttcgg | gttaagattt | tctacacgat | 240 |
| ggccttgaac | ttggctcaga | gcgccgcggc | ggcagcgtgc | ttcgcgaccg | ccggtgatgc | 300 |
| gcggcgagct | gcttcggtgg | tcgccatgcc | gtcgtcgtcg | tcgtcggcca | cgacgagcct | 360 |
| gaggatgaag | aggcaggcgg | cgtgcgagcc | ggtggcgtgc | cgggcggtgg | ccaggcacgt | 420 |
| ggcggcggcg | gcggcgagca | gcaggaggaa | cggcgtgccg | gtgttcgtga | tgatgccgct | 480 |
| ggacacggtg | agcaagtgcg | ggagcgcgct | gaaccggagg | aaggcggtgg | cggcgagcct | 540 |
| ggcggcgctg | aagagcgccg | gcgtggaggg | gatcatggtg | gacgtgtggt | ggggcatcgt | 600 |
| ggagagcgag | ggccccggcc | ggtacaactt | cgacggctac | gtggagctca | tggagatggc | 660 |
| ccgcaagacc | ggcctcaagg | tccaggccgt | catgtccttc | caccagtgcg | gcggcaacgt | 720 |
| cggcgactcc | gtcaacatcc | cgctcccgag | gtgggtggtg | gaggagatgg | agaaggacaa | 780 |
| cgacctcgcc | tacaccgacc | aatggggacg | ccgcaacttc | gagtacatct | ccctcggctg | 840 |
| cgacgccatg | cccgtcttca | agggccgcac | gcccgtcgag | tgctacaccg | acttcatgcg | 900 |
| cgccttccgc | gaccacttcg | cctccttcct | cggcgacacc | atcgtcgaaa | tccaagtcgg | 960 |
| catgggcccc | gccggcgagc | ttcggtaccc | gtcctacccg | gagagcaacg | gcacctggag | 1020 |
| gttccccggc | atcggcgcct | tccaatgcaa | cgacaggtac | atgcgtagca | gcctgaaggc | 1080 |
| ggcggcggag | gcgaggggca | agccggtagt | ggggccacgg | cgggccgacg | gacgccggcg | 1140 |
| gctacaacaa | ctggccggaa | gacacggtgt | tcttccgcgg | cgactgcggc | gggtggagca | 1200 |
| ccgagtacgg | cgagttcttc | ctgtcgtggt | attcgcagat | gctgctggag | cacggcgagc | 1260 |
| gcgtgctgtc | gggcgcgacg | tccgtgttcg | gcgacggcgc | cggcgccaag | atctcggtca | 1320 |
| aggtggccgg | catccactgg | cactacggca | cgcggtcgca | cgcgccggag | ctcacggcgg | 1380 |
| ggtactacaa | cacgcggcac | cgcgagcggc | tacctcccga | tcgcgcgcat | gctggcgcgc | 1440 |
| cacggcgccg | tgctcaactt | cacctgcgtg | gagatgcgcg | accacgagca | gccgcaggag | 1500 |
| gcgcagtgca | tgcccgaggc | gctcgtcagg | caggtggccg | ccgcggcgcg | cgcggcgnga | 1560 |
| cgtcgggctc | gccggggaga | acgcgctgcc | gcggtacgac | ggcacggcgc | acgaccaggt | 1620 |
| ggtcgccgcc | gccgccgacc | gcgcggcgaa | ggaccggatg | gtcgccttca | cctacctccg | 1680 |
| gatgggcccc | gacctcttcc | acccggacaa | ctggcgccgg | ttcgtcgcct | tcgtccgccg | 1740 |
| catgtccgag | tccggctcgc | cgcggaggc | cgccgagagc | gccgcgcacg | gcgtcgcgca | 1800 |
| ggccaccggc | tcgctcgtgc | acgaggccgc | ggtcgcgctc | cggagctagc | accggtcaga | 1860 |
| cgctcatata | caccgtcgcc | tcgaggtcgg | attccgatgt | gggatcattc | gatctccctt | 1920 |
| ttttttttct | tcttttttgcc | attttgtaca | gccttttggg | gagctttgga | tttgtgcttt | 1980 |
| ttgtctcggg | aggaaaaccg | ctctggaggt | cgaagagagc | gtcatttcc | tcccgttgaa | 2040 |
| gatcacgaat | catttacgtt | agagatgatg | taattaagca | ggagggag | gggaacacac | 2100 |
| acacactggc | actcaaaagt | tgttgtcacg | cttggggaat | atatccattt | ccagccaaaa | 2160 |

```
aaaaaacgca gaaatgcgtt gtgttcttgc gctctggttc gttgctgctg tgggtcagat    2220
tcagctggtg aaaaaactac agtactactg aaactgaaac tactagagcc tagagggaga    2280
ttaagctaag ttaattgcac gagtaattac tccacggttg tgtttagggt ctacgtcggc    2340
agattttgct ttctggtaga tccctaacct tatgtttgtt gggaatttta taaggagct     2400 aagtttgcct attgatttgc aatct                                          2425
```

<210> SEQ ID NO 25
<211> LENGTH: 3410
<212> TYPE: DNA
<213> ORGANISM: Oryza sativa
<220> FEATURE:
<221> NAME/KEY: misc_feature
<223> OTHER INFORMATION: TC83635 (PRO0009)

<400> SEQUENCE: 25

```
ccatggacac cgcctccgtc accggtggcg agcacaaggg gaaggagaag acgtgccggg      60
tgtgcggcga ggaggtggcg gcgagggagg acggaagcc gttcgtggcg tgcgccgagt     120
gcggcttccc ggtgtgcaag ccctgctacg agtacgagcg cagcgagggc acccagtgct    180
gcccccagtg caacacccgc tacaagcgcc acaaggggtg cccacggtg gaaggcgacg     240 aggacgacgg cggcgacatg gacgacttcg aggaggagtt ccagatcaag agccccacca    300
agcagaaacc ccccacgag cccgtcaact tcgacgtcta ctcggagaac ggcgagcagc     360
cggcacagaa gtggcgccct ggaggcccgg cgctctcttc cttcaccgga agcgtggctg    420
ggaaggatct ggagcaggag agggagatgg agggtggcat ggagtggaag gacaggatcg    480
acaagtggaa gacgaagcag gagaagcggg gcaagctcaa ccgcgacgac agcgacgacg    540
acgacgacaa gaacgacgac gagtacatgc tgctcgcgga ggcgaggcag ccgctgtgga    600
ggaaggtgcc gatcccgtcg agcaagatca acccgtaccg gatcgtgatc gtgctccggc    660
tggtggtgct ctgcttcttc ctcaagttcc ggatcacgac gccggcgatg gacgcggtgc    720
cgctgtggct ggcctcggtg atctgcgagc tgtggttcgc gctgtcgtgg atcctcgacc    780
agctgcccaa gtggtcgccg gtgacgaggg agacgtacct ggaccggctg ccctccggt     840 acgagcgcga cggcgagccg tgccgcctgg ccccgatcga tttcttcgtc agcacggtgg    900
acccgctcaa ggagccgccc atcatcaccg ccaacaccgt gctgtccatc ctcgccgtcg    960 actacccgt cgaccgcgtc tcctgctacg tctccgacga cggcgcgtcc atgctgctct    1020
tcgacacgct ctccgagacc gccgagttcg cccgccggtg ggtcccctcc tgcaagaagt    1080
tcaccatcga gccccgcgcc cccgagttct acttctccca gaagatcgac tacctcaagg    1140
acaaggtcca gcccaccttc gtcaaagaac gccgcgccat gaagagagag tatgaggagt    1200
tcaaggtgag gataaacgcg ctggtggcga aggcgcagaa gaagccggag aagggtggg     1260 tgatgcagga cggacgcca tggccgggga caacacgag ggaccacccg gggatgatcc      1320
aggtgtacct gggcagccag ggcgcgctcg acgtcgaggg cagcgagctg ccgcggctgg    1380
tgtacgtgtc ccgcgagaag cggcccggct acaaccacca agaaggcc ggcgccatga      1440 actccctcgt tcgcgtctcc gccgtgctta ccaacgcccc cttcatcctc aacctcgact    1500
gcgaccacta cgtcaacaac agcaaggccg tccgcgaggc catgtgcttc ctcatggaca    1560
agcagctcgg caagaagctg tgctacgtcc agttccccca gcgcttcgac ggcatcgacc    1620
gccacgatcg ctacgccaac cgcaacaccg tcttcttcga catcaacatg aaggggctgg    1680 acgggatac ggggccggtg tacgtgggga cggggacggt gttcaacagg caggcgctgt     1740
```

-continued

```
acggatacga cccgccgcgg ccggagaaga ggccgaagat gacgtgcgac tgctggccgt    1800
cgtggtgctg ctgctgctgc tgcttcggcg gggggaagcg cggcaagtcg cacaagaaca    1860
agaagggcgg cggcggcggc gagggcggcg gcctcgacga gccgcgccgc gggctgctcg    1920
ggttctacaa gaagaggagc aagaaggaca agctcggcgg cggcgcggcg tcgctcgccg    1980
gagggaagaa agggtaccgg aagcaccagc gcgggttcga gctggaggag atcgaggagg    2040
gcctcgaggg gtacgacgag ctggagcgct cgtcgctcat gtcgcagaag agcttcgaga    2100
agcggttcgg ccagtcgccg gtgttcatcg cctccaccct cgtcgaggac ggcggcctcc    2160
cccagggcgc cgccgccgac cccgccgccc tcatcaagga ggccatccac gtcatcagct    2220
gcggctacga ggagaagacc gagtgggggca aggagattgg gtggatctac ggtcggtga    2280 cggaggacat cttaacgggg ttcaagatgc attgccgtgg gtggaagtcg gtgtactgca    2340
cgccggcgag ggcggcattc aaggggtcgg cgcccatcaa cctgtcggat cgtctgcacc    2400
aggtgctccg gtgggcgctc ggctccgtcg agatcttcat gagccgccat tgcccgctct    2460
ggtaccctat ggcggccgcc tcaagtggct cgagcgcttc gcctacacca acaccatcgt    2520
ctaccccttc acctccattc ccctcctcgc ctactgcacc atccccgccg tctgcctcct    2580
caccggcaag ttcatcatcc ccacgcttaa caatttggcg agcatatggt tcatagcgct    2640
tttcctgtcg atcatcgcga cggggggtgct ggagctgcgg tggagcgggg tgagcatcga    2700
ggactggtgg aggaacgagc agttctgggt gatcggcggc gtgtcggcgc acctgttcgc    2760
cgtgttccaa ggcctcctca aggtgctcgg cggcgtggac accaacttca cggtgacgtc    2820
caaagccgcc gccgacgaag accgacgcgt tcggcgagct ctaactgttc aagtggacga    2880
cgctgctggt gccgccgacg acgctgatca tcatcaacat ggtggggatc gtcgccggcg    2940
tgtcggacgc cgtgaacaac gggtacgggt cgtggggccc gctgttcggg aagctcttct    3000
tctccttctg ggtcatcctc cacctctacc ccttcctcaa ggggctcatg gggaggcaga    3060
accggacgcc cacaattgtc gtgctctggt ccaacctcct cgcctccatc ttctccctcg    3120
tctgggtcag gatcgacccc ttcatcccca gcccaagggg cccgtcctc aagccatgcg    3180 gggtctcgtg ctgagctgct gctgctactt ctctgtgtct ctgcatttg caagagggat    3240 gaccggatgg atgattcttg ttgtatggag tattttgact tgttcatgta caagtttttg    3300
tgagtgggat aaaagtgttt tgggggtaaa atttgtaaga actgaggtgg agattatact    3360
cgaatttaag aacaattgtt tttgaatttt cttttaagat ttttgggagt               3410
```

<210> SEQ ID NO 26
<211> LENGTH: 602
<212> TYPE: DNA
<213> ORGANISM: Oryza sativa
<220> FEATURE:
<221> NAME/KEY: misc_feature
<223> OTHER INFORMATION: TC83117 (PRO0058)

<400> SEQUENCE: 26

```
ccccccctc gaggttcgac ccactcgtcc gctgacggtt agttccaagg gaaagaagaa      60
atggaggctt cacgcaaggt gttctcggcc atgcttctca tggtgctgct gcttgcagcc    120
actggtgaga tgggcgggcc ggtgatggtg gcggaggctc ggacgtgcga gtcgcagagc    180
caccggttca agggcccgtg cgcccgcaag gcgaactgcg ccagcgtatg caacacggag    240
ggcttccccg acggctactg ccacggcgtc cgccgccgct gcatgtgcac caagccctgc    300
ccctgatcga tgaaccagca gctagcgcag cagcttgtgc cgccacctcg cgcatgtgtc    360
```

```
atcgtgtcga tcgatcggat cctagctgcc ctatgaatga ataaaagtgt gtggcttatg      420
cgtggttttc tcttggagaa ctttggcttt tgtggtgtta agttcgatcg ttttgtgcat      480
ccaccatcca tccatcctcc cattctgctt gttctaaggt tatactacta cttgagaagg      540
tgatgcaatt gtgctcaaca gtttattaat acttcatccg ttttaaaatg tttgaccccg      600
tt                                                                     602
```

<210> SEQ ID NO 27
<211> LENGTH: 1170
<212> TYPE: DNA
<213> ORGANISM: Oryza sativa
<220> FEATURE:
<221> NAME/KEY: misc_feature
<223> OTHER INFORMATION: TC89913 (PRO0061)
<220> FEATURE:
<221> NAME/KEY: misc_feature
<222> LOCATION: (15)..(16)
<223> OTHER INFORMATION: n = any nucleotide
<220> FEATURE:
<221> NAME/KEY: misc_feature
<222> LOCATION: (1162)..(1162)
<223> OTHER INFORMATION: n = any nucleotide

<400> SEQUENCE: 27

```
aattcggcac gagannaaaa ggaaaaaaaa acaaaacaca ccaagccaaa taaaagcgac       60
aatgggatcg ctcaccacca acatcgtcct cgccgtcgcc gtggtggcag cgctggtcgg      120
cggcgggtcg tgcggcccgc ccaaggtgcc acccggcccg aacatcacga ccaactacaa      180
cgccccgtgg ctccccgcca gggccacctg gtacggccag ccctacggct ccggctccac      240
cgacaatggt ggcgcgtgcg ggatcaagaa cgtcaacctg cctccctaca cggcatgat      300 ctcctgcggc aacgtcccaa tcttcaagga cggcagggga tgcggctcat gctacgaggt      360
gaagtgtgag cagccggcgg cgtgctcgaa gcagccggtg acggtgttca tcacggacat      420
gaactacgag cccatctcgg cgtaccactt cgacttctcc ggcaaggcgt tcggcgccat      480
ggcttgcccg gggaaggaga ccgagctccg caaggccggc atcatcgaca tgcagttcag      540
gagggtgcgc tgcaagtacc ccggcggcca gaaggtcacc ttccacgtcg agaagggctc      600
caaccccaac tacctcgccg tgctcgtcaa gttcgtcgcc gacgacggtg acgtcatcca      660
gatggacctc caggaggccg gattgccagc gtggaggccc atgaagctgt cgtggggcgc      720
catctggagg atggacaccg ccacgccact caaggcaccc ttctccattc gcgtcaccac      780
cgagtccggc aagagcctca tcgccaaaga cgtcatcccg gtcaactgga tgccagacgc      840
catctacgta tcaaacgtcc agttctattg agatcggacg gaaacgatcc tcctaattta      900
tttccctatt aatttgttca aatggtttcc ttctataacc tatatttttc ccgttgttag      960
aaatggttcc atttcctcct acagcttact ttaagatagt tgcgcttgta tatctgcgcc     1020
atcttgtaag ttgtaagatg ctgaagaaca ctatgaattc tgagcatctg attctccggg     1080
aagatttact atgataaaca acagtttgat ttactatgtg tgtcccttg tttattgtat      1140 gctatcctaa tacttatgaa angttttgat                                      1170
```

<210> SEQ ID NO 28
<211> LENGTH: 861
<212> TYPE: DNA
<213> ORGANISM: Oryza sativa
<220> FEATURE:
<221> NAME/KEY: misc_feature
<223> OTHER INFORMATION: TC89985

<400> SEQUENCE: 28

```
ccacgcgtcc gcccacgcgt ccgcgatcag cagcagcagc agcttgcaca ctcgagctta      60
gcttagcttt tgcaagagag atcgagctag agatggagaa gtcgagcaag atgatggcgg     120
tggcggcggt gctggtgctc gcggtggtcg gcgcggcgga ggcgaggaac atcaaggcgg     180
cggcggcggc ggcggcggag agcaaggaca cggtggtgca gccgacgacg ttcccgccgt     240
tcgaccgctt cgggagcgcg gtgccggcgt tcggcggcat gccggcagc agcatcccgg      300
ggttcagcct ccccggcagc agcggctcca ccccggcgg cctcggcggc ttcggcagca      360
tgcccatgtt cggcggcctc ggcggcggct cacctggcct cggcggcggc atgcccggct     420
ccccccgccg cgccgacaag caggccaaga agccatgaga gacctcgccg tcgccggcgg     480
cgtcgccgct gctgcgcggg taatgtgctc tatgtagcgc acggcgttgc atgcaatatg     540
gatggctata tgacgcgcgc gcgttatatc ttcatatgtg cagttagctt gcactgtgtc     600
tagctagcgt tctattatga gtagtgtctc ttctatctct tttctttaca tgcatttgga     660
ggaggattat tctatctgtt tgttggttgg ttgtgtttgt ttgttttaat taggtccctt     720
cttatatttt gtgttttaat taagttcgtg atcatgtagt agtactacca ctgtttcgag     780
ctcgaggcat gaataatgct aaatgtgatc attattgtgt tattgtatgg tgatggctat     840
atatattact atctctgctt c                                               861
```

<210> SEQ ID NO 29
<211> LENGTH: 1252
<212> TYPE: DNA
<213> ORGANISM: Oryza sativa
<220> FEATURE:
<221> NAME/KEY: misc_feature
<223> OTHER INFORMATION: TC89891 (PRO0081)
<220> FEATURE:
<221> NAME/KEY: misc_feature
<222> LOCATION: (5)..(5)
<223> OTHER INFORMATION: n = any nucleotide

<400> SEQUENCE: 29

```
cccangcgtc cgaaccaatc gactcgcacc accaccagca gctcaagcag caacagctca      60
aacggaggaa gatctcatcg ccatgacgac cggcaatggc gacgcaccgg tgatcaagaa     120
cgcccacagc gacatcgaca gcaccaacaa gacgctgctc aagagcgacg ccctgtacaa     180
gtatgtcctg gacacgacgg tgctgccacg ggagccggag tgcatgcgcg atctgcgcct     240
catcacggac aagcaccagt gggggttcat gcagtcgtcg gcggatgagg cgcagtgctg     300
gggatgctgc tgaagatggc cggagcgaag aggacaatcg aggtgggtgt cttcaccggc     360
tactcgctgc tggcgacggc gctggcgctg ccggaggacg ggaaggtggt ggcgatcgac     420
ccggacaggg agagctacga gatcgggcgg ccgttcttgg agaaggccgg ggtgcgcac      480
aaggtggact ccgcgaggg gaaggggctg gagaagctgg acgagctgct cgccgaggag     540
gcggcggcgg ggcgcgaggc ggcgttcgac ttcgcgttcg tggacgcgga caagcccaac     600
tacgtcaagt accacgagca gctgctgcag ctggtgcgcg tcggcgggca catcgtgtac     660
gacaacacgc tgtgggccgg cacggtggcg ctgccgccgg acacgccgct gtcggacctg     720
gaccggaggt tctccgtcgc catcaggac ctcaactcca ggctcgccgc cgacccgcgc      780
atcgacgtct gccagctcgc catcgccgac ggcatcacca tctgccgccg cctcgtgtga     840
ggtcgagacc gagaccttac cggccgatcc atccatcgct ctcgcgtgat taattaacgt     900
gtgttgctgt actcttctac tgctacaact atactattac ttccttaatt gccgcttaaa     960
```

-continued

| | |
|---|---|
| ttttcctata cgtgtttcaa tcaatgagat tattatattc ttcgagcatg agagagacgg | 1020 |
| agttgtaggg acatttgatg atggttgtta ctgtactaca tgttgataag tgcaacatct | 1080 |
| ctttccatgg ttgctactct actcaccgtg tcatgttggt tgcggatttt gatctcatct | 1140 |
| gcaagatgga ctactggggc ccaaaatgga acagactggt ccctcgatcc tgcaggagct | 1200 |
| tgcacctgtt gcaagggcct ttttaactgg ctaactaggt gggtaagtag gg | 1252 |

```
<210> SEQ ID NO 30
<211> LENGTH: 671
<212> TYPE: DNA
<213> ORGANISM: Oryza sativa
<220> FEATURE:
<221> NAME/KEY: misc_feature
<223> OTHER INFORMATION: TC89670 (PRO0091)
<220> FEATURE:
<221> NAME/KEY: misc_feature
<222> LOCATION: (3)..(3)
<223> OTHER INFORMATION: n = any nucleotide
<220> FEATURE:
<221> NAME/KEY: misc_feature
<222> LOCATION: (14)..(14)
<223> OTHER INFORMATION: n = any nucleotide

<400> SEQUENCE: 30
```

| | |
|---|---|
| gcnggcttcg gcangagttc aaacattata gttgaagcat agtagtagaa tcctacaaaa | 60 |
| atgaagatca ttttcgtatt tgctctcctt gctattgttg catgcaacgc ttctgcacgg | 120 |
| tttgatgctc ttagtcaaag ttatagacaa tatcaactac aatcgcatct cctgctacag | 180 |
| caacaagtgc tcagcccatg cagtgagttc gtaaggcaac agcatagcat agtggcaacc | 240 |
| cccttctggc aaccagctac gtttcaattg ataaacaacc aagtcatgca gcaacagtgt | 300 |
| tgccaacagc tcaggctggt agcgcaacaa tctcactacc aggccattag tagcgttcag | 360 |
| gcgattgtgc agcaactaca gctgcagcag gtcggtgttg tctactttga tcagactcaa | 420 |
| gctcaagctc aagctttgct ggccttaaac ttgccatcca tatgtggtat ctatcctaac | 480 |
| tactacattg ctccgaggag cattcccacc gttggtggtg tctggtactg aattgtaata | 540 |
| gtataatggt tcaaatgtta aaaataaagt catgcatcat catgcgtgac agttgaaact | 600 |
| tgatgtcata taaatctaaa taaaatcacc tatttaaata gcattcatgt atgagttcca | 660 |
| ttatcatagc t | 671 |

```
<210> SEQ ID NO 31
<211> LENGTH: 436
<212> TYPE: DNA
<213> ORGANISM: Oryza sativa
<220> FEATURE:
<221> NAME/KEY: misc_feature
<223> OTHER INFORMATION: TC89883 (PRO0095)

<400> SEQUENCE: 31
```

| | |
|---|---|
| cctcgagggt cgacccacgc gtccgctctc ctctcttctc tcgccctcac cgctcgccga | 60 |
| ggttgccgtc tccttgtctc ctccgctcct tgcgccgccg ccgcgacgag tcgcggggag | 120 |
| gggcggcgat ctccatctcc atctgaggcg aggagagcag gggaggtgag gggatcctgg | 180 |
| tgaggtttgt gattactgga caatagaaat atttacacaa tatggctggc ggctctgctg | 240 |
| atgcagtgac caaggagatg gaggcgctac tcgttggaca aaatccaaat gcggttagtg | 300 |
| gagaaacatg cgagacctca tcaaaagaag gcaaagttgc agatagcaat ggatctcatt | 360 |
| cttcaccacc agaagatgat gatgatgaag cgcaagggga tggtccatct caagattgga | 420 |
| ggatccagaa gctttc | 436 |

<210> SEQ ID NO 32
<211> LENGTH: 860
<212> TYPE: DNA
<213> ORGANISM: Oryza sativa
<220> FEATURE:
<221> NAME/KEY: misc_feature
<223> OTHER INFORMATION: TC90434 (PRO0111)
<220> FEATURE:
<221> NAME/KEY: misc_feature
<222> LOCATION: (1)..(1)
<223> OTHER INFORMATION: n = any nulceotide
<220> FEATURE:
<221> NAME/KEY: misc_feature
<222> LOCATION: (10)..(10)
<223> OTHER INFORMATION: n = any nulceotide

<400> SEQUENCE: 32

```
nagggctaan attaccggag tattttttgca aagggagtaa tcaaagttcc aatacgaaat      60
cgcggtcgta gtagtacaat acaaagacga gttcacggag cgcgtaaact aataaggaaa     120
aattaaacgt cgcggagaaa taatagccga actggatgaa gatgagcagc actgcctctt     180
gcctagccta gcccatcatg gcgaggccga cggccccgac cagcaggccc atcaccgaac     240
gggcctcgct gccgctggcc ccgccggtgc tgcccgtcga cttcgtcgtc gtcgtcgtcg     300
gcgtcgtggt cgcgtccggc gtcgacgagg gcgtgtccat gccggggtcc gatgacggcg     360
tggcgggcgt cgcggtggac ggcggggacg acgacgccgt cggggtgggg gtggtgccgg     420
ccgccgcgga ccgtgacg gcgagcttca tgccgccgga gcagtggccg ctggtgccgc      480
agatgaagta gcgggtgccg ggcttggtga gcgcgatctt ggtgttctgg tcgctgtagg     540
actggatcga gttgctggcg gacacgcgct gtagtcagcc gagctcacct ccgccaccgt     600
gtgcatcatg ctgtactgga acacgagcga gtcaccaacg ctgaaggttt tgctcttcgc     660
ccaggtatcg tagtccacgc cactgctcca gccggatgtg tcgccgacgg tgtagtccac     720
ggcgaaagcc ggcgcaacgg cggcgaggag tagcaccacc agacctgcag ctgcaagtcc     780
atgtactcca gccatgatgg cagagttaat tagcaaacgc gaactgatta gagccgtact     840
agtactggtg gccctcgtgc                                                 860
```

<210> SEQ ID NO 33
<211> LENGTH: 1167
<212> TYPE: DNA
<213> ORGANISM: Oryza sativa
<220> FEATURE:
<221> NAME/KEY: misc_feature
<223> OTHER INFORMATION: TC83072 (PRO0116)

<400> SEQUENCE: 33

```
aggaaaagaa gaaaaaagat cctgtgaacc ctacgaaact accgaagcga acggaaggca      60
ggaatcggcg gcggcggcgg cggcggcggt ggggagaagc catggagcgg ctgcagcgga     120
tcttcggcgc ctccggcatg gggcagccgc cgtcggactc gccgctgctc gactcctccg     180
agcaggtcta catctcctcc ctcgccctcc tcaagatgct caagcacggg agggccggcg     240
tgccgatgga ggtgatgggg ctgatgctgg gggagttcgt cgacgactac acggtcaggg     300
tggtcgacgt cttcgccatg ccgcagagcg ggaccggggt cagcgtcgag gccgtcgacc     360
atgtcttcca gaccaacatg ctcgacatgc tcaagcagac cgggaggcca gaaatggtgg     420
taggttggta ccattcccat cctggatttg gttgctggct tcaggagtt gacatcaata     480
ctcaacagag ttttgaagct ttaaacccca gggcagttgc cgtcgtgata gatcccatcc     540
```

```
aaagtgtcaa ggggaaagtt gtcattgatg catttcgcct tattaaccct cagaccatga      600
tgcttggtca ggagccacga cagacaacat caaatgttgg gcacctaaat aagccatcta      660
ttcaggctct tattcatggg ctgaacaggc actactattc aattgcaatc aattaccgga      720
aaaatgagct tgaggaaaag atgttactga acttgcacaa aaagaaatgg accgatggat      780
tgattctgaa gaggtttgac actcattcaa agaccaatga gcagactgtt caggaaatgc      840
tgaaccttgc tatcaagtac aacaaggcgg tgcaagagga ggatgagctg ccgcctgaga      900
aattagcgat agcaaatgtg ggacggcaag atgctaagaa gcacttggaa gagcatgtct      960
ccaatttgat gtcatcaaac atagttcaga cgctaggaac catgctcgat acagttgtat     1020
tttagatcac tactgctgtt atcccaacac tgtacccaga gctcgtttat tttttatttt     1080
tttatgttta tcgaagccta ccataattca gtgaacttaa cgccagttac atttgggtta     1140
tgaaagctta ccacttgaca acttcat                                         1167

<210> SEQ ID NO 34
<211> LENGTH: 871
<212> TYPE: DNA
<213> ORGANISM: Oryza sativa
<220> FEATURE:
<221> NAME/KEY: misc_feature
<223> OTHER INFORMATION: TC90038 (PRO0117)

<400> SEQUENCE: 34
cctagctcct cccgccgccg ccgccgccgc cgccgccgcc tctccactcg agagacccag       60
ccgccgccgc cgccgccgcc gccatgtcgc tgatcgccgg ggaggacttc cagcacatcc      120
tgcgtctgct gaacaccaac gtcgatggga agcagaagat catgttcgcg ctcacctcca      180
tcaagggtgt cggccgcagg ttctccaaca tcgcctgcaa gaaggccgac atcgacatga      240
acaagagggc cggtgagctt acgccggagg agctggagcg gctgatgacc gtggtggcga      300
acccgcggca gttcaaggtg cccgactggt cctcaacag gaagaaggac tacaaggacg      360
ggaggttctc ccaggttgtc tccaacgcgc tcgacatgaa gctcagggat gatcttgaga      420
ggctcaagaa gatcaggaac caccgtggtc tgaggcacta ctgggcctc cgtgtgcgtg      480 ggcagcacac caagacaacc ggaaggaggg gtaagactgt cggtgtgtcc aagaagcgat      540
aagcctaaga accacccgag acttgatgaa gcgtttcgtt gggtgatgtt ttgccctagg      600
ataatatttt gcagctatgg aaccttgtcg taatgtatct tgaagagtgt ctttgggaac      660
taagagtaat ttacttttct tgaaactatt gcagtattga ctccttgttt attgcttttc      720
tccactttct tctacccact taaaactatt gcagtatcga ctccttgttt attgctattc      780
tccactggct tctgccttaa ttttggatgt tgcatgcgct gtgtatctgg ttcatgtgat      840
gtacccatgg cagctttgat gcattgggat t                                    871

<210> SEQ ID NO 35
<211> LENGTH: 1245
<212> TYPE: DNA
<213> ORGANISM: Oryza sativa
<220> FEATURE:
<221> NAME/KEY: misc_feature
<223> OTHER INFORMATION: TC82936 (PRO0122)

<400> SEQUENCE: 35
acgcggccaa aacgtaccct tgtgactaca cccgcttcgc ttcctcccct ctctaagccg       60
gggaagctaa gccatggcgt ccgtcaccgc ccgcaccccg gtcgcagccc tccgctcgtc      120
ggcgtcgctc aagtctacct tcctagggca atcctccacc cgcctcgccc gcgcaccgac      180
```

```
tacgaggcgt aatgttcggg cggaggccaa gggagagtgg ctccccggcc tcccttctcc    240
cacctacctc aacggcagct tgccaggcga taacgggttc gacccgttgg gtctggcgga    300
ggacccggag aacctgcggt ggttcgtgca ggcggagtgg tgaacgggcg gtgggcgatg    360 ctggggtgg ccgggatgct gctgcctgag gtgctgacga agatcgggtt gatcgacgcg    420
ccgcagtggt acgacgccgg caaggccacc tacttcgcgt cgtcgtcgac gctgttcgtc    480
atcgagttca tcctgttcca ctacgtggag atccggcgt ggcaggacat caagaaccct    540
ggctgcgtca accaggaccc catcttcaag agctacagcc tcccgccgca cgagtgcggc    600
taccccggca gcgtcttcaa cccctcaac ttcgagccca cctcgaggc caaggagaag    660 gagctcgcca acgggaggct ggcgatgctg gcgttcttgg ggttcctggt gcagcacaac    720
gtgacgcaga gggggcctt cgacaacctg ctgcagcacc tgtctgaccc gtggcacaac    780
accatcatcc agacgctgtc aggctgagcg tgtgatcgat ttcatcaggg ccagggcatc    840
tcaaggagct tgatgagttc aggctggtga accgatgat tgggcgatgg aagatgttct    900
cttcttgttt cttcttttt ttttgtgga gtatgcatgt ataagatgtt aatgaattgg    960
ggggaggaga gagagagaga tggatgtgat gagattcaga cttactgtgt gtgttgtggt   1020
aattgtttcc tgcatgcatg gatctggatg catgggtgag ggggtgagtt gagtggtgaa   1080
tttctgatgt acagtactac aggggataa actatctcat ggtagcagca gtgttctagc   1140
tatctcatgg tctcgatctt aattatggtg gataaactac gcttaattgc ttgtcaagtg   1200
cttcatttgc gcattgattc agtattgcgt atcgattcaa agacc                  1245

<210> SEQ ID NO 36
<211> LENGTH: 1416
<212> TYPE: DNA
<213> ORGANISM: Oryza sativa
<220> FEATURE:
<221> NAME/KEY: misc_feature
<223> OTHER INFORMATION: TC89839 (PRO0123)

<400> SEQUENCE: 36
cccacgcgtc cgcccacgcg tccgggacac cagaaacata gtacacttga gctcactcca     60
aactcaaaca ctcacaccaa tggctctcca agttcaggcc gcactcctgc cctctgctct    120
ctctgtcccc aagaagggta acttgagcgc ggtggtgaag gagccggggt tccttagcgt    180
gagcagaagg ccaagaagcc gtcgctggtg gtgagggcgg tggcgacgcg gcgggccggt    240
ggcgagcccc ggcgcgggca cgtcgaaggc ggacgggaag aagacgctgc ggcagggggt    300
ggtggtgatc accggcgcgt cgtcggggct cgggctcgcg gcggcgaagg cgcttggcgg    360
agacggggaa gtggcacgtg gtgatggcgt tccgcgactt tcctgaaggc ggcgacggcg    420
gcgaaggcgg cggggatggc ggcggggagc tacaccgtca tgcacctgga cctcgcctcc    480
ctcgacagcg tccgccagtt cgtggacaac ttcggcgct ccggcatgcc gctcgacgcg    540
ctggtgtgca acgccgcaca tctaccggcc gacggcgcgg caaccgacgt tcaacgccga    600
cgggtacgag atgagcgtcg gggtgaacca cctgggccac ttcctcctcg cccgcctcat    660
gctcgacgac ctcaagaaat ccgactaccc gtcgcggcgg ctcatcatcc tcggctccat    720
caccggcaac accaacacct tcgccggcaa cgtccctccc aaggccgggc taggcgacct    780
ccgggggctc gccggcgggc tccgcggca gaacgggtcg gcgatgatcg acggcgcgga    840
gagcttcgac ggcgccaagg cgtacaagga cagcaagatc tgtaacatgc tgacgatgca    900
ggagttccac cggagattcc acgaggagac cgggatcacg ttcgcgtcgc tgtacccggg    960
```

```
gtgcatcgcg acgacgggct tgttccgcga gcacatcccg ctgttccggc tgctgttccc    1020
gccgttccag cggttcgtga cgaagggatt cgtgtcggag gcggagtccg ggaagcggct    1080
ggcgcaggtg gtgggcgacc cgagcctgac caagtccggc gtgtactgga gctggaacaa    1140
ggactcggcg tcgttcgaga accagctctc gcaggaggcc agcgacccgg agaaggccag    1200
gaagctctgg gacctcagcg agaagctcgt cggcctcgtc tgagtttatt atttacccat    1260
tcgtttcaac tgttaatttc ttcggggttt aggggggttc agctttcagt gagagaggcc    1320
tgtcaagtga tgtacaatta gtaattttt tttacccgac aaatcatgca ataaaaccac    1380
aggcttacat tatcgatttg tccacctaaa ttaagt                              1416

<210> SEQ ID NO 37
<211> LENGTH: 1149
<212> TYPE: DNA
<213> ORGANISM: Oryza sativa
<220> FEATURE:
<221> NAME/KEY: misc_feature
<223> OTHER INFORMATION: TC85888 (PRO0133)

<400> SEQUENCE: 37
cttctacttc tatcatacca aacaaactag cttaatttgc attgcatcac attgccggcc     60
gccatgagag ctctcgctct cgcggtggtg gccatggcgg tggtggccgt gcgcggcgag    120
cagtgcggca gccaggccgg cggcgcgctc tgccccaact gcctctgctg cagccagtac    180
ggctggtgcg gctccacctc cgattactgc ggcgccggct gccagagcca gtgctccggc    240
ggctgcggcg gcggccccgac cccgcccctcc agcggtggcg gcagcggcgt cgcctccatc    300
atatcgccct cgctcttcga ccagatgctg ctccaccgca acgaccaggc gtgcgccgct    360
aagggcttct acacctacga cgccttcgtc gccgccgcca acgcctaccc ggacttcgcc    420
accacccgcg acgccgacac ctgcaagcgc gaggtcgccg ccttcctggc gcagacgtcc    480
cacgagacca ccggcggctg gcccacgggc ccgacggcc cctactcctg gggctactgc    540
ttcaaggagg agaacaacgg caacgccccc acatactgcg agcccaagcc ggagtggccg    600
tgcgccgccg cgaagaagta ctacggccgg ggacccatcc agatcaccta caactacaac    660
tacggccgcg gggcaggcat cggctccgac ctgctcaaca cccggaccct ggtggcgtcg    720
gacgccagtc tccttcaaga cggcgttctg gttctggatg acgccgcagt cgcccaagcc    780
gtcgtgccac gcggtgatca ccggccagtg gacgccgtcc gccgacgacc aggcggcggg    840
gcgcgttccg ggctacggcg agatcaccaa catcatcaac ggcggtgtgg agtgcgggca    900
cggcgcggac gacaaggtgg ccgaccggat cgggttctac aagcgctact gcgacatgct    960
gggcgtcagc tatggcgata acctggattg ctacaaccag aggccctacc cgccttccta   1020
gttgatattt gatccgagca gacgaataaa atacaatgca cacgagattg tgagactcga   1080
gaaaacatat actacctctg aattttaata catatctcta aacaaaaaaa aaaaaaaaa    1140 aaaatatac                                                            1149

<210> SEQ ID NO 38
<211> LENGTH: 981
<212> TYPE: DNA
<213> ORGANISM: Oryza sativa
<220> FEATURE:
<221> NAME/KEY: misc_feature
<223> OTHER INFORMATION: TC84300 (PRO0151)

<400> SEQUENCE: 38
```

```
aagaggcaag agcatccgta ttaaccagcc ttttgagact tgagagtgtg tgtgactcga      60
tccagcgtag tttcagttcg tgtgttggtg agtgattcca gccaagtttg cgatggcttc     120
tcagcaggaa cgggctagct accacgccgg cgagaccaag gcccgcgccg aggagaagac     180
ggggcgcatg atgggcacgg cgcaggagaa ggcgcgggag gccaaggaca cggcgtccga     240
cgccgcgggg cgcgcgatgg gcaggggaca cggcgccaag gaggcgacca aggagaaggc     300
gtacgagacc aaggacgcga ccaaggagaa ggcgtacgag gcaaaggacg cggcctccga     360
cgccaccggc cgcgccatgg acaagggccg cggcgccgcg ggcgccacga gggacaaggc     420
gtacgatgcc aaggacaggg cggctgacac ggcgcagtcc gccgccgacc gcgcccgcga     480
cggcgccggg cagaccggga gctacattgg acagaccgcc gaggccgcca gcagaaagc     540
ggccggcgcc gcgcagtacg ccaaggagac cgcgatcgcc ggcaaggaca agaccggcgc     600
cgtgctccag caggcagggg agcaggtgaa gagcgtggcg gtggggcga aggacgcggt     660
gatgtacacg ctcgggatgt caggcgataa caagaacaac gccgctgccg gcaaggacac     720
cagcacctac aagcctggaa ctgggagtga ctaccagtaa tacggtagaa gaagcatgtg     780
tcgtctttgg cactgatgcc aaagtgtacg tgttgtatcc tctttttaa gtttcagctc      840
gacttcgacg tgttcggtgt cacacttggg tttttcagtt gtgctcaact gttcatgttt     900
ctggttccat ggagggccag tgtggaggtc aatgtttaag ctttcgtttt aaaatctgat     960
aataaagttg gttaagacct g                                               981
```

<210> SEQ ID NO 39
<211> LENGTH: 1203
<212> TYPE: DNA
<213> ORGANISM: Oryza sativa
<220> FEATURE:
<221> NAME/KEY: misc_feature
<223> OTHER INFORMATION: TC89687 (PRO0169)

<400> SEQUENCE: 39

```
tactcctctc tctcacctcc accatctagc tcactcacac agtctccact cacacgcatt      60
gcagaggaga ggcgacaatg gaggggaagg aggaggacgt gcggctgggg gcgaacaggt     120
actcggagag gcagccgata gggacggcgg cgcagggcgc gggggacgac aaggactaca     180
aggagccgcc gccgggccgc tgttcgagcc aggggagctc aagtcgtggt ctttctaccg     240
ggccgggatc gccgagttcg tcgccacctt cctcttcctc tacatcacca tcctcaccgt     300
catgggggtc tccaagtcct cctccaagtg cgccaccgtc ggcatccagg gcatcgcctg     360
gtccttcgga ggcatgatct tcgcgctcgt ctactgcacc gccggcatct ccggaggaca     420
catcaaccca gcagttactt ttgggctgtt cttggccagg aagctgtccc tgacccgggc     480
catcttctac atagtgatgc aatgcctagg ggccatctgc ggagctggag ttgtgaaggg     540
cttccagcag ggtctgtaca tgggcaatgg cggtggtgcc aatgtagttg ccagtggcta     600
caccaagggt gacggtcttg tgctgagat tgttggcacc ttcatcctgg tctacaccgt     660
cttctcagcc actgatgcca agaggaatgc cagggactca catgttccta tccttgcccc     720
actgccaatt ggttttgcgg tgttcctggt ccacctggcc accatcccca tcaccggtac     780
tggcatcaac ccagccagga gccttggcgc tgccatcatc tacaacaagg accatgcctg     840
gaatgaccat tggatcttct gggttggtcc cttcgttggc gctgccctgg ctgccatcta     900
ccaccaggtg atcatcaggg cgatcccatt caagagcagg tcttaagccc cgcgccgccg     960
ctgcgcagcc gacgacatgc aacgcaatcg tgatgtcctg tttcccgcgc gctactgctg    1020
```

| | |
|---|---|
| cgcatctgtc gattccctct atctctagtc cccaagatgt ttttcctatc tgaaccctga | 1080 |
| acaactcaat cgtgtaatcc agtactcagt cactgtatgt ttttatgtga tggagatctt | 1140 |
| aattcttaag ttatcatctc tgttgctgga aatccggttt cctcttcgtg catgaaccgc | 1200 |
| gcc | 1203 |

<210> SEQ ID NO 40
<211> LENGTH: 964
<212> TYPE: DNA
<213> ORGANISM: Oryza sativa
<220> FEATURE:
<221> NAME/KEY: misc_feature
<223> OTHER INFORMATION: TC89846 (PRO0170)

<400> SEQUENCE: 40

| | |
|---|---|
| cccacggttc cgcccacggt ccgcccacgg tccgcttctc ttctctggtg gtgtgggtgt | 60 |
| gtccctgtct cccctctcct tcctcctctc ctttcccctc ctctcttccc ccctctcaca | 120 |
| agagagagag cgccagactc tccccaggtg aggattcagc catgaagggg gccaaatcca | 180 |
| agggcgccgc caagcccgac gccaagttgg ctgtgaagag taagggcgcg gagaagcccg | 240 |
| ccgccaaggg caggaagggg aaggccggca aggaccccaa caagcccaag agggctccct | 300 |
| ccgcttcctt cgttttttatg gaggagttcc gtaaggagtt caaggagaag aaccccaaga | 360 |
| ataaatctgt cgctgctgta ggaaaagcag ccggtgatag gtggaaatcc ctgaccgaag | 420 |
| cggacaaggc tccctatgta gccaaggcca acaagctcaa ggccgagtac aacaaggcca | 480 |
| ttgctgccta caacaagggc gagagcactg ccaagaaggc cccgccaag gaggaagagg | 540 |
| aggacgacga ggaggaatct gacaagtcca agtccgaggt caatgatgag gatgacgacg | 600 |
| agggcagcga agaggatgaa gacgatgacg agtgagcctt ccagtggaca agatgggagc | 660 |
| agcaagacgc taagggcggc gggcgtccta aggagcctat ccatcatcat catcgtctac | 720 |
| tagaattatt cagtttcact tcacatcgtg atgttttact tttctctcg tcctataacg | 780 |
| gatagcgctc cttgttggcg ccactggtgg gtgttgtggt gcagccaatg tcttgtctcc | 840 |
| accgtcaatg atccgcttgt acctagatta ctctttccat tgtcatcggc taacattgtg | 900 |
| ataatatcag tttgcgtatg ttagattaaa ttgtttctaa ttccgtcgtt ttcttcttcc | 960 |
| ttgc | 964 |

<210> SEQ ID NO 41
<211> LENGTH: 1542
<212> TYPE: DNA
<213> ORGANISM: Oryza sativa
<220> FEATURE:
<221> NAME/KEY: misc_feature
<223> OTHER INFORMATION: TC82935 (PRO0171)

<400> SEQUENCE: 41

| | |
|---|---|
| cacacctcac acctcaccac catcacctcc tcctcctcct cctcttcctc cgcgcgcgcg | 60 |
| agatccaggg agagggagag ggagagatca tggcggggac ggtgacggtg ccgtcggcgt | 120 |
| cggtgccgtc gacgccgctg ctcaaggacg agctggacat cgtgatcccg acgatccgca | 180 |
| acctggactt cctggagatg tggcggccct tcttccagcc ctaccacctc atcatcgtgc | 240 |
| aggacggcga cccgaccaag accatccgcg tccccgaggg cttcgactac gagctctaca | 300 |
| accgcaacga catcaaccgg atcctcggcc ccaaggcctc ctgcatctcc ttcaaggact | 360 |
| ccgcatgccg ctgcttcggc tacatggtct ccaagaagaa gtacgtcttc accatcgacg | 420 |
| acgactgctt cgttgccaag gacccatctg gcaaggacat caatgctctt gagcagcaca | 480 |

```
tcaagaacct cctcagcccg tccacccccgt tcttcttcaa caccttgtat gatccctacc    540
gcgaaggcgc tgactttgtc cgtggttacc ccttcagcct cagggaggga gccaagactg    600
ctgtctctca cggcctgtgg cttaacatcc ctgactatga tgctcctact cagatggtca    660
agcctcgtga gaggaactcc aggtatgttg atgctgtcat gactgtgccc aagggaacct    720
tgttccccat gtgtggcatg aaccttgctt ttgaccgtga tctcatcggt cctgcaatgt    780
actttggtct catgggtgat ggccagccta ttggtcgcta cgacgacatg tgggctggat    840
ggtgcatgaa ggtcatctgt gaccacctga gcctgggagt gaagactgga ctgccgtaca    900
tctggcacag caaggctagc aaccccttcg tgaacttgaa gaaggaatac aagggcatct    960
tctggcagga ggacatcatc cccttcttcc agaacgccac catccccaag gagtgcgaca   1020
ccgtccagaa gtgctacctc tccctcgccg agcaggtcag ggagaagctc ggcaagatcg   1080 accccctactt cgtcaagctt gccgatgcca tggtcacctg gatcgaggcc tgggatgagc   1140
tgaacccctc gactgctgct gtcgagaacg gcaaggccaa gtagattgat cctgggagct   1200
tgtgtgtcgc aggatggaaa gtacccttta agtgaaagtg ttgctgtggc ctaggccccc   1260
tagatatagc tcttttttgag atgaagggag agattactta agcaacttta taattctttg   1320
ttgttatgct ggttcttttg tagctggaaa aggatttgtt atcatcgttt acataattca   1380
agacaataat aattttatca tgtaattttg atagtcgtgc tttggttgct aaatggtgtt   1440
attgtattta ataacctttg caaatcacta tacctgttgg ttgttctgag aattgtatgc   1500
actaccatat tatatttcta aatcatttcg taggcattat gg                      1542
```

<210> SEQ ID NO 42
<211> LENGTH: 1432
<212> TYPE: DNA
<213> ORGANISM: Oryza sativa
<220> FEATURE:
<221> NAME/KEY: misc_feature
<223> OTHER INFORMATION: TC82977 (PRO0173)
<220> FEATURE:
<221> NAME/KEY: misc_feature
<222> LOCATION: (1429)..(1429)
<223> OTHER INFORMATION: n = any nucleotide

<400> SEQUENCE: 42

```
aaaagagcag cgtcgcctct cctcctccct aaccccctacg cttccagaac cttctcgaag     60
ctcccgctcc cccccccctt ccgctccaat ggcgaaggaa ccgatgcgcg tgctcgtcac    120
cggcgccgca ggacaaattg gatatgctct tgtccccatg attgctaggg gtgtgatgtt    180
gggtgctgac cagcctgtta ttctacacat gcttgacatt ccaccagcta ctgaatctct    240
taatggcctt aagatggagc tggttgatgc tgcatttcct cttttgaagg gaattgtcgc    300
aacaactgat gttgtggagg cctgcactgg tgtgaatgtt gcggttatgg ttggtgggtt    360
ccccaggaag gagggaatgg aaaggaagga tgttatgtca aaaatgtctc catctacaa     420 atcccaagct tctgctcttg aggctcatgc agcccctaac tgcaaggttc tggtagttgc    480
caatccagca acaccaacg ctctcatctt aaaagaattc gctccatcca tccctgagaa    540
gaacattact tgcctcaccc gtcttgacca caacagggca cttggccaga tctctgaaaa    600
acttaatgtc caagttactg atgtgaagaa tgcgatcatc tggggcaacc actcatccac    660
ccagtaccct gatgttaacc acgccactgt gaagactcca gtggagaga agcctgtcag     720 ggaactcgtt gctgatgatg agtggttaaa tacggaattc atctctaccg tccagcagcg    780
tggtgccgcc atcatcaagg cgaggaagca atccagtgcc ctatctgctg ccagctctgc    840
```

```
atgcgatcac attcgtgact gggttcttgg cactcctgag ggaacatttg tctccatggg    900
tgtgtactct gatggttcgt atggtgtgcc tgctggtctg atctactcgt tcccagtaac    960
atgcagtggt ggcgaatgga cgattgttca gggtctcccg atcgacgagt tctcaaggaa   1020
gaagatggac gcgactgccc aggagctgtc ggaggagaag acgctcgctt actcatgcct   1080
caactaaaac taagcaatac ccagagggac agatagtgag cgattgcccg ctcccgtgtt   1140
tttgaataaa agagactttt aagttccatc acatagaaac tgtttatctc agaccgctgc   1200
acatcgcgag atgtggagcg cagatgccgt tgctggtttt actccagtgt gtattgaggc   1260
tttgtactag ctccctttt tttgcctggt gattcgcagg acatttgctg aaaacattga   1320
acccatttga catctgatgg aatcatggac cagtagcaag tacattttg cgaaagcata   1380
atctgcatcg ggcttgggct ggtggttgaa ctttctgcca catggcccnt gg           1432
```

<210> SEQ ID NO 43
<211> LENGTH: 659
<212> TYPE: DNA
<213> ORGANISM: Oryza sativa
<220> FEATURE:
<221> NAME/KEY: misc_feature
<223> OTHER INFORMATION: TC83646 (PRO0175)

<400> SEQUENCE: 43

```
gctaagtgag ctagccactg atcagaagaa cacctcgatc tctgagagtg ttttttcagc     60
tttagcttaa gcaggatgga gcaccagggg cagcacggcc acgtgaccag ccgcgtcgac    120
gagtacggca accggtcgg caccggcgcc ggacacggcc agatgggcac cgccggcatg    180
gggacgcacg gcaccgccgg caccggcggc ggccagttcc agccgatgag ggaggagcac    240
aagaccggcg gcgtcctgca acgctccggc agctccagct caagctcgtc tgaggatgat    300
ggaatgggag ggaggaggaa gaaggggatc aaggagaaga tcaaggagaa gctccccggc    360
ggcaacaagg gcgagcagca gcatgccatg ggcggcaccg gcaccggcac cggcaccggc    420
accggaaccg gcggcgccta cgggcagcag ggccacggca ccgggatgac caccggcacc    480
accggcgcac acggcaccac caccaccgac accggcgaga agaagggcat catggacaag    540
atcaaggaga agctgcccgg ccagcactga gctcgacaca ccaccacacc atgtgtctgc    600
gcccccggcg accgccgcca cgtcaccttc ctgaataata agatgagcta accgagcgc     659
```

<210> SEQ ID NO 44
<211> LENGTH: 1310
<212> TYPE: DNA
<213> ORGANISM: Oryza sativa
<220> FEATURE:
<221> NAME/KEY: misc_feature
<223> OTHER INFORMATION: TC90619 (PRO0177)

<400> SEQUENCE: 44

```
ggaccagcga gcaaccagcc ccccgccccc aatggcggca gagcagcttt gcccaccgct     60
gccgcttttg cccacctctc ctccgattaa tcccctcccc tcctcttcct cccacttctc    120
cgcctcctct tcctcccctc gccgacccta cctactcgcg ccgccgccgt cgcattgggc    180
ggcaaacgga gggggggtta accctgatgg agcagtacga gaaggaggag aagattgggg    240
agggcacgta cggggtggtg tacagggcgc gggacaaggt caccaacgag acgatcgcgc    300
tcaagaagat ccggcttgag caggaggatg agggcgtccc ctccaccgca atccgcgaga    360
tctcgctcct caaggagatg catcacggca acatcgtcag gttacacgat gttatccaca    420
```

```
gtgagaagcg catatatctt gtctttgagt atctggatct ggacctaaag aagttcatgg      480
actcttgtcc agagtttgcg aaaaacccca ctttaattaa gtcatatctc tatcagatac      540
tccgcggcgt tgcttactgt cattctcata gagttcttca tcgagatttg aaacctcaga      600
atttattgat agatcggcgt actaatgcac tgaagcttgc agactttggt ttagccaggg      660
catttggaat tcctgtccgc acgtttactc acgaggttgt aaccttgtgg tatagagctc      720
cagagatcct tcttggatca aggcagtatt ctacaccagt tgatatgtgg tcagttggtt      780
gtatctttgc agaaatggtg aaccagaaac cactgttccc tggtgattct gagattgatg      840
aattatttaa gatattcagg gtactaggaa ctccaaatga acaaagttgg ccaggagtta      900
gctcattacc tgactacaag tctgctttcc ccaagtggca agcacaggat cttgcaacta      960
ttgtccctac tcttgaccct gctggtttgg accttctctc taaaatgctt cggtacgagc     1020
caaacaaaag gatcacagct agacaggctc ttgagcatga atacttcaag gaccttgaga     1080
tggtacaatg accctgctat ggctttacat tggattggca tatgtatggg ctgggctcct     1140
catttcattc cttctgtgaa cgctgtgccc ttcgtttggg cattttttgtc attcagctgg     1200 atatttcaaa tcttgtgtgt ttgatatgta ttcaggaacg ctaaatagat caccgtcttg     1260
gtctctattt gttcagagta aatatcttcc aatgctgcct ttcagtttcc                1310

<210> SEQ ID NO 45
<211> LENGTH: 55
<212> TYPE: DNA
<213> ORGANISM: Artificial sequence
<220> FEATURE:
<223> OTHER INFORMATION: prm3780

<400> SEQUENCE: 45
ggggacaagt ttgtacaaaa aagcaggctt cgacgctact caagtggtgg gaggc          55

<210> SEQ ID NO 46
<211> LENGTH: 55
<212> TYPE: DNA
<213> ORGANISM: Artificial sequence
<220> FEATURE:
<223> OTHER INFORMATION: prm2768

<400> SEQUENCE: 46
ggggacaagt ttgtacaaaa aagcaggctc ccgatttagt agaccacatt ttggc          55

<210> SEQ ID NO 47
<211> LENGTH: 54
<212> TYPE: DNA
<213> ORGANISM: Artificial sequence
<220> FEATURE:
<223> OTHER INFORMATION: prm2420

<400> SEQUENCE: 47
ggggacaagt ttgtacaaaa aagcaggcta tgccatcgag tggtgtgccg atac           54

<210> SEQ ID NO 48
<211> LENGTH: 54
<212> TYPE: DNA
<213> ORGANISM: Artificial sequence
<220> FEATURE:
<223> OTHER INFORMATION: prm2853

<400> SEQUENCE: 48
ggggacaagt ttgtacaaaa aagcaggctt ctcttctgaa gctgaagccc tgcg           54
```

```
<210> SEQ ID NO 49
<211> LENGTH: 53
<212> TYPE: DNA
<213> ORGANISM: Artificial sequence
<220> FEATURE:
<223> OTHER INFORMATION: prm2426

<400> SEQUENCE: 49
ggggacaagt ttgtacaaaa aagcaggcta aaaccaccga gggacctgat ctg          53

<210> SEQ ID NO 50
<211> LENGTH: 55
<212> TYPE: DNA
<213> ORGANISM: Artificial sequence
<220> FEATURE:
<223> OTHER INFORMATION: prm2855

<400> SEQUENCE: 50
ggggacaagt ttgtacaaaa aagcaggctc ctagctatat gcagaggttg acagg        55

<210> SEQ ID NO 51
<211> LENGTH: 53
<212> TYPE: DNA
<213> ORGANISM: Artificial sequence
<220> FEATURE:
<223> OTHER INFORMATION: prm3025

<400> SEQUENCE: 51
ggggacaagt ttgtacaaaa aagcaggcta tggtgccatg tcaataagac atc          53

<210> SEQ ID NO 52
<211> LENGTH: 56
<212> TYPE: DNA
<213> ORGANISM: Artificial sequence
<220> FEATURE:
<223> OTHER INFORMATION: prm3029

<400> SEQUENCE: 52
ggggacaagt ttgtacaaaa aagcaggctg tttttctatg aaccggtcat taaacc       56

<210> SEQ ID NO 53
<211> LENGTH: 55
<212> TYPE: DNA
<213> ORGANISM: Artificial sequence
<220> FEATURE:
<223> OTHER INFORMATION: prm3061

<400> SEQUENCE: 53
ggggacaagt ttgtacaaaa aagcaggctc ctgatggatg atgaatcact gatcg        55

<210> SEQ ID NO 54
<211> LENGTH: 57
<212> TYPE: DNA
<213> ORGANISM: Artificial sequence
<220> FEATURE:
<223> OTHER INFORMATION: prm3031

<400> SEQUENCE: 54
ggggacaagt ttgtacaaaa aagcaggctt cgttaagttt gatgatttct gatgacc      57

<210> SEQ ID NO 55
<211> LENGTH: 53
<212> TYPE: DNA
<213> ORGANISM: Artificial sequence
<220> FEATURE:
<223> OTHER INFORMATION: prm3051
```

```
<400> SEQUENCE: 55
ggggaccact tgtacaaga aagctgggtg ccgccgctcg ctcgcttcgt tcg            53

<210> SEQ ID NO 56
<211> LENGTH: 58
<212> TYPE: DNA
<213> ORGANISM: Artificial sequence
<220> FEATURE:
<223> OTHER INFORMATION: prm3592

<400> SEQUENCE: 56
ggggacaagt ttgtacaaaa aagcaggctc gtgttcatgt tcgcatttag gattggac     58

<210> SEQ ID NO 57
<211> LENGTH: 55
<212> TYPE: DNA
<213> ORGANISM: Artificial sequence
<220> FEATURE:
<223> OTHER INFORMATION: prm5131

<400> SEQUENCE: 57
ggggacaagt ttgtacaaaa aagcaggctc agatgccaca gtatggtgta ccacc        55

<210> SEQ ID NO 58
<211> LENGTH: 56
<212> TYPE: DNA
<213> ORGANISM: Artificial sequence
<220> FEATURE:
<223> OTHER INFORMATION: prm3782

<400> SEQUENCE: 58
ggggacaagt ttgtacaaaa aagcaggctt tgcagttgtg accaagtaag ctgagc       56

<210> SEQ ID NO 59
<211> LENGTH: 54
<212> TYPE: DNA
<213> ORGANISM: Artificial sequence
<220> FEATURE:
<223> OTHER INFORMATION: prm2844

<400> SEQUENCE: 59
ggggacaagt ttgtacaaaa aagcaggctt ttggcgcggg gcagaagagt ggac         54

<210> SEQ ID NO 60
<211> LENGTH: 57
<212> TYPE: DNA
<213> ORGANISM: Artificial sequence
<220> FEATURE:
<223> OTHER INFORMATION: prm2973

<400> SEQUENCE: 60
ggggacaagt ttgtacaaaa aagcaggctg cttgagtcat agggagaaaa caaatcg      57

<210> SEQ ID NO 61
<211> LENGTH: 53
<212> TYPE: DNA
<213> ORGANISM: Artificial sequence
<220> FEATURE:
<223> OTHER INFORMATION: prm3770

<400> SEQUENCE: 61
ggggacaagt ttgtacaaaa aagcaggctc gtcctccttt tgtaacggct cgc          53

<210> SEQ ID NO 62
<211> LENGTH: 56
```

```
<212> TYPE: DNA
<213> ORGANISM: Artificial sequence
<220> FEATURE:
<223> OTHER INFORMATION: prm3772

<400> SEQUENCE: 62
ggggacaagt tgtacaaaa aagcaggctc atgcggctaa tgtagatgct cactgc      56

<210> SEQ ID NO 63
<211> LENGTH: 53
<212> TYPE: DNA
<213> ORGANISM: Artificial sequence
<220> FEATURE:
<223> OTHER INFORMATION: prm3774

<400> SEQUENCE: 63
ggggacaagt tgtacaaaa aagcaggctt agtaccattc ttccctcgtg agc          53

<210> SEQ ID NO 64
<211> LENGTH: 53
<212> TYPE: DNA
<213> ORGANISM: Artificial sequence
<220> FEATURE:
<223> OTHER INFORMATION: pm3776

<400> SEQUENCE: 64
ggggacaagt tgtacaaaa aagcaggctg tttggttggt gaccgcaatt tgc          53

<210> SEQ ID NO 65
<211> LENGTH: 55
<212> TYPE: DNA
<213> ORGANISM: Artificial sequence
<220> FEATURE:
<223> OTHER INFORMATION: prm3800

<400> SEQUENCE: 65
ggggacaagt tgtacaaaa aagcaggctg tcaccaccgt catgtacgag gctgc        55

<210> SEQ ID NO 66
<211> LENGTH: 55
<212> TYPE: DNA
<213> ORGANISM: Artificial sequence
<220> FEATURE:
<223> OTHER INFORMATION: prm5135

<400> SEQUENCE: 66
ggggacaagt tgtacaaaa aagcaggctc agacacctag aatatagaca ttccc        55

<210> SEQ ID NO 67
<211> LENGTH: 55
<212> TYPE: DNA
<213> ORGANISM: Artificial sequence
<220> FEATURE:
<223> OTHER INFORMATION: prm3781

<400> SEQUENCE: 67
ggggaccact tgtacaaga aagctgggtg atcacaagcg cagctaatca ctagc        55

<210> SEQ ID NO 68
<211> LENGTH: 57
<212> TYPE: DNA
<213> ORGANISM: Artificial sequence
<220> FEATURE:
<223> OTHER INFORMATION: prm2769

<400> SEQUENCE: 68
```

```
ggggaccact ttgtacaaga aagctgggtc gtgtagaaaa tcttaacccg aaaatcg        57
```

<210> SEQ ID NO 69
<211> LENGTH: 55
<212> TYPE: DNA
<213> ORGANISM: Artificial sequence
<220> FEATURE:
<223> OTHER INFORMATION: prm2421

<400> SEQUENCE: 69

```
ggggaccact ttgtacaaga aagctgggtg gtgaggtgcc ggggaagcga cgttg          55
```

<210> SEQ ID NO 70
<211> LENGTH: 54
<212> TYPE: DNA
<213> ORGANISM: Artificial sequence
<220> FEATURE:
<223> OTHER INFORMATION: prm2854

<400> SEQUENCE: 70

```
ggggaccact ttgtacaaga aagctgggtt tcttctttcc cttggaacta accg           54
```

<210> SEQ ID NO 71
<211> LENGTH: 54
<212> TYPE: DNA
<213> ORGANISM: Artificial sequence
<220> FEATURE:
<223> OTHER INFORMATION: prm2427

<400> SEQUENCE: 71

```
ggggaccact ttgtacaaga aagctgggtt gtcgcttttta tttggcttgg tgtg          54
```

<210> SEQ ID NO 72
<211> LENGTH: 56
<212> TYPE: DNA
<213> ORGANISM: Artificial sequence
<220> FEATURE:
<223> OTHER INFORMATION: prm2856

<400> SEQUENCE: 72

```
ggggaccact ttgtacaaga aagctgggtc tctagctcga tctctcttgc aaaagc         56
```

<210> SEQ ID NO 73
<211> LENGTH: 49
<212> TYPE: DNA
<213> ORGANISM: Artificial sequence
<220> FEATURE:
<223> OTHER INFORMATION: prm3026

<400> SEQUENCE: 73

```
ggggaccact ttgtacaaga aagctgggtg gcgatgagat cttcctccg                 49
```

<210> SEQ ID NO 74
<211> LENGTH: 59
<212> TYPE: DNA
<213> ORGANISM: Artificial sequence
<220> FEATURE:
<223> OTHER INFORMATION: prm3030

<400> SEQUENCE: 74

```
ggggaccact ttgtacaaga aagctgggtt tttgtaggat tctactacta tgcttcaac      59
```

<210> SEQ ID NO 75
<211> LENGTH: 62
<212> TYPE: DNA
<213> ORGANISM: Artificial sequence -continued
<220> FEATURE:
<223> OTHER INFORMATION: prm3062

<400> SEQUENCE: 75
ggggaccact ttgtacaaga aagctgggta ttgtgtaaat atttctattg tccagtaatc    60
ac    62

<210> SEQ ID NO 76
<211> LENGTH: 54
<212> TYPE: DNA
<213> ORGANISM: Artificial sequence
<220> FEATURE:
<223> OTHER INFORMATION: prm3032

<400> SEQUENCE: 76
ggggaccact ttgtacaaga aagctgggtg atggcagagt taattagcaa acgc    54

<210> SEQ ID NO 77
<211> LENGTH: 50
<212> TYPE: DNA
<213> ORGANISM: Artificial sequence
<220> FEATURE:
<223> OTHER INFORMATION: prm3052

<400> SEQUENCE: 77
ggggacaagt ttgtacaaaa aagcaggctc taagggcagc agccattggg    50

<210> SEQ ID NO 78
<211> LENGTH: 60
<212> TYPE: DNA
<213> ORGANISM: Artificial sequence
<220> FEATURE:
<223> OTHER INFORMATION: prm3049

<400> SEQUENCE: 78
ggggaccact ttgtacaaga aagctgggtg gcggcggcgg cggcggcggc ggctgggtct    60

<210> SEQ ID NO 79
<211> LENGTH: 54
<212> TYPE: DNA
<213> ORGANISM: Artificial sequence
<220> FEATURE:
<223> OTHER INFORMATION: prm2195

<400> SEQUENCE: 79
ggggaccact ttgtacaaga aagctgggtc ggcttagaga ggggaggaag cgaa    54

<210> SEQ ID NO 80
<211> LENGTH: 58
<212> TYPE: DNA
<213> ORGANISM: Artificial sequence
<220> FEATURE:
<223> OTHER INFORMATION: prm2197

<400> SEQUENCE: 80
ggggaccact ttgtacaaga aagctgggtt ggtgtgagtg tttgagtttg gagtgagc    58

<210> SEQ ID NO 81
<211> LENGTH: 57
<212> TYPE: DNA
<213> ORGANISM: Artificial sequence
<220> FEATURE:
<223> OTHER INFORMATION: prm2845

<400> SEQUENCE: 81 gggaccact ttgtacaaga aagctgggtc ggcaatgtga tgcaatgcaa attaagc    57

<210> SEQ ID NO 82
<211> LENGTH: 55
<212> TYPE: DNA
<213> ORGANISM: Artificial sequence
<220> FEATURE:
<223> OTHER INFORMATION: prm2974

<400> SEQUENCE: 82 gggaccact ttgtacaaga aagctgggtc gcaaacttgg ctggaatcac tcacc    55

<210> SEQ ID NO 83
<211> LENGTH: 54
<212> TYPE: DNA
<213> ORGANISM: Artificial sequence
<220> FEATURE:
<223> OTHER INFORMATION: prm3771

<400> SEQUENCE: 83 gggaccact ttgtacaaga aagctgggtt gtcgcctctc ctctgcaatg cgtg    54

<210> SEQ ID NO 84
<211> LENGTH: 52
<212> TYPE: DNA
<213> ORGANISM: Artificial sequence
<220> FEATURE:
<223> OTHER INFORMATION: prm3773

<400> SEQUENCE: 84 gggaccact ttgtacaaga aagctgggtg gctgaatcct gcgagaaggg cg    52

<210> SEQ ID NO 85
<211> LENGTH: 54
<212> TYPE: DNA
<213> ORGANISM: Artificial sequence
<220> FEATURE:
<223> OTHER INFORMATION: prm3775

<400> SEQUENCE: 85 gggaccact ttgtacaaga aagctgggtg atctctccct ctccctctcc ctgg    54

<210> SEQ ID NO 86
<211> LENGTH: 52
<212> TYPE: DNA
<213> ORGANISM: Artificial sequence
<220> FEATURE:
<223> OTHER INFORMATION: prm3777

<400> SEQUENCE: 86 gggaccact ttgtacaaga aagctgggtt ggagcggaag gggggggga gc    52

<210> SEQ ID NO 87
<211> LENGTH: 57
<212> TYPE: DNA
<213> ORGANISM: Artificial sequence
<220> FEATURE:
<223> OTHER INFORMATION: prm3801

<400> SEQUENCE: 87 gggaccact ttgtacaaga aagctgggtc actctcagag atcgaggtgt tcttctg    57

<210> SEQ ID NO 88
<211> LENGTH: 52
<212> TYPE: DNA
<213> ORGANISM: Artificial sequence

```
<220> FEATURE:
<223> OTHER INFORMATION: prm5136

<400> SEQUENCE: 88
ggggaccact ttgtacaaga aagctgggtc gcccgcagct cgcccccgtc cg            52
```